(12) United States Patent
Pastan et al.

(10) Patent No.: US 7,999,077 B2
(45) Date of Patent: Aug. 16, 2011

(54) IRTA2 ANTIBODIES AND METHODS OF USE

(75) Inventors: Ira Pastan, Potomac, MD (US);
Tomoko Ise, Rockville, MD (US);
Laiman Xiang, Fairfax, VA (US);
Satoshi Nagata, Rockville, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 776 days.

(21) Appl. No.: 11/664,211

(22) PCT Filed: Sep. 22, 2005

(86) PCT No.: PCT/US2005/034444
§ 371 (c)(1),
(2), (4) Date: Mar. 28, 2007

(87) PCT Pub. No.: WO2006/039238
PCT Pub. Date: Apr. 13, 2006

(65) Prior Publication Data
US 2008/0292632 A1    Nov. 27, 2008

Related U.S. Application Data

(60) Provisional application No. 60/615,406, filed on Sep. 30, 2004.

(51) Int. Cl.
*C07K 16/00* (2006.01)
*C12P 21/08* (2006.01)
*C12Q 1/00* (2006.01)
*G01N 33/53* (2006.01)
*C12N 5/02* (2006.01)
*C12N 5/06* (2006.01)
*C07K 17/00* (2006.01)

(52) U.S. Cl. ............... 530/387.1; 530/387.3; 530/387.9; 530/388.1; 435/4; 435/7.1; 435/325; 435/326

(58) Field of Classification Search .................. None
See application file for complete search history.

(56) References Cited

U.S. PATENT DOCUMENTS

| | | | | |
|---|---|---|---|---|
| 4,892,827 | A | * | 1/1990 | Pastan et al. ............... 435/193 |
| 5,530,101 | A | * | 6/1996 | Queen et al. ............... 530/387.3 |
| 5,602,095 | A | * | 2/1997 | Pastan et al. ............... 514/12 |
| 5,608,039 | A | * | 3/1997 | Pastan et al. ............... 530/387.3 |

FOREIGN PATENT DOCUMENTS

| | | |
|---|---|---|
| WO | WO 01/38490 | 5/2001 |
| WO | WO 03/024392 | 3/2003 |
| WO | WO 03/083076 | 10/2003 |
| WO | WO 03/089624 | 10/2003 |
| WO | WO 2004/045516 | 6/2004 |
| WO | WO 2005/063299 | 7/2005 |

OTHER PUBLICATIONS

SEQ ID No. 13 alingment with IRTA2 from WO 01/38490. p. 1. generated on Jun. 16, 2009.*
Rudikoff et al. PNAS 1982 vol. 79, pp. 1979-1983.*
Rader et al. PNAS. 1998. 95:8910-8915.*
Pai et al. PNAS 1991. 88:3358-62.*
Kondo et al. JBC 1988. 263:9470-9475.*
Pastan et al. Biochim. Biophys. Acta. 1997. 1333:C1-C6.*
Coleman et al. Research in Immunology, 1994; 145(1): 33-36.*
"Anti-IRTA2 Polyclonal Antibody," Product Sheet, cites Hatzivassiliou et al., *Immunity* 14:272-289, 2001.
Aurias and Dutrillaux, "Probably involvement in immunoglobulin superfamily genes in most recurrent chromosomal rearrangements from ataxia telangiectasia," *Human Genetics* 72(3):210-4, Mar. 1986 *Abstract Only*.
Dalton et al., "Multiple Myeloma," *Hematology* p. 157-177, 2001.
Davis et al., "Fc receptor homologs: newest members of a remarkably diverse Fc receptor gene family," *Immunological Review* 190:123-136, 2002.
Davis et al., "Identification of a family of Fc receptor homologs with preferential B cell expression," *PNAS* 98(17):9772-9777, Aug. 14, 2001.
Falini et al., "Expression of the IRTA1 receptor identifies intraepithelial and subepithelial marginal zone B cells of the mucosa-associated lymphoid tissue (MALT)," *Blood* 102(10):3684-3692, Nov. 15, 2003.
Gozzetti et al., "Identification of Novel Cryptic Translocations Involving *IGH* in B-Cell Non-Hodgkin's Lymphomas," *Cancer research* 62:5523-5527, Oct. 1, 2002.
Hatzivassiliou et al., "IRTA1 and IRTA2, novel immunoglobulin superfamily receptor expressed in B cells and involved in chromosome 1q21 abnormalities in B cell malignancy," *Immunity* 14(3):277-289, Mar. 2001.
Ise et al., "Immunoglobulin Superfamily Receptor Translocation Associated 2 Protein on Lymphoma Cell Lines and Hairy Cell Leukemia Cells Detected by Novel Monoclonal Antibodies," *Clinical Cancer Research* 11:87-96, Jan. 1, 2005.
Ise et al., "ITRA2 Protein on Lymphoma Cell Lines and Hairy Cell Leukemia Cells Detected by Novel Monoclonal Antibodies," *Blood* 104(11):313A, Nov. 2004 *Abstract Only*.
Itoyama, et al., "Molecular cytogenetic analysis of genomic instability at the 1q12-22 chromosomal site in B-cell non-Hodgkin lymphoma," *Genes, Chromosomes and Cancer* 35(4):318-328, published online Jul. 23, 2002 *Abstract Only*.

(Continued)

*Primary Examiner* — Chun Dahle
(74) *Attorney, Agent, or Firm* — Klarquist Sparkman, LLP

(57) ABSTRACT

Antibodies that specifically bind the extracellular domain of IRTA2 are disclosed herein. In one embodiment, these antibodies do not specifically bind IRTA1, IRTA3, IRTA4, or IRTA5. In one example, the antibodies are humanized antibodies. The antibodies can be conjugated to effector molecules, including detectable labels, radionucleotides, toxins and chemotherapeutic agents. The antibodies that specifically bind IRTA2 are of use to detect B cell malignancies, such as hairy cell leukemia and non-Hodgkin's lymphoma. These antibodies that specifically bind IRTA2 are also of use to treat B cell malignancies that express IRTA2, such as hairy cell leukemia and non-Hodgkin's lymphoma.

17 Claims, 11 Drawing Sheets

OTHER PUBLICATIONS

Miller et al., "IRTAs: a new family of immunoglobulinlike receptors differentially expressed in B cells," *Blood* 99(8):2662-2669, Apr. 15, 2002.

Nakayama et al., "BXMAS1 Identifies a Cluster of Homologous Genes Differentially Expressed in B Cells," *Biochemical and Biophysical Research Communications* 285:830-837, 2001.

Pileri et al., "Indolent lymphoma: the pathologist's viewpoint," *Annals of Oncology* 15:12-18, 2004.

Accession No. NM 031281, Davis et al., http://www.ncbi.nlm.nih.gov/entrez/viewer.fcgi?db=nucleotide&val+14550413, printed Aug. 3, 2004.

Besa, et al., "Hairy Cell Leukemia," *eMedicine* found at http://emedicine.com/med/topic937.htm printed Aug. 2, 2004.

Gentaur Molecular Products bvba Immune System, found at http://www.gentaur.com/acatalog/GENTAUR_Immune_System_192.html, printed Aug. 3, 2004.

"Hairy Cell Leukemia," *National Cancer Institute* found at http://www.imsdd.meb.uni-bonn.de/cancer.gov/CDR0000062926.html printed on Aug. 2, 2004.

"Immunoglobulin superfamily receptor translocation associated 2 IR polyclonal antibody," *Orbigen, Inc.* found at http://www.orbigen.com/commerce/catalog/product.jsp?product_id+1846, printed Aug. 3, 2004.

"*Homo sapiens* gene IRTA2 encoding immunoglobulin superfamily receptor translocation associated 2," found at http://www.ncbi.nlm.nih.gov/IEB/Research/Acembly/av.cgi?db+human&c+gene&a=fiche&... printed Aug. 3, 2004.

"Immunoglobulin Superfamily Receptor Translocation-Associated Gene2," *OMIM* found at http://www.ncbi.nlm.nih.gov/entrez/query.fcgi?cmd=Retrieve&db=OMIM&dopt=Detailed... printed Aug. 3, 2004.

* cited by examiner

SEQUENCE LISTING

<160> NUMBER OF SEQ ID NOS: 57

<210> SEQ ID NO 1
<211> LENGTH: 120
<212> TYPE: PRT
<213> ORGANISM: Mus musculus

<400> SEQUENCE: 1

Asp Val Gln Leu Val Glu Ser Gly Gly Gly Leu Val Gln Pro Gly Gly
1               5                   10                  15

Ser Arg Lys Leu Ser Cys Thr Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Asn Asn Ile Tyr Phe Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Ser Glu Tyr Tyr Gly Ser Ser His Met Asp Tyr Trp Gly Gln
            100                 105                 110

Gly Thr Ser Val Thr Val Ser Ser
        115                 120

<210> SEQ ID NO 2
<211> LENGTH: 112
<212> TYPE: PRT
<213> ORGANISM: Mus musculus

<400> SEQUENCE: 2

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Phe Gln Gln Lys Pro Gly Gln Ser Pro Lys Leu Leu Ile
        35                  40                  45

Tyr Tyr Ala Ser Asn His Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Pro
                85                  90                  95

Thr Phe Gly Gly Gly Thr Lys Leu Glu Ile Lys Arg Ala Asp Ala Ala
            100                 105                 110

<210> SEQ ID NO 3
<211> LENGTH: 118
<212> TYPE: PRT
<213> ORGANISM: Mus musculus

<400> SEQUENCE: 3

Asp Val His Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ile Phe
            20                  25                  30

Gly Leu His Trp Val Arg Gln Ala Pro Glu Lys Gly Leu Glu Trp Val

```
                35                  40                  45
Ala Tyr Ile Ser Gly Gly Asp Ser Asn Thr Ile Tyr Tyr Ala Asp Thr
 50                  55                  60

Val Lys Gly Arg Phe Thr Ile Ser Arg Asp Asn Pro Lys Asn Thr Leu
 65                  70                  75                  80

Phe Leu Gln Met Thr Ser Leu Arg Ser Glu Asp Thr Ala Met Tyr Tyr
                 85                  90                  95

Cys Ala Arg Asn Ser Tyr Tyr Ala Leu Asp Tyr Trp Gly Gln Gly Thr
                100                 105                 110

Ser Val Thr Val Ser Ser
            115

<210> SEQ ID NO 4
<211> LENGTH: 113
<212> TYPE: PRT
<213> ORGANISM: Mus musculus

<400> SEQUENCE: 4

Glu Asn Val Phe Thr Gln Ser Pro Ala Ile Met Ser Val Ser Pro Gly
  1               5                  10                  15

Glu Lys Val Thr Met Thr Cys Arg Ala Ser Ser Ser Val Ser Ser Ser
                 20                  25                  30

Tyr Leu His Trp Tyr Gln Gln Arg Ser Gly Ala Ser Pro Lys Ile Trp
             35                  40                  45

Ile Tyr Ser Thr Ser Asn Leu Ala Ser Gly Val Pro Ala Arg Phe Ser
 50                  55                  60

Gly Ser Gly Thr Gly Thr Ser Tyr Ser Leu Thr Ile Ser Ser Val Glu
 65                  70                  75                  80

Ala Glu Asp Ala Ala Thr Tyr Tyr Cys Gln Gln Tyr Ser Gly Tyr Pro
                 85                  90                  95

Trp Thr Phe Gly Gly Gly Thr Lys Leu Glu Ile Lys Arg Ala Asp Ala
                100                 105                 110

Ala

<210> SEQ ID NO 5
<211> LENGTH: 116
<212> TYPE: PRT
<213> ORGANISM: Mus musculus

<400> SEQUENCE: 5

Glu Val Gln Leu Gln Gln Ser Gly Pro Glu Leu Val Lys Pro Gly Thr
  1               5                  10                  15

Ser Val Lys Met Ser Cys Lys Ala Ser Gly Tyr Ser Phe Thr Gly Tyr
                 20                  25                  30

Phe Met Asn Trp Met Met Gln Asn His Gly Lys Ser Leu Glu Trp Ile
             35                  40                  45

Gly Arg Ile Asn Leu Tyr Asn Gly Asp Thr Phe Tyr Asn Gln Lys Phe
 50                  55                  60

Lys Asp Lys Ala Thr Leu Thr Val Asp Lys Ser Ser Asn Thr Val His
 65                  70                  75                  80

Met Glu Phe Arg Ser Leu Ala Ser Glu Asp Ser Ala Val Tyr Tyr Cys
                 85                  90                  95

Ala Ser Ser Leu Tyr Tyr Phe Asp Tyr Trp Gly Gln Gly Thr Thr Phe
                100                 105                 110

Thr Val Ser Ser
            115
```

<210> SEQ ID NO 6
<211> LENGTH: 112
<212> TYPE: PRT
<213> ORGANISM: Mus musculus

<400> SEQUENCE: 6

```
Asp Ile Val Met Thr Gln Ser His Lys Phe Met Ser Thr Ser Val Gly
1               5                   10                  15

Asp Arg Val Asn Ile Thr Cys Lys Ala Ser Gln Asp Val Gly Thr Asn
            20                  25                  30

Val Ala Trp Tyr Gln Gln Lys Pro Gly Gln Ser Pro Lys Leu Leu Ile
        35                  40                  45

Tyr Trp Ala Ser Thr Arg Gln Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ser Asp Tyr Phe Cys Gln Gln Tyr Ser Ser Tyr Pro Leu
                85                  90                  95

Thr Phe Gly Ala Gly Thr Lys Leu Glu Leu Lys Arg Ala Asp Ala Ala
            100                 105                 110
```

<210> SEQ ID NO 7
<211> LENGTH: 360
<212> TYPE: DNA
<213> ORGANISM: Mus musculus

<400> SEQUENCE: 7

```
gatgtgcagc tggtggagtc tgggggaggc ttagtgcagc ctggagggtc cggaaactc     60
tcctgtacag cctctggatt cactttcagt agctttggaa tgcactgggt tcgtcaggct    120
ccagagaagg ggctggagtg ggtcgcatac attagtagtg gcagtaataa catctacttt    180
gcggacacag tgaagggccg attcaccatc tccagagaca atcccaagaa caccctgttc    240
ctgcaaatga ccagtctaag gtctgaggac acggccatgt attactgtgc aagatcggaa    300
tactacggta gtagccatat ggactactgg ggtcaaggaa cctcagtcac cgtctcctca    360
```

<210> SEQ ID NO 8
<211> LENGTH: 336
<212> TYPE: DNA
<213> ORGANISM: Mus musculus

<400> SEQUENCE: 8

```
agtattgtga tgacccagac tcccaaattc ctgcttgtat cagcaggaga cagggttacc    60
ataacctgca aggccagtca gagtgtgagt aatgatgtag cttggttcca acagaagcca    120
gggcagtctc ctaaactgct gatatactat gcatccaatc actacactgg agtccctgat    180
cgcttcactg gcagtggata tgggacggat ttcactttca ccatcagcac tgtgcaggct    240
gaagacctgg cagtttattt ctgtcagcag gattatagct ctcctccgac gttcggtgga    300
ggcaccaagc tggaaatcaa acgggctgat gctgca                              336
```

<210> SEQ ID NO 9
<211> LENGTH: 351
<212> TYPE: DNA
<213> ORGANISM: Mus musculus

<400> SEQUENCE: 9

```
gatgtgcacc tggtggagtc tgggggaggc ttagtgcagc ctggagggtc cggaaactc     60
tcctgtgcag cctctggatt cactttcagt atctttggat tgcactgggt tcgtcaggct    120
```

```
ccagagaagg ggctggagtg ggtcgcatac attagtggtg acagtaatac catctactat    180
gcagacacag tgaagggccg attcaccatc tccagagaca atcccaagaa caccctgttc    240
ctgcaaatga ccagtctaag gtctgaggac acggccatgt attactgtgc aagaaatagc    300
tactatgctc tggactactg gggtcaagga acctcagtca ccgtctcctc a             351

<210> SEQ ID NO 10
<211> LENGTH: 339
<212> TYPE: DNA
<213> ORGANISM: Mus musculus

<400> SEQUENCE: 10
gaaaatgtgt tcacccagtc tccagcaatc atgtctgtat ctccaggtga aaaggtcacc     60
atgacctgca gggccagctc aagtgtcagt tccagttact gcactggta ccagcagagg    120 tcaggtgcct cccccaaaat ctggatttat agcacatcca acttggcttc tggagtccct    180
gctcgcttca gtggcagtgg gactgggacc tcttactctc tcacaatcag cagtgtggag    240
gctgaagatg ctgccactta ttactgccag cagtacagtg gttacccgtg gacgttcggt    300
ggaggcacca agttggaaat caaacgggct gatgctgca                           339

<210> SEQ ID NO 11
<211> LENGTH: 348
<212> TYPE: DNA
<213> ORGANISM: Mus musculus

<400> SEQUENCE: 11
gaggttcaac tgcagcagtc tggacctgag ctggtgaagc ctgggacttc agtgaagatg     60
tcctgcaagg cttctggtta ctcatttact ggctacttta tgaactggat gatgcagaac    120
catggaaaga gccttgagtg gattggacgt attaatcttt acaatggtga tactttctac    180
aaccagaagt tcaaggacaa ggccacattg actgtggaca atcctctaa cacagtccac    240 atggagttcc ggagcctggc atctgaggac tctgcagtct attattgtgc aagtagtctg    300
tactactttg actactgggg ccaaggcacc actttcacag tctcctca                 348

<210> SEQ ID NO 12
<211> LENGTH: 336
<212> TYPE: DNA
<213> ORGANISM: Mus musculus

<400> SEQUENCE: 12
gacattgtga tgacccagtc tcacaaattc atgtccacat cagtaggaga cagggtcaat     60
attacctgta aggccagtca ggatgtgggt actaatgtag cctggtatca acagaaacca    120
gggcaatctc ctaaactact gatttactgg gcatccaccc ggcagactgg agtccctgat    180
cgcttcacag gcagtggatc tgggacagat ttcactctca ccattagcaa tgtgcagtct    240
gaagacttgt cagattattt ctgtcagcaa tatagcagct atcctctcac gttcggtgct    300
gggaccaagc tggagctgaa acgggctgat gctgca                              336

<210> SEQ ID NO 13
<211> LENGTH: 759
<212> TYPE: PRT
<213> ORGANISM: Homo sapiens

<400> SEQUENCE: 13

Met Leu Leu Trp Val Ile Leu Leu Val Leu Ala Pro Val Ser Gly Gln
1               5                   10                  15
```

```
Phe Ala Arg Thr Pro Arg Pro Ile Ile Phe Leu Gln Pro Pro Trp Thr
            20              25              30
Thr Val Phe Gln Gly Glu Arg Val Thr Leu Thr Cys Lys Gly Phe Arg
        35              40              45
Phe Tyr Ser Pro Gln Lys Thr Lys Trp Tyr His Arg Tyr Leu Gly Lys
50              55              60
Glu Ile Leu Arg Glu Thr Pro Asp Asn Ile Leu Glu Val Gln Glu Ser
65              70              75              80
Gly Glu Tyr Arg Cys Gln Ala Gln Gly Ser Pro Leu Ser Ser Pro Val
            85              90              95
His Leu Asp Phe Ser Ser Ala Ser Leu Ile Leu Gln Ala Pro Leu Ser
            100             105             110
Val Phe Glu Gly Asp Ser Val Val Leu Arg Cys Arg Ala Lys Ala Glu
        115             120             125
Val Thr Leu Asn Asn Thr Ile Tyr Lys Asn Asp Asn Val Leu Ala Phe
        130             135             140
Leu Asn Lys Arg Thr Asp Phe His Ile Pro His Ala Cys Leu Lys Asp
145             150             155             160
Asn Gly Ala Tyr Arg Cys Thr Gly Tyr Lys Glu Ser Cys Cys Pro Val
            165             170             175
Ser Ser Asn Thr Val Lys Ile Gln Val Gln Glu Pro Phe Thr Arg Pro
            180             185             190
Val Leu Arg Ala Ser Ser Phe Gln Pro Ile Ser Gly Asn Pro Val Thr
        195             200             205
Leu Thr Cys Glu Thr Gln Leu Ser Leu Glu Arg Ser Asp Val Pro Leu
        210             215             220
Arg Phe Arg Phe Phe Arg Asp Asp Gln Thr Leu Gly Leu Gly Trp Ser
225             230             235             240
Leu Ser Pro Asn Phe Gln Ile Thr Ala Met Trp Ser Lys Asp Ser Gly
            245             250             255
Phe Tyr Trp Cys Lys Ala Ala Thr Met Pro His Ser Val Ile Ser Asp
            260             265             270
Ser Pro Arg Ser Trp Ile Gln Val Gln Ile Pro Ala Ser His Pro Val
        275             280             285
Leu Thr Leu Ser Pro Glu Lys Ala Leu Asn Phe Glu Gly Thr Lys Val
        290             295             300
Thr Leu His Cys Glu Thr Gln Glu Asp Ser Leu Arg Thr Leu Tyr Arg
305             310             315             320
Phe Tyr His Glu Gly Val Pro Leu Arg His Lys Ser Val Arg Cys Glu
            325             330             335
Arg Gly Ala Ser Ile Ser Phe Ser Leu Thr Thr Glu Asn Ser Gly Asn
            340             345             350
Tyr Tyr Cys Thr Ala Asp Asn Gly Leu Gly Ala Lys Pro Ser Lys Ala
        355             360             365
Val Ser Leu Ser Val Thr Val Pro Val Ser His Pro Val Leu Asn Leu
        370             375             380
Ser Ser Pro Glu Asp Leu Ile Phe Glu Gly Ala Lys Val Thr Leu His
385             390             395             400
Cys Glu Ala Gln Arg Gly Ser Leu Pro Ile Leu Tyr Gln Phe His His
            405             410             415
Glu Asp Ala Ala Leu Glu Arg Arg Ser Ala Asn Ser Ala Gly Gly Val
            420             425             430
Ala Ile Ser Phe Ser Leu Thr Ala Glu His Ser Gly Asn Tyr Tyr Cys
        435             440             445
```

```
Thr Ala Asp Asn Gly Phe Gly Pro Gln Arg Ser Lys Ala Val Ser Leu
    450                 455                 460

Ser Ile Thr Val Pro Val Ser His Pro Val Leu Thr Leu Ser Ser Ala
465                 470                 475                 480

Glu Ala Leu Thr Phe Glu Gly Ala Thr Val Thr Leu His Cys Glu Val
                485                 490                 495

Gln Arg Gly Ser Pro Gln Ile Leu Tyr Gln Phe Tyr His Glu Asp Met
            500                 505                 510

Pro Leu Trp Ser Ser Ser Thr Pro Ser Val Gly Arg Val Ser Phe Ser
        515                 520                 525

Phe Ser Leu Thr Glu Gly His Ser Gly Asn Tyr Tyr Cys Thr Ala Asp
    530                 535                 540

Asn Gly Phe Gly Pro Gln Arg Ser Glu Val Val Ser Leu Phe Val Thr
545                 550                 555                 560

Val Pro Val Ser Arg Pro Ile Leu Thr Leu Arg Val Pro Arg Ala Gln
                565                 570                 575

Ala Val Val Gly Asp Leu Leu Glu Leu His Cys Glu Ala Pro Arg Gly
            580                 585                 590

Ser Pro Pro Ile Leu Tyr Trp Phe Tyr His Glu Asp Val Thr Leu Gly
        595                 600                 605

Ser Ser Ser Ala Pro Ser Gly Gly Glu Ala Ser Phe Asn Leu Ser Leu
    610                 615                 620

Thr Ala Glu His Ser Gly Asn Tyr Ser Cys Glu Ala Asn Asn Gly Leu
625                 630                 635                 640

Val Ala Gln His Ser Asp Thr Ile Ser Leu Ser Val Ile Val Pro Val
                645                 650                 655

Ser Arg Pro Ile Leu Thr Phe Arg Ala Pro Arg Ala Gln Ala Val Val
            660                 665                 670

Gly Asp Leu Leu Glu Leu His Cys Glu Ala Leu Arg Gly Ser Ser Pro
        675                 680                 685

Ile Leu Tyr Trp Phe Tyr His Glu Asp Val Thr Leu Gly Lys Ile Ser
    690                 695                 700

Ala Pro Ser Gly Gly Gly Ala Ser Phe Asn Leu Ser Leu Thr Thr Glu
705                 710                 715                 720

His Ser Gly Ile Tyr Ser Cys Glu Ala Asp Asn Gly Leu Glu Ala Gln
                725                 730                 735

Arg Ser Glu Met Val Thr Leu Lys Val Ala Gly Glu Trp Ala Leu Pro
            740                 745                 750

Thr Ser Ser Thr Ser Glu Asn
        755

<210> SEQ ID NO 14
<211> LENGTH: 515
<212> TYPE: PRT
<213> ORGANISM: Homo sapiens

<400> SEQUENCE: 14

Met Leu Leu Trp Ala Ser Leu Leu Ala Phe Ala Pro Val Cys Gly Gln
1               5                   10                  15

Ser Ala Ala Ala His Lys Pro Val Ile Ser Val His Pro Pro Trp Thr
            20                  25                  30

Thr Phe Phe Lys Gly Glu Arg Val Thr Leu Thr Cys Asn Gly Phe Gln
        35                  40                  45

Phe Tyr Ala Thr Glu Lys Thr Thr Trp Tyr His Arg His Tyr Trp Gly
    50                  55                  60
```

```
Glu Lys Leu Thr Leu Thr Pro Gly Asn Thr Leu Glu Val Arg Glu Ser
 65                  70                  75                  80

Gly Leu Tyr Arg Cys Gln Ala Arg Gly Ser Pro Arg Ser Asn Pro Val
                 85                  90                  95

Arg Leu Leu Phe Ser Ser Asp Ser Leu Ile Leu Gln Ala Pro Tyr Ser
            100                 105                 110

Val Phe Glu Gly Asp Thr Leu Val Leu Arg Cys His Arg Arg Arg Lys
        115                 120                 125

Glu Lys Leu Thr Ala Val Lys Tyr Thr Trp Asn Gly Asn Ile Leu Ser
130                 135                 140

Ile Ser Asn Lys Ser Trp Asp Leu Leu Ile Pro Gln Ala Ser Ser Asn
145                 150                 155                 160

Asn Asn Gly Asn Tyr Arg Cys Ile Gly Tyr Gly Asp Glu Asn Asp Val
                165                 170                 175

Phe Arg Ser Asn Phe Lys Ile Ile Lys Ile Gln Glu Leu Phe Pro His
            180                 185                 190

Pro Glu Leu Lys Ala Thr Asp Ser Gln Pro Thr Glu Gly Asn Ser Val
        195                 200                 205

Asn Leu Ser Cys Glu Thr Gln Leu Pro Pro Glu Arg Ser Asp Thr Pro
210                 215                 220

Leu His Phe Asn Phe Phe Arg Asp Gly Glu Val Ile Leu Ser Asp Trp
225                 230                 235                 240

Ser Thr Tyr Pro Glu Leu Gln Leu Pro Thr Val Trp Arg Glu Asn Ser
                245                 250                 255

Gly Ser Tyr Trp Cys Gly Ala Glu Thr Val Arg Gly Asn Ile His Lys
            260                 265                 270

His Ser Pro Ser Leu Gln Ile His Val Gln Arg Ile Pro Val Ser Gly
        275                 280                 285

Val Leu Leu Glu Thr Gln Pro Ser Gly Gly Gln Ala Val Glu Gly Glu
290                 295                 300

Met Leu Val Leu Val Cys Ser Val Ala Glu Gly Thr Gly Asp Thr Thr
305                 310                 315                 320

Phe Ser Trp His Arg Glu Asp Met Gln Glu Ser Leu Gly Arg Lys Thr
                325                 330                 335

Gln Arg Ser Leu Arg Ala Glu Leu Glu Leu Pro Ala Ile Arg Gln Ser
            340                 345                 350

His Ala Gly Gly Tyr Tyr Cys Thr Ala Asp Asn Ser Tyr Gly Pro Val
        355                 360                 365

Gln Ser Met Val Leu Asn Val Thr Val Arg Glu Thr Pro Gly Asn Arg
370                 375                 380

Asp Gly Leu Val Ala Ala Gly Ala Thr Gly Gly Leu Leu Ser Ala Leu
385                 390                 395                 400

Leu Leu Ala Val Ala Leu Leu Phe His Cys Trp Arg Arg Arg Lys Ser
                405                 410                 415

Gly Val Gly Phe Leu Gly Asp Glu Thr Arg Leu Pro Pro Ala Pro Gly
            420                 425                 430

Pro Gly Glu Ser Ser His Ser Ile Cys Pro Ala Gln Val Glu Leu Gln
        435                 440                 445

Ser Leu Tyr Val Asp Val His Pro Lys Lys Gly Asp Leu Val Tyr Ser
450                 455                 460

Glu Ile Gln Thr Thr Gln Leu Gly Glu Glu Glu Ala Asn Thr Ser
465                 470                 475                 480

Arg Thr Leu Leu Glu Asp Lys Asp Val Ser Val Val Tyr Ser Glu Val
```

```
                       485                 490                 495
Lys Thr Gln His Pro Asp Asn Ser Ala Gly Lys Ile Ser Ser Lys Asp
                   500                 505                 510

Glu Glu Ser
        515

<210> SEQ ID NO 15
<211> LENGTH: 734
<212> TYPE: PRT
<213> ORGANISM: Homo sapiens

<400> SEQUENCE: 15

Met Leu Leu Trp Leu Leu Leu Ile Leu Thr Pro Gly Arg Glu Gln
1               5                   10                  15

Ser Gly Val Ala Pro Lys Ala Val Leu Leu Asn Pro Pro Trp Ser
                20                  25                  30

Thr Ala Phe Lys Gly Glu Lys Val Ala Leu Ile Cys Ser Ser Ile Ser
                35                  40                  45

His Ser Leu Ala Gln Gly Asp Thr Tyr Trp Tyr His Asp Glu Lys Leu
    50                  55                  60

Leu Lys Ile Lys His Asp Lys Ile Gln Ile Thr Glu Pro Gly Asn Tyr
65                  70                  75                  80

Gln Cys Lys Thr Arg Gly Ser Ser Leu Ser Asp Ala Val His Val Glu
                85                  90                  95

Phe Ser Pro Asp Trp Leu Ile Leu Gln Ala Leu His Pro Val Phe Glu
                100                 105                 110

Gly Asp Asn Val Ile Leu Arg Cys Gln Gly Lys Asp Asn Lys Asn Thr
                115                 120                 125

His Gln Lys Val Tyr Tyr Lys Asp Gly Lys Gln Leu Pro Asn Ser Tyr
    130                 135                 140

Asn Leu Glu Lys Ile Thr Val Asn Ser Val Ser Arg Asp Asn Ser Lys
145                 150                 155                 160

Tyr His Cys Thr Ala Tyr Arg Lys Phe Tyr Ile Leu Asp Ile Glu Val
                165                 170                 175

Thr Ser Lys Pro Leu Asn Ile Gln Val Gln Glu Leu Phe Leu His Pro
                180                 185                 190

Val Leu Arg Ala Ser Ser Thr Pro Ile Glu Gly Ser Pro Met Thr
    195                 200                 205

Leu Thr Cys Glu Thr Gln Leu Ser Pro Gln Arg Pro Asp Val Gln Leu
    210                 215                 220

Gln Phe Ser Leu Phe Arg Asp Ser Gln Thr Leu Gly Leu Gly Trp Ser
225                 230                 235                 240

Arg Ser Pro Arg Leu Gln Ile Pro Ala Met Trp Thr Glu Asp Ser Gly
                245                 250                 255

Ser Tyr Trp Cys Glu Val Glu Thr Val Thr His Ser Ile Lys Lys Arg
                260                 265                 270

Ser Leu Arg Ser Gln Ile Arg Val Gln Arg Val Pro Val Ser Asn Val
    275                 280                 285

Asn Leu Glu Ile Arg Pro Thr Gly Gly Gln Leu Ile Glu Gly Glu Asn
    290                 295                 300

Met Val Leu Ile Cys Ser Val Ala Gln Gly Ser Gly Thr Val Thr Phe
305                 310                 315                 320

Ser Trp His Lys Glu Gly Arg Val Arg Ser Leu Gly Arg Lys Thr Gln
                325                 330                 335

Arg Ser Leu Leu Ala Glu Leu His Val Leu Thr Val Lys Glu Ser Asp
```

-continued

```
                    340                 345                 350
Ala Gly Arg Tyr Tyr Cys Ala Ala Asp Asn Val His Ser Pro Ile Leu
            355                 360                 365

Ser Thr Trp Ile Arg Val Thr Val Arg Ile Pro Val Ser His Pro Val
        370                 375                 380

Leu Thr Phe Arg Ala Pro Arg Ala His Thr Val Val Gly Asp Leu Leu
385                 390                 395                 400

Glu Leu His Cys Glu Ser Leu Arg Gly Ser Pro Pro Ile Leu Tyr Arg
                405                 410                 415

Phe Tyr His Glu Asp Val Thr Leu Gly Asn Ser Ser Ala Pro Ser Gly
            420                 425                 430

Gly Gly Ala Ser Phe Asn Leu Ser Leu Thr Ala Glu His Ser Gly Asn
        435                 440                 445

Tyr Ser Cys Asp Ala Asp Asn Gly Leu Gly Ala Gln His Ser His Gly
    450                 455                 460

Val Ser Leu Arg Val Thr Val Pro Val Ser Arg Pro Val Leu Thr Leu
465                 470                 475                 480

Arg Ala Pro Gly Ala Gln Ala Val Val Gly Asp Leu Leu Glu Leu His
                485                 490                 495

Cys Glu Ser Leu Arg Gly Ser Phe Pro Ile Leu Tyr Trp Phe Tyr His
            500                 505                 510

Glu Asp Asp Thr Leu Gly Asn Ile Ser Ala His Ser Gly Gly Gly Ala
        515                 520                 525

Ser Phe Asn Leu Ser Leu Thr Thr Glu His Ser Gly Asn Tyr Ser Cys
    530                 535                 540

Glu Ala Asp Asn Gly Leu Gly Ala Gln His Ser Lys Val Val Thr Leu
545                 550                 555                 560

Asn Val Thr Gly Thr Ser Arg Asn Arg Thr Gly Leu Thr Ala Ala Gly
                565                 570                 575

Ile Thr Gly Leu Val Leu Ser Ile Leu Val Leu Ala Ala Ala Ala Ala
            580                 585                 590

Leu Leu His Tyr Ala Arg Ala Arg Arg Lys Pro Gly Gly Leu Ser Ala
        595                 600                 605

Thr Gly Thr Ser Ser His Ser Pro Ser Glu Cys Gln Glu Pro Ser Ser
    610                 615                 620

Ser Arg Pro Ser Arg Ile Asp Pro Gln Glu Pro Thr His Ser Lys Pro
625                 630                 635                 640

Leu Ala Pro Met Glu Leu Glu Pro Met Tyr Ser Asn Val Asn Pro Gly
                645                 650                 655

Asp Ser Asn Pro Ile Tyr Ser Gln Ile Trp Ser Ile Gln His Thr Lys
            660                 665                 670

Glu Asn Ser Ala Asn Cys Pro Met Met His Gln Glu His Glu Glu Leu
        675                 680                 685

Thr Val Leu Tyr Ser Glu Leu Lys Lys Thr His Pro Asp Asp Ser Ala
    690                 695                 700

Gly Glu Ala Ser Ser Arg Gly Arg Ala His Glu Glu Asp Asp Glu Glu
705                 710                 715                 720

Asn Tyr Glu Asn Val Pro Arg Val Leu Leu Ala Ser Asp His
                725                 730

<210> SEQ ID NO 16
<211> LENGTH: 508
<212> TYPE: PRT
<213> ORGANISM: Homo sapiens
```

<400> SEQUENCE: 16

Met Leu Leu Trp Ser Leu Leu Val Ile Phe Asp Ala Val Thr Glu Gln
1               5                   10                  15

Ala Asp Ser Leu Thr Leu Val Ala Pro Ser Ser Val Phe Glu Gly Asp
            20                  25                  30

Ser Ile Val Leu Lys Cys Gln Gly Glu Gln Asn Trp Lys Ile Gln Lys
        35                  40                  45

Met Ala Tyr His Lys Asp Asn Lys Glu Leu Ser Val Phe Lys Lys Phe
50                  55                  60

Ser Asp Phe Leu Ile Gln Ser Ala Val Leu Ser Asp Ser Gly Asn Tyr
65                  70                  75                  80

Phe Cys Ser Thr Lys Gly Gln Leu Phe Leu Trp Asp Lys Thr Ser Asn
                85                  90                  95

Ile Val Lys Ile Lys Val Gln Glu Leu Phe Gln Arg Pro Val Leu Thr
            100                 105                 110

Ala Ser Ser Phe Gln Pro Ile Glu Gly Gly Pro Val Ser Leu Lys Cys
        115                 120                 125

Glu Thr Arg Leu Ser Pro Gln Arg Leu Asp Val Gln Leu Gln Phe Cys
130                 135                 140

Phe Phe Arg Glu Asn Gln Val Leu Gly Ser Gly Trp Ser Ser Ser Pro
145                 150                 155                 160

Glu Leu Gln Ile Ser Ala Val Trp Ser Glu Asp Thr Gly Ser Tyr Trp
                165                 170                 175

Cys Lys Ala Glu Thr Val Thr His Arg Ile Arg Lys Gln Ser Leu Gln
            180                 185                 190

Ser Gln Ile His Val Gln Arg Ile Pro Ile Ser Asn Val Ser Leu Glu
        195                 200                 205

Ile Arg Ala Pro Gly Gly Gln Val Thr Glu Gly Gln Lys Leu Ile Leu
210                 215                 220

Leu Cys Ser Val Ala Gly Gly Thr Gly Asn Val Thr Phe Ser Trp Tyr
225                 230                 235                 240

Arg Glu Ala Thr Gly Thr Ser Met Gly Lys Lys Thr Gln Arg Ser Leu
                245                 250                 255

Ser Ala Glu Leu Glu Ile Pro Ala Val Lys Glu Ser Asp Ala Gly Lys
            260                 265                 270

Tyr Tyr Cys Arg Ala Asp Asn Gly His Val Pro Ile Gln Ser Lys Val
        275                 280                 285

Val Asn Ile Pro Val Arg Ile Pro Val Ser Arg Pro Val Leu Thr Leu
290                 295                 300

Arg Ser Pro Gly Ala Gln Ala Ala Val Gly Asp Leu Leu Glu Leu His
305                 310                 315                 320

Cys Glu Ala Leu Arg Gly Ser Pro Pro Ile Leu Tyr Gln Phe Tyr His
                325                 330                 335

Glu Asp Val Thr Leu Gly Asn Ser Ser Ala Pro Ser Gly Gly Gly Ala
            340                 345                 350

Ser Phe Asn Leu Ser Leu Thr Ala Glu His Ser Gly Asn Tyr Ser Cys
        355                 360                 365

Glu Ala Asn Asn Gly Leu Gly Ala Gln Cys Ser Glu Ala Val Pro Val
370                 375                 380

Ser Ile Ser Gly Pro Asp Gly Tyr Arg Arg Asp Leu Met Thr Ala Gly
385                 390                 395                 400

Val Leu Trp Gly Leu Phe Gly Val Leu Gly Phe Thr Gly Val Ala Leu
                405                 410                 415

```
Leu Leu Tyr Ala Leu Phe His Lys Ile Ser Gly Glu Ser Ser Ala Thr
            420                 425                 430

Asn Glu Pro Arg Gly Ala Ser Arg Pro Asn Pro Gln Glu Phe Thr Tyr
            435                 440                 445

Ser Ser Pro Thr Pro Asp Met Glu Glu Leu Gln Pro Val Tyr Val Asn
        450                 455                 460

Val Gly Ser Val Asp Val Asp Val Val Tyr Ser Gln Val Trp Ser Met
465                 470                 475                 480

Gln Gln Pro Glu Ser Ser Ala Asn Ile Arg Thr Leu Leu Glu Asn Lys
                485                 490                 495

Asp Ser Gln Val Ile Tyr Ser Ser Val Lys Lys Ser
            500                 505

<210> SEQ ID NO 17
<211> LENGTH: 429
<212> TYPE: PRT
<213> ORGANISM: Homo sapiens

<400> SEQUENCE: 17

Met Leu Pro Arg Leu Leu Leu Ile Cys Ala Pro Leu Cys Glu Pro
1               5                   10                  15

Ala Glu Leu Phe Leu Ile Ala Ser Pro Ser His Pro Thr Glu Gly Ser
            20                  25                  30

Pro Val Thr Leu Thr Cys Lys Met Pro Phe Leu Gln Ser Ser Asp Ala
        35                  40                  45

Gln Phe Gln Phe Cys Phe Phe Arg Asp Thr Arg Ala Leu Gly Pro Gly
    50                  55                  60

Trp Ser Ser Ser Pro Lys Leu Gln Ile Ala Ala Met Trp Lys Glu Asp
65              70                  75                  80

Thr Gly Ser Tyr Trp Cys Glu Ala Gln Thr Met Ala Ser Lys Val Leu
                85                  90                  95

Arg Ser Arg Arg Ser Gln Ile Asn Val His Arg Val Pro Val Ala Asp
            100                 105                 110

Val Ser Leu Glu Thr Gln Pro Pro Gly Gly Gln Val Met Glu Gly Asp
        115                 120                 125

Arg Leu Val Leu Ile Cys Ser Val Ala Met Gly Thr Gly Asp Ile Thr
    130                 135                 140

Phe Leu Trp Tyr Lys Gly Ala Val Gly Leu Asn Leu Gln Ser Lys Thr
145                 150                 155                 160

Gln Arg Ser Leu Thr Ala Glu Tyr Glu Ile Pro Ser Val Arg Glu Ser
                165                 170                 175

Asp Ala Glu Gln Tyr Tyr Cys Val Ala Glu Asn Gly Tyr Gly Pro Ser
            180                 185                 190

Pro Ser Gly Leu Val Ser Ile Thr Val Arg Ile Pro Val Ser Arg Pro
        195                 200                 205

Ile Leu Met Leu Arg Ala Pro Arg Ala Gln Ala Val Glu Asp Val
    210                 215                 220

Leu Glu Leu His Cys Glu Ala Leu Arg Gly Ser Pro Pro Ile Leu Tyr
225                 230                 235                 240

Trp Phe Tyr His Glu Asp Ile Thr Leu Gly Ser Arg Ser Ala Pro Ser
                245                 250                 255

Gly Gly Gly Ala Ser Phe Asn Leu Ser Leu Thr Glu Glu His Ser Gly
            260                 265                 270

Asn Tyr Ser Cys Glu Ala Asn Asn Gly Leu Gly Ala Gln Arg Ser Glu
        275                 280                 285
```

```
Ala Val Thr Leu Asn Phe Thr Val Pro Thr Gly Ala Arg Ser Asn His
            290                 295                 300
Leu Thr Ser Gly Val Ile Glu Gly Leu Leu Ser Thr Leu Gly Pro Ala
305                 310                 315                 320
Thr Val Ala Leu Leu Phe Cys Tyr Gly Leu Lys Arg Lys Ile Gly Arg
                    325                 330                 335
Arg Ser Ala Arg Asp Pro Leu Arg Ser Leu Pro Ser Pro Leu Pro Gln
            340                 345                 350
Glu Phe Thr Tyr Leu Asn Ser Pro Thr Pro Gly Gln Leu Gln Pro Ile
                355                 360                 365
Tyr Glu Asn Val Asn Val Val Ser Gly Asp Val Tyr Ser Leu Ala
            370                 375                 380
Tyr Tyr Asn Gln Pro Glu Gln Glu Ser Val Ala Ala Glu Thr Leu Gly
385                 390                 395                 400
Thr His Met Glu Asp Lys Val Ser Leu Asp Ile Tyr Ser Arg Leu Arg
                    405                 410                 415
Lys Ala Asn Ile Thr Asp Val Asp Tyr Glu Asp Ala Met
            420                 425

<210> SEQ ID NO 18
<211> LENGTH: 613
<212> TYPE: PRT
<213> ORGANISM: Pseudomonas sp.

<400> SEQUENCE: 18

Ala Glu Glu Ala Phe Asp Leu Trp Asn Glu Cys Ala Lys Ala Cys Val
1               5                   10                  15
Leu Asp Leu Lys Asp Gly Val Arg Ser Ser Arg Met Ser Val Asp Pro
            20                  25                  30
Ala Ile Ala Asp Thr Asn Gly Gln Gly Val Leu His Tyr Ser Met Val
                35                  40                  45
Leu Glu Gly Gly Asn Asp Ala Leu Lys Leu Ala Ile Asp Asn Ala Leu
            50                  55                  60
Ser Ile Thr Ser Asp Gly Leu Thr Ile Arg Leu Glu Gly Gly Val Glu
65                  70                  75                  80
Pro Asn Lys Pro Val Arg Tyr Ser Tyr Thr Arg Gln Ala Arg Gly Ser
                85                  90                  95
Trp Ser Leu Asn Trp Leu Val Pro Ile Gly His Glu Lys Pro Ser Asn
            100                 105                 110
Ile Lys Val Phe Ile His Glu Leu Asn Ala Gly Asn Gln Leu Ser His
                115                 120                 125
Met Ser Pro Ile Tyr Thr Ile Glu Met Gly Asp Glu Leu Leu Ala Lys
130                 135                 140
Leu Ala Arg Asp Ala Thr Phe Phe Val Arg Ala His Glu Ser Asn Glu
145                 150                 155                 160
Met Gln Pro Thr Leu Ala Ile Ser His Ala Gly Val Ser Val Val Met
                165                 170                 175
Ala Gln Thr Gln Pro Arg Arg Glu Lys Arg Trp Ser Glu Trp Ala Ser
            180                 185                 190
Gly Lys Val Leu Cys Leu Leu Asp Pro Leu Asp Gly Val Tyr Asn Tyr
                195                 200                 205
Leu Ala Gln Gln Arg Cys Asn Leu Asp Asp Thr Trp Glu Gly Lys Ile
            210                 215                 220
Tyr Arg Val Leu Ala Gly Asn Pro Ala Lys His Asp Leu Asp Ile Lys
225                 230                 235                 240
```

-continued

```
Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610
```

```
<210> SEQ ID NO 19
<211> LENGTH: 4
<212> TYPE: PRT
<213> ORGANISM: Pseudomonas sp.

<400> SEQUENCE: 19
```

```
Lys Asp Glu Leu
1

<210> SEQ ID NO 20
<211> LENGTH: 4
<212> TYPE: PRT
<213> ORGANISM: Pseudomonas sp.

<400> SEQUENCE: 20

Arg Glu Asp Leu
1

<210> SEQ ID NO 21
<211> LENGTH: 23
<212> TYPE: PRT
<213> ORGANISM: Homo sapiens

<400> SEQUENCE: 21

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 22
<211> LENGTH: 14
<212> TYPE: PRT
<213> ORGANISM: Homo sapiens

<400> SEQUENCE: 22

Trp Tyr Gln Gln Lys Pro Gly Gln Pro Pro Leu Leu Ile Tyr
1               5                   10

<210> SEQ ID NO 23
<211> LENGTH: 32
<212> TYPE: PRT
<213> ORGANISM: Homo sapiens

<400> SEQUENCE: 23

Gly Val Pro Asp Arg Pro Phe Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 24
<211> LENGTH: 11
<212> TYPE: PRT
<213> ORGANISM: Homo sapiens

<400> SEQUENCE: 24

Phe Gly Gln Gly Gln Thr Lys Leu Glu Ile Lys
1               5                   10

<210> SEQ ID NO 25
<211> LENGTH: 30
<212> TYPE: PRT
<213> ORGANISM: Homo sapiens

<400> SEQUENCE: 25

Gln Val Gln Leu Val Gln Ser Gly Ala Glu Val Lys Lys Pro Gln Ala
1               5                   10                  15

Ser Val Lys Val Ser Cys Lys Ala Ser Gln Tyr Thr Phe Thr
            20                  25                  30

<210> SEQ ID NO 26
```

```
<211> LENGTH: 14
<212> TYPE: PRT
<213> ORGANISM: Homo sapiens

<400> SEQUENCE: 26

Trp Val Arg Gln Ala Pro Gly Gln Arg Leu Glu Trp Met Gly
1               5                   10

<210> SEQ ID NO 27
<211> LENGTH: 32
<212> TYPE: PRT
<213> ORGANISM: Homo sapiens

<400> SEQUENCE: 27

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 28
<211> LENGTH: 11
<212> TYPE: PRT
<213> ORGANISM: Homo sapiens

<400> SEQUENCE: 28

Trp Gly Gln Gly Thr Leu Val Thr Val Ser Ser
1               5                   10

<210> SEQ ID NO 29
<211> LENGTH: 35
<212> TYPE: DNA
<213> ORGANISM: Artificial
<220> FEATURE:
<223> OTHER INFORMATION: primer

<400> SEQUENCE: 29
ccctgaattc tctgtagtca gtgagaagct gatgg                               35

<210> SEQ ID NO 30
<211> LENGTH: 43
<212> TYPE: DNA
<213> ORGANISM: Artificial
<220> FEATURE:
<223> OTHER INFORMATION: primer

<400> SEQUENCE: 30
cgcggatcca aagccaccat gctgctgtgg gtgatattac tgg                      43

<210> SEQ ID NO 31
<211> LENGTH: 27
<212> TYPE: DNA
<213> ORGANISM: Artificial
<220> FEATURE:
<223> OTHER INFORMATION: primer

<400> SEQUENCE: 31
gaaacccagg aagattctct gcgcact                                        27

<210> SEQ ID NO 32
<211> LENGTH: 37
<212> TYPE: DNA
<213> ORGANISM: Artificial
<220> FEATURE:
<223> OTHER INFORMATION: primer

<400> SEQUENCE: 32
```

-continued

```
atagtttagc ggccgcctgt ggcaaaaggg ccacttc          37

<210> SEQ ID NO 33
<211> LENGTH: 29
<212> TYPE: DNA
<213> ORGANISM: Artificial
<220> FEATURE:
<223> OTHER INFORMATION: primer

<400> SEQUENCE: 33
gacacaatat cactcagtgt tatagttcc                  29

<210> SEQ ID NO 34
<211> LENGTH: 41
<212> TYPE: DNA
<213> ORGANISM: Artificial
<220> FEATURE:
<223> OTHER INFORMATION: primer

<400> SEQUENCE: 34
atagtttagc ggccgctcat ctgtgaggag ctgaggaagc c     41

<210> SEQ ID NO 35
<211> LENGTH: 39
<212> TYPE: DNA
<213> ORGANISM: Artificial
<220> FEATURE:
<223> OTHER INFORMATION: primer

<400> SEQUENCE: 35
cgggatatca aagccaccat gctgctgtgg gcgtccttg       39

<210> SEQ ID NO 36
<211> LENGTH: 44
<212> TYPE: DNA
<213> ORGANISM: Artificial
<220> FEATURE:
<223> OTHER INFORMATION: primer

<400> SEQUENCE: 36
atagtttagc ggccgcttaa ctttcttcat ccttagagct gatc  44

<210> SEQ ID NO 37
<211> LENGTH: 38
<212> TYPE: DNA
<213> ORGANISM: Artificial
<220> FEATURE:
<223> OTHER INFORMATION: primer

<400> SEQUENCE: 37
atagtttagc ggccgccatc tctgttgcct ggggtctc        38

<210> SEQ ID NO 38
<211> LENGTH: 40
<212> TYPE: DNA
<213> ORGANISM: Artificial
<220> FEATURE:
<223> OTHER INFORMATION: primer

<400> SEQUENCE: 38
cgggatatca aagccaccat gcttctgtgg ctgctgctgc      40

<210> SEQ ID NO 39
<211> LENGTH: 41
<212> TYPE: DNA
<213> ORGANISM: Artificial
<220> FEATURE:
```

<223> OTHER INFORMATION: primer

<400> SEQUENCE: 39
atagtttagc ggccgccgcc tgttctgttc ctggaagttc c    41

<210> SEQ ID NO 40
<211> LENGTH: 25
<212> TYPE: DNA
<213> ORGANISM: Artificial
<220> FEATURE:
<223> OTHER INFORMATION: primer

<400> SEQUENCE: 40
gtctcgcccc gtcctcaccc tcagg    25

<210> SEQ ID NO 41
<211> LENGTH: 43
<212> TYPE: DNA
<213> ORGANISM: Artificial
<220> FEATURE:
<223> OTHER INFORMATION: primer

<400> SEQUENCE: 41
atagtttagc ggccgcctag tggtctgagg ccagtaatac acg    43

<210> SEQ ID NO 42
<211> LENGTH: 40
<212> TYPE: DNA
<213> ORGANISM: Artificial
<220> FEATURE:
<223> OTHER INFORMATION: primer

<400> SEQUENCE: 42
cgcggatcca aagccaccat gctgctgtgg tcattgctgg    40

<210> SEQ ID NO 43
<211> LENGTH: 43
<212> TYPE: DNA
<213> ORGANISM: Artificial
<220> FEATURE:
<223> OTHER INFORMATION: primer

<400> SEQUENCE: 43
atagtttagc ggccgccagc tgtcatgagg tctcttctat agc    43

<210> SEQ ID NO 44
<211> LENGTH: 29
<212> TYPE: DNA
<213> ORGANISM: Artificial
<220> FEATURE:
<223> OTHER INFORMATION: primer

<400> SEQUENCE: 44
gactcacagg atcagaaaac agagcctcc    29

<210> SEQ ID NO 45
<211> LENGTH: 41
<212> TYPE: DNA
<213> ORGANISM: Artificial
<220> FEATURE:
<223> OTHER INFORMATION: primer

<400> SEQUENCE: 45
atagtttagc ggccgcttat gatttcttca cagaagagta g    41

<210> SEQ ID NO 46

```
<211> LENGTH: 39
<212> TYPE: DNA
<213> ORGANISM: Artificial
<220> FEATURE:
<223> OTHER INFORMATION: primer

<400> SEQUENCE: 46
cggaattcaa agccaccatg ctgccgaggc tgttgctgt                      39

<210> SEQ ID NO 47
<211> LENGTH: 45
<212> TYPE: DNA
<213> ORGANISM: Artificial
<220> FEATURE:
<223> OTHER INFORMATION: primer

<400> SEQUENCE: 47
atagtttagc ggccgcttac atagcatctt catagtccac atctg               45

<210> SEQ ID NO 48
<211> LENGTH: 41
<212> TYPE: DNA
<213> ORGANISM: Artificial
<220> FEATURE:
<223> OTHER INFORMATION: primer

<400> SEQUENCE: 48
atagtttagc ggccgcctga ggtaagatga ttgcttctgg c                   41

<210> SEQ ID NO 49
<211> LENGTH: 17
<212> TYPE: DNA
<213> ORGANISM: Artificial
<220> FEATURE:
<223> OTHER INFORMATION: primer

<400> SEQUENCE: 49
gcatgggtca gaaggat                                              17

<210> SEQ ID NO 50
<211> LENGTH: 17
<212> TYPE: DNA
<213> ORGANISM: Artificial
<220> FEATURE:
<223> OTHER INFORMATION: primer

<400> SEQUENCE: 50
ccaatggtga tgacctg                                              17

<210> SEQ ID NO 51
<211> LENGTH: 20
<212> TYPE: DNA
<213> ORGANISM: Artificial
<220> FEATURE:
<223> OTHER INFORMATION: primer

<400> SEQUENCE: 51
agcccttcag actcggactc                                           20

<210> SEQ ID NO 52
<211> LENGTH: 18
<212> TYPE: DNA
<213> ORGANISM: Artificial
<220> FEATURE:
<223> OTHER INFORMATION: primer

<400> SEQUENCE: 52
```

-continued

```
tggggcagcc taaatctt                                                18
```

<210> SEQ ID NO 53
<211> LENGTH: 361
<212> TYPE: PRT
<213> ORGANISM: Pseudomonas sp.

<400> SEQUENCE: 53

| | | | | | | | | | | | | | | |
|---|---|---|---|---|---|---|---|---|---|---|---|---|---|---|
| Gly | Gly | Ser | Leu | Ala | Ala | Leu | Thr | Ala | His | Gln | Ala | Cys | His | Leu | Pro |
| 1 | | | | 5 | | | | | 10 | | | | | 15 | |

| Leu | Glu | Thr | Phe | Thr | Arg | His | Arg | Gln | Pro | Arg | Gly | Trp | Glu | Gln | Leu |
|---|---|---|---|---|---|---|---|---|---|---|---|---|---|---|---|
| | | | 20 | | | | 25 | | | | | 30 | | | |

| Glu | Gln | Cys | Gly | Tyr | Pro | Val | Gln | Arg | Leu | Val | Ala | Leu | Tyr | Leu | Ala |
|---|---|---|---|---|---|---|---|---|---|---|---|---|---|---|---|
| | | 35 | | | | | 40 | | | | 45 | | | | |

| Ala | Arg | Leu | Ser | Trp | Asn | Gln | Val | Asp | Gln | Val | Ile | Arg | Asn | Ala | Leu |
|---|---|---|---|---|---|---|---|---|---|---|---|---|---|---|---|
| | 50 | | | | | 55 | | | | | 60 | | | | |

| Ala | Ser | Pro | Gly | Ser | Gly | Gly | Asp | Leu | Gly | Glu | Ala | Ile | Arg | Glu | Gln |
|---|---|---|---|---|---|---|---|---|---|---|---|---|---|---|---|
| 65 | | | | | 70 | | | | | 75 | | | | | 80 |

| Pro | Glu | Gln | Ala | Arg | Leu | Ala | Leu | Thr | Leu | Ala | Ala | Ala | Glu | Ser | Glu |
|---|---|---|---|---|---|---|---|---|---|---|---|---|---|---|---|
| | | | | 85 | | | | | 90 | | | | | 95 | |

| Arg | Phe | Val | Arg | Gln | Gly | Thr | Gly | Asn | Asp | Glu | Ala | Gly | Ala | Ala | Asn |
|---|---|---|---|---|---|---|---|---|---|---|---|---|---|---|---|
| | | | 100 | | | | | 105 | | | | | 110 | | |

| Ala | Asp | Val | Val | Ser | Leu | Thr | Cys | Pro | Val | Ala | Ala | Gly | Glu | Cys | Ala |
|---|---|---|---|---|---|---|---|---|---|---|---|---|---|---|---|
| | | 115 | | | | | 120 | | | | | 125 | | | |

| Gly | Pro | Ala | Asp | Ser | Gly | Asp | Ala | Leu | Leu | Glu | Arg | Asn | Tyr | Pro | Thr |
|---|---|---|---|---|---|---|---|---|---|---|---|---|---|---|---|
| | 130 | | | | | 135 | | | | | 140 | | | | |

| Gly | Ala | Glu | Phe | Leu | Gly | Asp | Gly | Gly | Asp | Val | Ser | Phe | Ser | Thr | Arg |
|---|---|---|---|---|---|---|---|---|---|---|---|---|---|---|---|
| 145 | | | | | 150 | | | | | 155 | | | | | 160 |

| Gly | Thr | Gln | Asn | Trp | Thr | Val | Glu | Arg | Leu | Leu | Gln | Ala | His | Arg | Gln |
|---|---|---|---|---|---|---|---|---|---|---|---|---|---|---|---|
| | | | | 165 | | | | | 170 | | | | | 175 | |

| Leu | Glu | Glu | Arg | Gly | Tyr | Val | Phe | Val | Gly | Tyr | His | Gly | Thr | Phe | Leu |
|---|---|---|---|---|---|---|---|---|---|---|---|---|---|---|---|
| | | | 180 | | | | | 185 | | | | | 190 | | |

| Glu | Ala | Ala | Gln | Ser | Ile | Val | Phe | Gly | Gly | Val | Arg | Ala | Arg | Ser | Gln |
|---|---|---|---|---|---|---|---|---|---|---|---|---|---|---|---|
| | | 195 | | | | | 200 | | | | | 205 | | | |

| Asp | Leu | Asp | Ala | Ile | Trp | Arg | Gly | Phe | Tyr | Ile | Ala | Gly | Asp | Pro | Ala |
|---|---|---|---|---|---|---|---|---|---|---|---|---|---|---|---|
| | 210 | | | | | 215 | | | | | 220 | | | | |

| Leu | Ala | Tyr | Gly | Tyr | Ala | Gln | Asp | Gln | Glu | Pro | Asp | Ala | Arg | Gly | Arg |
|---|---|---|---|---|---|---|---|---|---|---|---|---|---|---|---|
| 225 | | | | | 230 | | | | | 235 | | | | | 240 |

| Ile | Arg | Asn | Gly | Ala | Leu | Leu | Arg | Val | Tyr | Val | Pro | Arg | Ser | Ser | Leu |
|---|---|---|---|---|---|---|---|---|---|---|---|---|---|---|---|
| | | | | 245 | | | | | 250 | | | | | 255 | |

| Pro | Gly | Phe | Tyr | Arg | Thr | Ser | Leu | Thr | Leu | Ala | Ala | Pro | Glu | Ala | Ala |
|---|---|---|---|---|---|---|---|---|---|---|---|---|---|---|---|
| | | | 260 | | | | | 265 | | | | | 270 | | |

| Gly | Glu | Val | Glu | Arg | Leu | Ile | Gly | His | Pro | Leu | Pro | Leu | Arg | Leu | Asp |
|---|---|---|---|---|---|---|---|---|---|---|---|---|---|---|---|
| | | 275 | | | | | 280 | | | | | 285 | | | |

| Ala | Ile | Thr | Gly | Pro | Glu | Glu | Glu | Gly | Gly | Arg | Leu | Glu | Thr | Ile | Leu |
|---|---|---|---|---|---|---|---|---|---|---|---|---|---|---|---|
| | 290 | | | | | 295 | | | | | 300 | | | | |

| Gly | Trp | Pro | Leu | Ala | Glu | Arg | Thr | Val | Val | Ile | Pro | Ser | Ala | Ile | Pro |
|---|---|---|---|---|---|---|---|---|---|---|---|---|---|---|---|
| 305 | | | | | 310 | | | | | 315 | | | | | 320 |

| Thr | Asp | Pro | Arg | Asn | Val | Gly | Gly | Asp | Leu | Asp | Pro | Ser | Ser | Ile | Pro |
|---|---|---|---|---|---|---|---|---|---|---|---|---|---|---|---|
| | | | | 325 | | | | | 330 | | | | | 335 | |

| Asp | Lys | Glu | Gln | Ala | Ile | Ser | Ala | Leu | Pro | Asp | Tyr | Ala | Ser | Gln | Pro |
|---|---|---|---|---|---|---|---|---|---|---|---|---|---|---|---|
| | | | 340 | | | | | 345 | | | | | 350 | | |

| Gly | Lys | Pro | Pro | Arg | Glu | Asp | Leu | Lys |
|---|---|---|---|---|---|---|---|---|
| | | 355 | | | | | 360 | |

```
<210> SEQ ID NO 54
<211> LENGTH: 345
<212> TYPE: PRT
<213> ORGANISM: Pseudomonas sp.

<400> SEQUENCE: 54

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
    50                  55                  60

Ala Ser Pro Gly Ser Gly Gly Asp Leu Gly Glu Ala Ile Arg Glu Gln
65                  70                  75                  80

Pro Glu Gln Ala Arg Leu Ala Leu Thr Leu Ala Ala Glu Ser Glu
                85                  90                  95

Arg Phe Val Arg Gln Gly Thr Gly Asn Asp Glu Ala Gly Ala Ala Asn
            100                 105                 110

Gly Pro Ala Asp Ser Gly Asp Ala Leu Leu Glu Arg Asn Tyr Pro Thr
        115                 120                 125

Gly Ala Glu Phe Leu Gly Asp Gly Gly Asp Val Ser Phe Ser Thr Arg
    130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Gly Val Arg Ala Arg Ser Gln
            180                 185                 190

Asp Leu Asp Ala Ile Trp Arg Gly Phe Tyr Ile Ala Gly Asp Pro Ala
        195                 200                 205

Leu Ala Tyr Gly Tyr Ala Gln Asp Gln Glu Pro Asp Ala Arg Gly Arg
    210                 215                 220

Ile Arg Asn Gly Ala Leu Leu Arg Val Tyr Val Pro Arg Ser Ser Leu
225                 230                 235                 240

Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
            260                 265                 270

Ala Ile Thr Gly Pro Glu Glu Glu Gly Gly Arg Leu Glu Thr Ile Leu
        275                 280                 285

Gly Trp Pro Leu Ala Glu Arg Thr Val Val Ile Pro Ser Ala Ile Pro
    290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Arg Glu Asp Leu Lys
            340                 345

<210> SEQ ID NO 55
<211> LENGTH: 349
<212> TYPE: PRT
<213> ORGANISM: Pseudomonas sp.

<400> SEQUENCE: 55
```

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
50                  55                  60

Ala Ser Pro Gly Ser Gly Asp Leu Gly Glu Ala Ile Arg Glu Gln
65                  70                  75                  80

Pro Glu Gln Ala Arg Leu Ala Leu Thr Leu Ala Ala Glu Ser Glu
                85                  90                  95

Arg Phe Val Arg Gln Gly Thr Gly Asn Asp Glu Ala Gly Ala Ala Asn
            100                 105                 110

Gly Pro Ala Asp Ser Gly Asp Ala Leu Leu Glu Arg Asn Tyr Pro Thr
        115                 120                 125

Gly Ala Glu Phe Leu Gly Asp Gly Asp Val Ser Phe Ser Thr Arg
130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Gly Val Arg Ala Arg Ser Gln
            180                 185                 190

Asp Leu Asp Ala Ile Trp Arg Gly Phe Tyr Ile Ala Gly Asp Pro Ala
        195                 200                 205

Leu Ala Tyr Gly Tyr Ala Gln Asp Gln Glu Pro Asp Ala Arg Gly Arg
210                 215                 220

Ile Arg Asn Gly Ala Leu Leu Arg Val Tyr Val Pro Arg Ser Ser Leu
225                 230                 235                 240

Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
            260                 265                 270

Ala Ile Thr Gly Pro Glu Glu Gly Gly Arg Leu Glu Thr Ile Leu
        275                 280                 285

Gly Trp Pro Leu Ala Glu Arg Thr Val Val Ile Pro Ser Ala Ile Pro
290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Arg Glu Asp Leu Lys Lys Asp Glu Leu
            340                 345

<210> SEQ ID NO 56
<211> LENGTH: 349
<212> TYPE: PRT
<213> ORGANISM: Pseudomonas sp.

<400> SEQUENCE: 56

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

```
Glu Gln Cys Gly Tyr Pro Val Gln Arg Leu Val Ala Leu Tyr Leu Ala
             35                  40                  45

Ala Arg Leu Ser Trp Asn Gln Val Asp Gln Val Ile Arg Asn Ala Leu
 50                  55                  60

Ala Ser Pro Gly Ser Gly Gly Asp Leu Gly Glu Ala Ile Arg Glu Gln
 65                  70                  75                  80

Pro Glu Gln Ala Arg Leu Ala Leu Thr Leu Ala Ala Glu Ser Glu
                 85                  90                  95

Arg Phe Val Arg Gln Gly Thr Gly Asn Asp Glu Ala Gly Ala Ala Asn
                100                 105                 110

Gly Pro Ala Asp Ser Gly Asp Ala Leu Leu Glu Arg Asn Tyr Pro Thr
            115                 120                 125

Gly Ala Glu Phe Leu Gly Asp Gly Gly Asp Val Ser Phe Ser Thr Arg
        130                 135                 140

Gly Thr Gln Asn Trp Thr Val Glu Arg Leu Leu Gln Ala His Arg Gln
145                 150                 155                 160

Leu Glu Glu Arg Gly Tyr Val Phe Val Gly Tyr His Gly Thr Phe Leu
                165                 170                 175

Glu Ala Ala Gln Ser Ile Val Phe Gly Gly Val Arg Ala Arg Ser Gln
            180                 185                 190

Asp Leu Asp Ala Ile Trp Arg Gly Phe Tyr Ile Ala Gly Asp Pro Ala
        195                 200                 205

Leu Ala Tyr Gly Tyr Ala Gln Asp Gln Glu Pro Asp Ala Arg Gly Arg
    210                 215                 220

Ile Arg Asn Gly Ala Leu Leu Arg Val Tyr Val Pro Arg Ser Ser Leu
225                 230                 235                 240

Pro Gly Phe Tyr Arg Thr Ser Leu Thr Leu Ala Ala Pro Glu Ala Ala
                245                 250                 255

Gly Glu Val Glu Arg Leu Ile Gly His Pro Leu Pro Leu Arg Leu Asp
            260                 265                 270

Ala Ile Thr Gly Pro Glu Glu Glu Gly Gly Arg Leu Glu Thr Ile Leu
        275                 280                 285

Gly Trp Pro Leu Ala Glu Arg Thr Val Val Ile Pro Ser Ala Ile Pro
290                 295                 300

Thr Asp Pro Arg Asn Val Gly Gly Asp Leu Asp Pro Ser Ser Ile Pro
305                 310                 315                 320

Asp Lys Glu Gln Ala Ile Ser Ala Leu Pro Asp Tyr Ala Ser Gln Pro
                325                 330                 335

Gly Lys Pro Pro Arg Glu Asp Leu Lys Arg Glu Asp Leu
            340                 345

<210> SEQ ID NO 57
<211> LENGTH: 613
<212> TYPE: PRT
<213> ORGANISM: Pseudomonas sp.

<400> SEQUENCE: 57

Ala Glu Glu Ala Phe Asp Leu Trp Asn Glu Cys Ala Lys Ala Cys Val
1               5                  10                  15

Leu Asp Leu Lys Asp Gly Val Arg Ser Ser Arg Met Ser Val Asp Pro
                20                  25                  30

Ala Ile Ala Asp Thr Asn Gly Gln Gly Val Leu His Tyr Ser Met Val
            35                  40                  45

Leu Glu Gly Gly Asn Asp Ala Leu Glu Leu Ala Ile Asp Asn Ala Leu
        50                  55                  60
```

```
Ser Ile Thr Ser Asp Gly Leu Thr Ile Arg Leu Glu Gly Gly Val Glu
 65                  70                  75                  80

Pro Asn Lys Pro Val Arg Tyr Ser Tyr Thr Arg Gln Ala Arg Gly Ser
                 85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
            115                 120                 125

Met Ser Pro Ile Tyr Thr Ile Glu Met Gly Asp Glu Leu Leu Ala Lys
130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
            195                 200                 205

Leu Ala Gln Gln Arg Cys Asn Leu Asp Asp Thr Trp Glu Gly Lys Ile
210                 215                 220

Tyr Arg Val Leu Ala Gly Asn Pro Ala Lys His Asp Leu Asp Ile Lys
225                 230                 235                 240

Pro Thr Val Ile Ser Glu Glu Leu Glu Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
            275                 280                 285

Tyr Pro Val Gln Arg Leu Val Ala Leu Tyr Leu Ala Ala Arg Leu Ser
290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
            355                 360                 365

Ser Leu Thr Cys Pro Val Ala Ala Gly Glu Cys Ala Gly Pro Ala Asp
370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
            435                 440                 445

Ser Ile Val Phe Gly Gly Val Arg Ala Arg Ser Gln Asp Leu Asp Ala
450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
```

-continued

```
                                485                     490                     495

Ala Leu Leu Arg Val Tyr Val Pro Arg Ser Ser Leu Pro Gly Phe Tyr
            500                     505                 510

Arg Thr Ser Leu Thr Leu Ala Ala Pro Glu Ala Ala Gly Glu Val Glu
            515                 520                 525

Arg Leu Ile Gly His Pro Leu Pro Leu Arg Leu Asp Ala Ile Thr Gly
        530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
        610
```

IRTA2 ANTIBODIES AND METHODS OF USE

CROSS REFERENCE TO RELATED APPLICATIONS

This is the U.S. National Stage of International Application No. PCT/US2005/034444, filed Sep. 22, 2005, which was published in English under PCT Article 21(2), which in turn claims the benefit of U.S. Provisional Application No. 60/615,406, filed Sep. 30, 2004, which is incorporated by reference herein in its entirety.

PRIORITY CLAIM

This claims the benefit of U.S. Provisional Application No. 60/615,406, filed Sep. 30, 2004, which is incorporated by reference herein in its entirety.

FIELD

This relates to the field of immunotherapy, specifically to antibodies that bind immunoglobulin superfamily receptor translocation associated 2 (IRTA2) and their use for the detection and treatment of B cell malignancies.

BACKGROUND

Abnormalities of chromosome 1q21 are common in B cell malignancies, including B cell lymphoma and myeloma, but the genes targeted by these aberrations are largely unknown. Chromosomal abnormalities involving band 1q21-q23 are among the most frequent genetic lesions in both B cell non-Hodgkins lymphoma and multiple myeloma. Among non-Hodgkin's lymphoma subtypes, translocation breakpoints at 1q21-q23, including translocations and duplications, have been reported, often as the single chromosomal abnormality in follicular and diffuse large B cell lymphoma (DLCL) in marginal-zone B cell lymphoma and in Burkitt lymphoma.

By cloning the breakpoints of a t(1:14)(q21:q32) chromosomal translocation in a myeloma cell line, two genes were identified, termed immunoglobulin superfamily receptor translocation associated (IRTA) 1 and IRTA2. IRTA2 is identical to sequences identified as BXMAS1 (Nakayama et al., *Biochm. Biophys. Res. Commun.* 285:830-7, 2001) and FcRH5 (Davis et al., *Proc. Natl. Acad. Sci. USA* 98:9772-7, 2001). Both IRTA1 and IRTA2 are members of a family of related genes, the IRTA.

IRTA2 is a cell surface receptor with homologies to the Fc receptor families. It is normally expressed in mature B cells, and has a different distribution in peripheral lymphoid organs than IRTA1: IRTA1 is expressed in marginal zone B cells, while IRTA2 is also expressed in germinal center centrocytes and in immunoblasts. IRTA2 expression is deregulated in multiple myeloma and Burkitt lymphoma cell lines with 1q21 abnormalities (see Miller et al., *Blood* 99:2662-2669, 2002). The high frequency of involvement of 1q21 structural rearrangements in B cell malignancies suggests that IRTA1 and IRTA2 are critical to the pathogenesis of these diseases (see published PCT Application No. WO 01/38490).

Immunotherapy is a potent new weapon against cancer. Immunotherapy involves evoking an immune response against cancer cells based on their production of target antigens. Immunotherapy based on cell-mediated immune responses involves generating a cell-mediated response to cells that produce particular antigenic determinants, while immunotherapy based on humoral immune responses involves generating specific antibodies to cells that produce particular antigenic determinants. Recombinant toxins are chimeric proteins in which a cell targeting moiety is fused to a toxin (Pastan et al., *Science,* 254:1173-1177, 1991). If the cell targeting moiety is the Fv portion of an antibody, the molecule is termed a recombinant immunotoxin (Chaudhary et al. *Nature,* 339:394-397, 1989). The toxin moiety is genetically altered so that it cannot bind to the toxin receptor present on most normal cells. Recombinant immunotoxins selectively kill cells which are recognized by the antigen binding domain. There remains a need for recombinant toxins which can be used to treat cancer, including B cell malignancies.

SUMMARY

Monoclonal antibodies that specifically bind the extracellular domain of IRTA2 are disclosed herein. In one embodiment, these antibodies do not specifically bind IRTA1, IRTA3, IRTA4, or IRTA5. Antibodies that bind IRTA2 can be conjugated to effector molecules, including detectable labels, radionucleotides, toxins and chemotherapeutic agents. These antibodies are of use to detect B cell malignancies, such as hairy cell leukemia and non-Hodgkin's lymphoma. These antibodies are also of use to treat B cell malignancies that express IRTA2, such as hairy cell leukemia and non-Hodgkin's lymphoma.

The foregoing and other features and advantages will become more apparent from the following detailed description of several embodiments, which proceeds with reference to the accompanying figures.

BRIEF DESCRIPTION OF THE FIGURES

FIG. 2A is a bar graph of the results from an ELISA of anti-IRTA2 MAbs to various Fc-fusion proteins. Each Fc-fusion protein indicated on the top of the column was captured on ELISA plates using secondary antibody (goat anti-human IgG). After washing, 100 ng/50 µl/well of MAbs were added, followed by HRP-labeled goat anti-mouse IgG and TMBZ substrate. The signals in ELISA were normalized for the amounts of each Fc-fusion protein on the plates using HRP-goat anti-human Fc. The controls are MAbs 9E10 (anti-myc tag, IgG1), BerH2 (anti-CD30, IgG1), T408 (anti-CD30, IgG2a), T420 (anti-CD30, IgG2b) and HRP-goat anti-human Fc (1/2400 dilution). FIG. 2B is a set of plots of a FACS analysis of selected anti-IRTA2 MAbs using 293T cells transfected with plasmids coding IRTAs or CD30. Two days after transfection, the cells were harvested and incubated with 200 ng/100 µl of each MAb, followed by PE-conjugated goat anti-mouse IgG F(ab')2. Each panel shows the histogram versus log fluorescence (solid line) with the negative control (shed peak) without 1st antibodies. In the positive control panels, the MAbs cross-reactive to other IRTAs were used. They are F26 (anti-IRTA1 and anti-IRTA2, IgG2b), F109 (anti-IRTA3, IgG2b), F47 (anti-IRTA4, IgG2a), and F69 (anti-IRTA5, IgG2a). BerH2 (anti-CD30, IgG1) was also used. "+" indicates more than 1.5-fold than that of the control; "++" indicates more than 10-fold mean fluorescence intensity than that of the negative control.

FIG. 3A is a digital image showing immunofluorescence by the use of anti-IRTA2 MAb F56. 293T cells that were transfected with IRTA2 or CD30 plasmids were detached, combined in a 1:1 ratio, and seeded into chamber slides. The next day, the cells were fixed with 3.7% formaldehyde and incubated with a mixture of anti-IRTA2 MAb F56 (IgG1) and anti-CD30 MAb Ki-1 (IgG3) at 10 µg/ml. As the secondary reagents, a mixture of Alexa 488-conjugated goat-anti-mouse IgG1 and Alexa 555-conjugated goat-anti-mouse IgG3 was used (1:1000 dilution). Nuclei in the field were stained with DAPI (1 µg/ml). CD30 and F56 (anti-IRTA2) staining were observed with 555 nm filter and 488 nm, respectively. DAPI nuclei staining was detected by 460 nm filter. The merged image was created by a computer. FIG. 3B is a digital image of a Western blot analysis of anti-IRTA2 MAbs. Twenty ng of IRTA2-Fc and CD30-Fc fusion proteins were blotted on each strip after separation on a 4-20% SDS-PAGE gel under reducing conditions. The proteins were probed with 10 µg/ml of each MAb or anti-CD30 MAb BerH-2, followed by alkaline phosphatase anti-mouse IgG. In the left blot, the Fc-fusion proteins were visualized using alkaline phosphatase anti-human Fc. Only the MAbs that reacted to the antigen in the blot (F20 and F25) are shown.

FIG. 4A are plots of the results of FACS analysis of 19 human cell lines derived from hematological malignancies. Each cell was stained with anti-IRTA2 MAb F56 or MAb F119, or control mouse IgG1 or PE-labeled CD19. Some cells lines that are negative for CD19, were stained with other CD markers as indicated in each panel. Each panel shows the histogram versus log fluorescence (solid line) with the negative control (shaded peak) without primary antibodies. Eight out of 19 lines were stained with anti-IRTA2 MAbs, six of which were derived from B-NHL. FIG. 4B is a digital image of a RT-PCR analysis of the cell lines for transmembrane type IRTA2 mRNA expression. Primers in separate exons specific for the transmembrane type of IRTA2 (IRTA2c) and primers for β-actin as the control were used for 26 cycles of PCR reaction with cDNAs of each cell. The cDNAs from the cell lines positive for IRTA2 protein expression in FACS resulted in the expected 432-bp size of IRTA2 and cell lines negative in the FACS showed no band. The actin primers gave the same intensity of PCR product from cDNAs of all cell lines. FIG. 4C is a digital image of a Western blot analysis of selected cell lines. Total cell lysates of the indicated cell lines or purified IRTA2-Fc protein were separated in 4-20% gradient SDS-PAGE gel under reducing condition. The proteins were transferred to a PVDF membrane and probed with F25 anti-IRTA2 MAb. Cell lines positive in the FACS showed the same 150-kDa size of bands as the recombinant IRTA2 expressed in the transfected cells. In contrast, cell lines negative in FACS showed no such bands. FIG. 4D is a table summarizing the IRTA2 expression verified by FACS, RT-PCR, and Western blotting. The IRTA2 expression detected by each method was well correlated with the other methods.

FIG. 5A is a set of plots showing the IRTA2-positive cells detected in the HCL patients were positive for CD20, CD22, and CD103, which are the markers of HCL cells. As shown in the histograms, 27% and 39% of PBMCs of patient #1 and patient #2 expressed IRTA2, respectively, when compared to background staining (shaded peaks). Most of IRTA-cells (red region) were CD22-/CD20- or CD103-/Cd20-(red dot-blot panels), whereas most IRTA+ cells (blue region) expressed both CD22 and CD20 or CD103 and CD20 (blue dot-blot panels). FIG. 5B is a set of plots showing CD20+/CD22+ or CD20+/CD103+ cells in PBMCs from the patient (HCL cells) expressed IRTA2. The cells stained either CD22-FITC/IRTA2-PE/CD20-PerCPCy5.5 or CD103-FITC/IRTA2-PE/CD20-PerCPCy5.5 were gated by CD20+/CD22+ or CD20+/CD103+, respectively (circles). The gated cells were shown in black lines in the histograms with background staining (shaded peaks). The histograms showed significant IRTA2 expression on CD20+/CD22+ or CD20+/CD103+ cells. The IRTA2 staining is inhibited by the presence of IRTA2-Fc antigen (red peak) but not by CD30-Fc (blue peak), indicating that IRTA2 staining is specific.

FIG. 7 is the amino acid sequence of the light chain of the variable regions of F119 (SEQ ID NO: 2), F56 (SEQ ID NO: 4) and F25 (SEQ ID NO: 6). The positions of the complementarity determining regions (CDRs) and the framework regions (FRs) are indicated.

SEQUENCE LISTING

Figure 1:
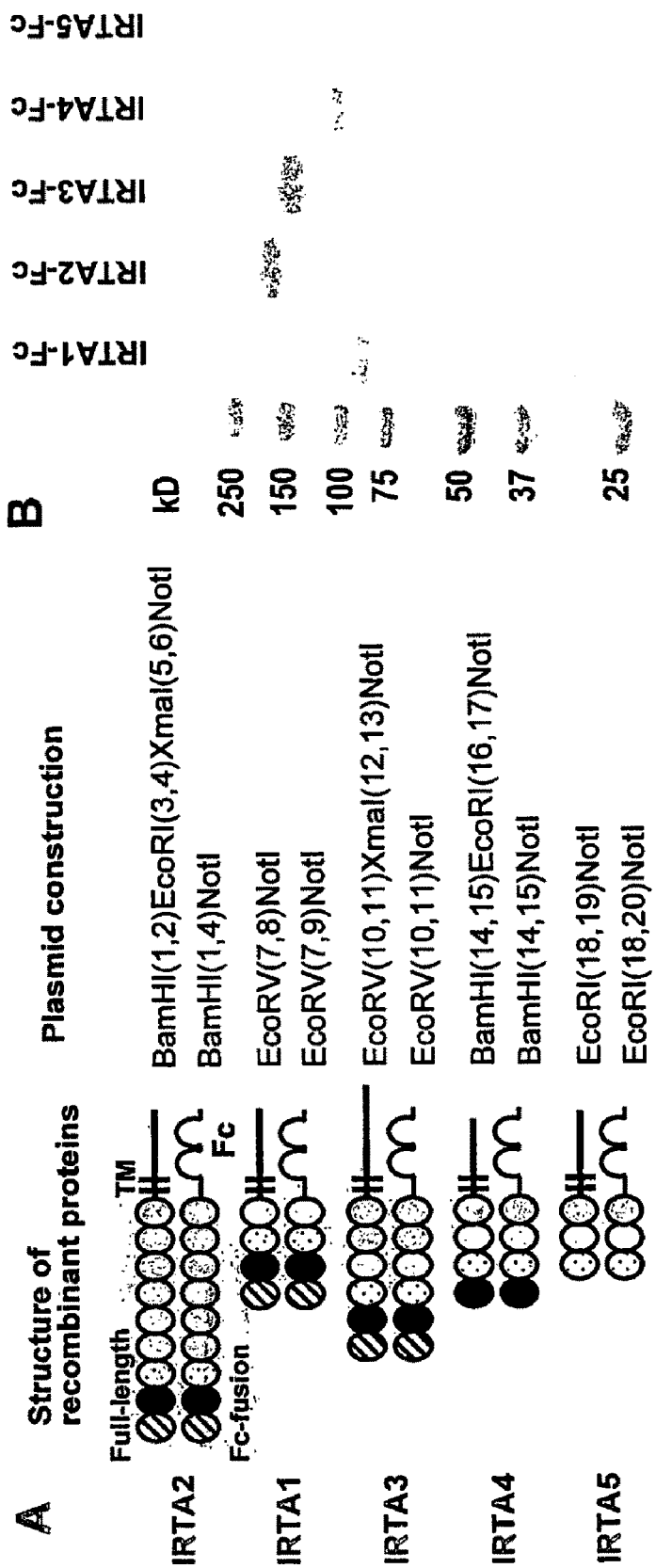
FIG. 1A is a schematic representation of the recombinant IRTA proteins and the plasmids construction. A pair of expression plasmids was generated for each IRTA: one encodes full-length protein under cytomegalovirus (CMV)-promoter of pcDNA3, the other encodes the extracellular domain with human IgG1 Fc as a fusion protein in the same vector. IRTAs possess three to nine immunoglobulin (Ig)-like domains at the extracellular domains shown by circles. They can be classified into four groups based on their homology (Davis et al., *Proc Natl Acad Sci USA* 2001; 98:9772-7; Davis et al., *Immunol Rev* 2002; 190:123-36), which are shown in different patterns of shading of the circles. To construct the plasmids encoding full-length IRTAs, DNA fragments shown as parenthesis with the primer numbers (primers are listed in Table 2) were PCR-amplified from human spleen cDNA or Daudi cells cDNA. They were connected in tandem into pcDNA3 vector using restriction enzymes shown. To make plasmids for Fc-fusion proteins, DNA fragments that code for extracellular domains including their own leader sequences were amplified and inserted into pcDNA3 vector with NotI-XbaI cDNA fragments that code for human Fc.
FIG. 1B is a digital image of an SDS-PAGE of IRTA-Fc fusion proteins. Two µgs of each IRTA-Fc fusion protein was separated on a 4-20% SDS-PAGE gel under reducing conditions. Proteins were visualized with Coomassie-blue staining. Bands of Fc-fusion proteins were seen with expected sizes.

The nucleic and amino acid sequences listed in the accompanying sequence listing are shown using standard letter abbreviations for nucleotide bases, and one letter code for amino acids, as defined in 37 C.F.R. 1.822. Only one strand of each nucleic acid sequence is shown, but the complementary strand is understood as included by any reference to the displayed strand.

SEQ ID NO: 1 is the amino acid sequence of the $V_H$ of F119.

SEQ ID NO: 2 is the amino acid sequence of the $V_L$ of F119.

SEQ ID NO: 3 is the amino acid sequence of the $V_H$ of F56.

SEQ ID NO: 4 is the amino acid sequence of the $V_L$ of F56.

SEQ ID NO: 5 is the amino acid sequence of the $V_H$ of F25.

SEQ ID NO: 6 is the amino acid sequence of the $V_L$ of F25.

SEQ ID NO: 7 is the nucleic acid sequence of a polynucleotide encoding the $V_H$ of F119.

SEQ ID NO: 8 is the nucleic acid sequence of a polynucleotide encoding the $V_L$ of F119.

SEQ ID NO: 9 is the nucleic acid sequence of a polynucleotide encoding the $V_H$ of F56.

SEQ ID NO: 10 is the nucleic acid sequence of a polynucleotide encoding the $V_L$ of F56.

SEQ ID NO: 11 is the nucleic acid sequence of a polynucleotide encoding the $V_H$ of F25.

SEQ ID NO: 12 is the nucleic acid sequence of a polynucleotide encoding the $V_L$ of F25.

SEQ ID NO: 13 is the amino acid sequence of an IRTA2 polypeptide.

SEQ ID NO: 14 is the amino acid sequence of an IRTA1 polypeptide.

SEQ ID NO: 15 is the amino acid sequence of an IRTA3 polypeptide.

SEQ ID NO: 16 is the amino acid sequence of an IRTA4 polypeptide.

SEQ ID NO: 17 is the amino acid sequence of an IRTA5 polypeptide.

SEQ ID NO: 18 is the amino acid sequence of a *Pseudomonas* exotoxin (PE).

SEQ ID NOs: 19-20 are the amino acid sequences of *Pseudomonas* exotoxin (PE) variants.

SEQ ID NOs: 21-28 are the amino acid sequences of exemplary human framework regions.

SEQ ID NOs: 29-52 are the nucleic acid sequences of primers.

SEQ ID NO: 53 is the amino acid sequence of *Pseudomonas* exotoxin (PE) variant PE40.

SEQ ID NO: 54 is the amino acid sequence of *Pseudomonas* exotoxin (PE) variant PE38.

SEQ ID NO: 55 is the amino acid sequence of *Pseudomonas* exotoxin (PE) variant PE38 KDEL.

SEQ ID NO: 56 is the amino acid sequence of *Pseudomonas* exotoxin (PE) variant PE38REDL.

SEQ ID NO: 57 is the amino acid sequence of *Pseudomonas* exotoxin (PE) variant PE4E.

DETAILED DESCRIPTION

I. Abbreviations

| | |
|---|---|
| ALL: | acute lymphocytic leukemia |
| AML: | acute myelogenous leukemia |
| ATCC: | American Type Culture Collection |
| ATL: | adult T cell leukemia |
| CDR: | complementarity determining region |
| CLL: | chronic lymphocytic leukemia |
| CML: | chronic myelogenous leukemia |
| dsFv: | disulfide stabilized fragment of a variable region |
| DLBCL: | diffuse large B-cell lymphoma |
| DT: | diphtheria toxin |
| ELISA: | enzyme-linked immunosorbent assay |
| EM: | effector molecule |
| FACS: | fluorescence activated cell sorter |
| HCL: | hairy cell leukemia |
| HD: | Hodgkin's disease |
| HIV: | human immunodeficiency virus |
| HRP: | horseradish peroxidase |
| IRTA: | immunoglobulin superfamily receptor translocation associated |
| IT: | immunotoxin |
| kDa: | kilodaltons |
| LCDR: | light chain complementarity determining region |
| HCDR: | heavy chain complementarity determining region |
| Ig: | immunoglobulin |
| IRTA2: | immunoglobulin superfamily receptor translocation associated 2 |
| MAb: | monoclonal antibody |
| MCL: | mantle cell lymphoma |
| PE: | *Pseudomonas* exotoxin |
| scFv: | single chain fragment of a variable region |
| TMB: | trimethoxybenzene |
| $V_H$: | variable region of a heavy chain |
| $V_L$: | variable region of a light chain |

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Administration: The introduction of a composition into a subject by a chosen route. For example, if the chosen route is intravenous, the composition is administered by introducing the composition into a vein of the subject.

Amplification: Of a nucleic acid molecule (e.g., a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide ligand comprising at least a light chain or heavy chain immunoglobulin variable region which specifically recognizes and binds an epitope of an antigen, such as IRTA2 or a fragment thereof. This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (e.g., humanized murine antibodies), heteroconjugate antibodies (e.g., bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found.

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized monoclonal antibodies.

A "humanized" immunoglobulin is an immunoglobulin including a human framework region and one or more CDRs from a non-human (such as a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (e.g., see U.S. Pat. No. 5,585,089).

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay. In several examples, a high binding affinity is at least about $1 \times 10^{-8}$ M. In other embodiments, a high binding affinity is at least about $1.5 \times 10^{-8}$, at least about $2.0 \times 10^{-8}$, at least about $2.5 \times 10^{-8}$, at least about $3.0 \times 10^{-8}$, at least about $3.5 \times 10^{-8}$, at least about $4.0 \times 10^{-8}$, at least about $4.5 \times 10^{-8}$, or at least about $5.0 \times 10^{-8}$ M.

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating a lymphoma, leukemia, or another tumor. In one embodiment, a chemotherapeutic agent is a radioactive compound. One of skill in the art can readily identify a chemotherapeutic agent of use (e.g. see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology 2$^{nd}$ ed., ©2000 Churchill Livingstone, Inc; Baltzer, L., Berkery, R. (eds): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody that binds IRTA2 or a fragment thereof used in combination with a radioactive or chemical compound.

Chimeric antibody: An antibody which includes sequences derived from two different antibodies, which typically are of different species. Most typically, chimeric antibodies include human and murine antibody domains, generally human constant regions and murine variable regions, murine CDRs and/or murine SDRs.

Conservative variants: "Conservative" amino acid substitutions are those substitutions that do not substantially affect or decrease an activity or antigenicity of IRTA2. For example, an IRTA2 polypeptide can include at most about 1, at most about 2, at most about 5, and most about 10, or at most about 15 conservative substitutions and specifically bind an antibody that binds the original IRTA polypeptide. The term conservative variation also includes the use of a substituted amino acid in place of an unsubstituted parent amino acid, provided that antibodies raised antibodies raised to the substituted polypeptide also immunoreact with the unsubstituted polypeptide. Non-conservative substitutions are those that reduce an activity or antigenicity.

Complementarity Determining Region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively. By definition, the CDRs of the light chain are bounded by the residues at positions 24 and 34 (L-CDR1), 50 and 56 (L-CDR2), 89 and 97 (L-CDR3); the CDRs of the heavy chain are bounded by the residues at positions 31 and 35b (H-CDR1), 50 and 65 (H-CDR2), 95 and 102 (H-CDR3), using the numbering convention delineated by Kabat et al., (1991) *Sequences of Proteins of Immunological Interest,* $5^{th}$ Edition, U.S. Department of Health and Human Services, Public Health Service, National Institutes of Health, Bethesda, Md. (NIH Publication No. 91-3242).

Contacting: Placement in direct physical association. Includes both in solid and liquid form.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Degenerate variant: A polynucleotide encoding an IRTA2 polypeptide that includes a sequence that is degenerate as a result of the genetic code. There are 20 natural amino acids, most of which are specified by more than one codon. Therefore, all degenerate nucleotide sequences are included as long as the amino acid sequence of the IRTA2 polypeptide encoded by the nucleotide sequence is unchanged.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-IRTA2 antibody, may be an encapsulation system, such as a liposome or micelle that contains a therapeutic composition such as a drug, a nucleic acid (e.g., an antisense nucleic acid), or another therapeutic moiety that can be shielded from direct exposure to the circulatory system. Means of preparing liposomes attached to antibodies are well known to those of skill in the art. See, for example, U.S. Pat. No. 4,957,735; and Connor et al., *Pharm. Ther.* 28:341-365, 1985. Diagnostic agents or moieties include radioisotopes and other detectable labels. Detectable labels useful for such purposes are also well known in the art, and include radioactive isotopes such as $^{32}P$, $^{125}I$, and $^{131}I$, fluorophores, chemiluminescent agents, and enzymes.

Epitope: An antigenic determinant. These are particular chemical groups or peptide sequences on a molecule that are antigenic, i.e. that elicit a specific immune response. An antibody specifically binds a particular antigenic epitope on a polypeptide.

Expressed: Translation of a nucleic acid into a protein. Proteins may be expressed and remain intracellular, become a component of the cell surface membrane, or be secreted into the extracellular matrix or medium Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Framework Region: Amino acid sequences interposed between CDRs. Includes variable light and variable heavy framework regions. The framework regions serve to hold the CDRs in an appropriate orientation for antigen binding.

Hairy Cell Leukemia: A form of chronic leukemia marked by splenomegaly and by an abundance of abnormal large mononuclear cells covered by hair-like villi in the bone marrow, spleen, liver, and peripheral blood. Hairy cell leukemia is also called leukemic reticuloendotheliosis.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

Immunoconjugate: A covalent linkage of an effector molecule to an antibody. The effector molecule can be a detectable label or an immunotoxin. Specific, non-limiting examples of toxins include, but are not limited to, abrin, ricin, Pseudomonas exotoxin (PE, such as PE35, PE37, PE38, and PE40), diphtheria toxin (IT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (e.g., domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule (EM). In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule.

Immunogenic peptide: A peptide which comprises an allele-specific motif or other sequence, such as an N-terminal repeat, such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide. In one specific non-limiting example, an immunogenic polypeptide includes a region of IRTA2, or a fragment thereof, wherein the polypeptide that is expressed on the cell surface of a host cell that expresses the full-length IRTA2 polypeptide.

Immunogenic composition: A composition comprising an IRTA2 polypeptide that induces a measurable CTL response against cells expressing IRTA2 polypeptide, or induces a measurable B cell response (e.g. production of antibodies) against an IRTA2 polypeptide. It further refers to isolated nucleic acids encoding an IRTA2 polypeptide that can be used to express the IRTA2 polypeptide (and thus be used to elicit an immune response against this polypeptide). For in vitro use, the immunogenic composition may consist of the isolated protein or peptide. For in vivo use, the immunogenic composition will typically comprise the protein or peptide in pharmaceutically acceptable carriers, and/or other agents. Any particular peptide, such as an IRTA2 polypeptide, or nucleic acid encoding the polypeptide, can be readily tested for its ability to induce a CTL or B cell response by art-recognized assays. Immunogenic compositions can include adjuvants, which are well known to one of skill in the art.

Immunologically reactive conditions: Includes reference to conditions which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Inhibiting or treating a disease: Inhibiting the full development of a disease or condition, for example, in a subject who is at risk for a disease such as a tumor (for example, a leukemia or a lymphoma). "Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Immunoglobulin superfamily receptor translocation associated (IRTA): A receptor in B cells which binds immunoglobulin and is important in B cell development. There are five types of IRTAs, termed IRTA1, IRTA2, IRTA3, IRTA5 and IRTA5. De-regulation of wild-type IRTA2 perturbs B cell immunological responses and is involved in B cell malignancy. The amino acid sequence of these IRTAs, and nucleic acids encoding IRTA polypeptides are disclosed in published PCT Application No. WO 01/38490, which is incorporated herein by reference.

The cytoplasmic domains of the IRTAs contain consensus immunoreceptor tyrosine-based activation motifs (ITAMs) and/or immunoreceptor tyrosine-based inhibitory motifs (ITIMs). Expression of IRTAs was investigated in human tissues at the RNA level by Northern blot, reverse transcriptase-polymerase chain reaction (RT-PCR) and by in situ hybridization; messenger RNAs of IRTAs have been shown to be abundant in lymphoid tissues and each member is differentially expressed by mature B lineage cells in human tonsil (for example, see Hatzivassiliou et al., *Immunity* 14:277-89, 2001).

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes.

Ligand: Any molecule which specifically binds an IRTA2 protein and includes, inter alia, antibodies that specifically bind an IRTA2 protein. In alternative embodiments, the ligand is a protein or a small molecule (one with a molecular weight less than 6 kiloDaltons).

Linker peptide: A peptide within an antibody binding fragment (e.g., Fv fragment) which serves to indirectly bond the variable heavy chain to the variable light chain. "Linker" can also refer to a peptide serving to link a targeting moiety, such as a scFv, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule ("EM"). The linkage can be either by chemical or recombinant means. "Chemical means" refers to a reaction between the antibody moiety and the effector molecule such that there is a covalent bond formed between the two molecules to form one molecule.

Lymphocytes: A type of white blood cell that is involved in the immune defenses of the body. There are two main types of lymphocytes: B cells and T cells.

Mammal: This term includes both human and non-human mammals. Similarly, the term "subject" includes both human and veterinary subjects.

Major Histocompatibility Complex or MHC: Generic designation meant to encompass the histocompatibility antigen systems described in different species, including the human leukocyte antigens ("HLA"). The term "motif" refers to the pattern of residues in a peptide of defined length, usually about 8 to about 11 amino acids, which is recognized by a particular MHC allele. The peptide motifs are typically different for each MHC allele and differ in the pattern of the highly conserved residues and negative binding residues.

Neoplasia and Tumor: The process of abnormal and uncontrolled growth of cells. Neoplasia is one example of a proliferative disorder.

The product of neoplasia is a neoplasm (a tumor), which is an abnormal growth of tissue that results from excessive cell division. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Non-Hodgkin's Lymphoma: A heterogeneous group of malignant lymphomas (a tumor of the lymphoid tissue), the only common feature being an absence of the giant Reed-Sternberg cells characteristic of Hodgkin's disease. These neoplasias arise from the lymphoid components of the immune system, and present a clinical picture broadly similar to that of Hodgkin's disease except the disease is initially more widespread, with the most common manifestation being painless enlargement of one or more peripheral lymph nodes. There have been numerous classifications of the non-Hodgkin's lymphomas; the most recent system is the Revised European American Lymphoma (REAL) Classification.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (http://www.ncbi.nlm.nih.gov/). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Oligonucleotide: A linear polynucleotide sequence of up to about 100 nucleotide bases in length.

Operably linked: A first nucleic acid sequence is operably linked with a second nucleic acid sequence when the first nucleic acid sequence is placed in a functional relationship with the second nucleic acid sequence. For instance, a promoter, such as the IRTA2 promoter, is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any termination codons. These sequences are usually translatable into a peptide.

Peptide: A chain of amino acids of between 3 and 30 amino acids in length. In one embodiment, a peptide is from about 10 to about 25 amino acids in length. In yet another embodiment, a peptide is from about 11 to about 20 amino acids in length. In yet another embodiment, a peptide is about 12 amino acids in length.

An "IRTA2 peptide" is a series of contiguous amino acid residues from an IRTA2 protein, such as a fragment of IRTA2 protein of about 10 to about 25 amino acids in length, such as about 11 to about 20 amino acid in length, such as about 12 consecutive amino acids of an IRTA2 protein. In one example, with respect to immunogenic compositions comprising an IRTA2 peptide, the term further refers to variations of these peptides in which there are conservative substitutions of amino acids, so long as the variations do not alter by more than about 20% (such as no more than about 1%, about 5%, or about 10%) the ability of the peptide to produce a B cell response, or, when bound to a Major Histocompatibility Complex Class I molecule, to activate cytotoxic T lymphocytes against cells expressing wild-type IRTA2 protein. Induction of CTLs using synthetic peptides and CTL cytotoxicity assays are taught in, e.g., U.S. Pat. No. 5,662,907.

"Soluble" forms of IRTA2 are secreted and can bind to the antibodies disclosed herein. Soluble IRTA2 may be, for example, a product resulting from alternative splicing of the IRTA2 gene, or a soluble extracellular domain that has been shed from cell surface-expressed full-length IRTA2.

Peptide modifications: IRTA2 polypeptides include synthetic embodiments of peptides described herein. In addition, analogs (non-peptide organic molecules), derivatives (chemically functionalized peptide molecules obtained starting with the disclosed peptide sequences) and variants (homologs) of these proteins can be utilized in the methods described herein. Each polypeptide is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the IRTA2 peptides to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of an IRTA2 polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press, Buffalo Grove, Ill., pp. 165-174 and *Principles of Pharmacology* Munson (ed.) 1995, Ch. 102, for descriptions of techniques used in CADD. Also included are mimetics prepared using such techniques.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA. An IRTA2 polynucleotide is a nucleic acid encoding an IRTA2 polypeptide.

Polypeptide: Any chain of amino acids, regardless of length or post-translational modification (e.g., glycosylation or phosphorylation). In one embodiment, the polypeptide is IRTA2 polypeptide. A "residue" refers to an amino acid or amino acid mimetic incorporated in a polypeptide by an amide bond or amide bond mimetic. A polypeptide has an amino terminal (N-terminal) end and a carboxy terminal end.

Probes and primers: A probe comprises an isolated nucleic acid attached to a detectable label or reporter molecule. Primers are short nucleic acids, and can be DNA oligonucleotides 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, e.g., by the polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers may be selected that comprise 20, 25, 30, 35, 40, 50 or more consecutive nucleotides.

Promoter: A promoter is an array of nucleic acid control sequences that directs transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Specific, non-limiting examples of promoters include promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Protein purification: The IRTA2 polypeptides disclosed herein can be purified by any of the means known in the art. See, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Selectively hybridize: Hybridization under moderately or highly stringent conditions that excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC versus AT content), and nucleic acid type (e.g., RNA versus DNA) of the hybridizing regions of the nucleic acids can be considered in selecting hybridization conditions. An additional consideration is whether one of the nucleic acids is immobilized, for example, on a filter.

A specific, non-limiting example of progressively higher stringency conditions is as follows: 2×SSC/0.1% SDS at about room temperature (hybridization conditions); 0.2× SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual*, 2nd ed., Vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of an IRTA2 polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds an IRTA2 polypeptide are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of IRTA2 using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus an IRTA2 specific binding agent is an agent that binds substantially to an IRTA2 polypeptide. In one embodiment, the specific binding agent is a monoclonal or polyclonal antibody that specifically binds the IRTA2 polypeptide.

The term "specifically binds" refers, with respect to an antigen such as IRTA2, to the preferential association of an antibody or other ligand, in whole or part, with a cell or tissue bearing that antigen and not to cells or tissues lacking that antigen. It is, of course, recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue bearing the IRTA2 polypeptide as compared to a cell or tissue lacking the polypeptide. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Subject: Living multi-cellular vertebrate organisms, a category that includes both human and veterinary subjects, including human and non-human mammals.

T Cell: A white blood cell critical to the immune response. T cells include, but are not limited to, CD4+ T cells and CD8+ T cells. A CD4+ T lymphocyte is an immune cell that carries a marker on its surface known as "cluster of differentiation 4" (CD4). These cells, also known as helper T cells, help orchestrate the immune response, including antibody responses as well as killer T cell responses. CD8+ T cells carry the "cluster of differentiation 8" (CD8) marker. In one embodiment, CD8 T cells are cytotoxic T lymphocytes. In another embodiment, a CD8 cell is a suppressor T cell.

Targeting moiety: A portion of a chimeric molecule intended to provide the molecule with the ability to bind specifically to the IRTA2 polypeptide. A "ligand" is a targeting molecule specific for the IRTA2 polypeptide and is generally synonymous with "targeting moiety." An antibody is one version of a ligand.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate a tumor. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (e.g., domain Ia of PE or the B chain of DT) and replacing it with a different targeting moiety, such as an antibody.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Monoclonal Antibodies that Bind IRTA2

Antibodies are disclosed herein that bind IRTA2. The immunoglobulin (Ig) superfamily receptor translocation associated 2 (IRTA2) gene is a gene targeted by one of the 1q21 abnormalities that occurs in B cell malignancies (Hatzivassiliou et al., *Immunity* 14:277-89, 2001). This gene has also been identified as BXMAS1 (Nakayama et al., *Biochem Biophys Res Commun* 285:830-7, 2001, herein incorporated by reference) and Fc receptor homolog 5 (FcRH5) (Miller et al., *Blood* 99:2662-9, 2002, herein incorporated by reference).

A series of genes homologous to IRTA2/BXMAS1/FcRH5 have been identified in the same locus of the human genome. A total of five IRTA family members have been identified (for example, see Davis et al., *Immunol Rev* 190:123-36, 2002). These genes, termed immunoglobulin superfamily translocation associated (IRTA) genes code for individual members of the Ig receptor family with three to nine Ig-like extracellular domains.

Monoclonal antibodies are disclosed herein that specifically bind the extracellular domain of IRTA2. In one example, IRTA2 has an amino acid sequence set forth as:

(SEQ ID NO: 13)
MLLWVILLVLAPVSGQFARTPRPIIFLQPPWTTVFQGERVTLTCKGFRFY

SPQKTKWYHRYLGKEILRETPDNILEVQESGEYRCQAQGSPLSSPVHLDF

SSASLILQAPLSVFEGDSVVLRCRAKAEVTLNNTIYKNDNVLAFLNKRTD

FHIPHACLKDNGAYRCTGYKESCCPVSSNTVKIQVQEPFTRPVLRASSFQ

PISGNPVTLTCETQLSLERSDVPLRFRFFRDDQTLGLGWSLSPNFQITAM

WSKDSGFYWCKAATMPHSVISDSPRSWIQVQIPASHPVLTLSPEKALNFE

GTKVTLHCETQEDSLRTLYRFYHEGVPLRHKSVRCERGASISFSLTTENS

GNYYCTADNGLGAKPSKAVSLSVTVPVSHPVLNLSSPEDLIFEGAKVTLH

CEAQRGSLPILYQFHHEDAALERRSANSAGGVAISFSLTAEHSGNYYCTA

DNGFGPQRSKAVSLSITVPVSHPVLTLSSAEALTFEGATVTLHCEVQRGS

PQILYQFYHEDMPLWSSSTPSVGRVSFSFSLTEGHSGNYYCTADNGFGPQ

RSEVVSLFVTVPVSRPILTLRVPRAQAVVGDLLELHCEAPRGSPPILYWF

YHEDVTLGSSSAPSGGEASFNLSLTAEHSGNYSCEANNGLVAQHSDTOSL

SVIVPVSRPILTFRAPRAQAVVGDLLELHCEALRGSSPILYWFYHEDVTL

GKISAPSGGGASFNLSLTTEHSGIYSCEADNGLEAQRSEMVTLKVAGEWA

LPTSSTSEN

Additional examples of IRTA2 are disclosed in published PCT Application No. WO 01/38490, which is incorporated herein by reference.

In one embodiment, the antibodies that bind IRTA2 do not specifically bind IRTA1, IRTA3, IRTA4 or IRTA5, which have the following amino acid sequences:

IRTA 1:
(SEQ ID NO: 14)
```
mllwasllaf apvcgqsaaa hkpvisvhpp wttffkgerv tltcngfgfy atekttwyhr
hywgekltlt pgntlevres glyrcqargs prsnpvrllf ssdslilqap ysvfegdtlv
lrchrrrkek ltavkytwng nilsisnksw dllipqassn nngnyrcigy gdendvfrsn
fkiikiqelf phpelkatds qptegnsvnl scetqlpper sdtplhfnff rdgevilsdw
stypelqlpt vwrensgsyw cgaetvrgni hkhspslqih vqripvsgvl letqpsggqa
vegemlvlvc svaegtgdtt fswhredmqe slgrktqrsl raelelpair qshaggyyct
adnsygpvqs mvlnvtvret pgnrdglvaa gatggllsal llavallfhc wrrrksgvgt
lgdetrlppa pgpgesshsi cpaqvelqsl yvdvhpkkgd lvyseiqttq lgeeeeants
                              rtlledkdvs vvysevktqh pdnsagkiss kdees
```

IRTA3:
(SEQ ID NO: 15)
```
mllwllllil tpgreqsgva pkavlllnpp wstafkgekv alicssishs laqgdtywyh
dekllkikhd kiqitepgny qcktrgssls davhvefspd wlilqalhpv fegdnvilrc
qgkdnknthq kvyykdgkql pnsynlekit vnsvsrdnsk yhctayrkfy ildievtskp
lniqvqelfl hpvlrassst piegsspmtlt cetqlspqrp dvqlqfslfr dsqtlglgws
rsprlqipam wtedsgsywc evetvthsik krslrsqirv qrvpvsnvnl eirptgqqli
egenmvlics vaqgsgtvtf swhkegrvrs lgrktqrsll aelhvltvke sdagryycaa
dnvhspilst wirvtvripv shpvltfrap rahtvvgdll elhceslrgs ppilyrfyhe
dvtlgnssap sgggasfnls ltaehsgnys cdadnglgaq hshgvslrvt vpvsrpvltl
rapgaqavvg dllelhcesl rgsfpilywf yheddtlgni sahsgggasf nlslttehsg
nysceadngl gaqhskvvtl nvtgtsrnrt gltaagitgl vlsilvlaaa aallhyarar
rkpgglsatg tsshspsecq epsssrpsri dpqepthskp lapmelepmy snvnpgdsnp
iysqiwsiqh tkensancpm mhqeheeltv lyselkkthp ddsageassr graheeddee
nyenvprvll asdh
```

IRTA4:
(SEQ ID NO: 16)
```
mllwsllvif davteqadsl tlvapssvfe gdsivlkcqg eqnwkiqkma yhkdnkelsv
fkkfsdfliq savlsdsgny fcstkgqlfl wdktsnivki kvqelfqrpv ltassfqpie
ggpvslkcet rlspqrldvq lqfcffrenq vlgsgwsssp elqisavwse dtgsywckae
tvthrirkqs lqsqihvqri pisnvsleir apggqvtegq klillcsvag gtgnvtfswy
reatgtsmgk ktqrslsael eipavkesda gkyycradng hvpiqskvvn ipvripvsrp
vltlrspgaq aavgdllelh cealrgsppi lyqfyhedvt lgnssapsgg gasfnlslta
ehsgnyscea nnglgaqcse avpvsisgpd gyrrdlmtag vlwglfgvlg ftgvalllya
lfhkisgess atneprgasr pnpqeftyss ptpdmeelqp vyvnvgsvdv dvvysqvwsm
                              qqpessanir tllenkdsqv iyssvkks
```

IRTA5:
(SEQ ID NO: 17)
```
miprililic aplcepaelf liaspshpte gspvtltckm pfiqssdaqf qfcffrdtra
lgpgwssspk lqiaamwked tgsywceaqt maskvlrsrr sqinvhrvpv advsletqpp
ggqvmegdrl vlicsvamgt gditflwykg avglnlqskt qrsltaeyei psvresdaeq
yycvaengyg pspsglvsit vripvsrpil mlrapraqaa vedvlelhce alrgsppily
wfyheditlg srsapsggga sfnlslteeh sgnysceann glgaqrseav tlnftvptga
rsnhltsgvi egllstlgpa tvallfcygl krkigrrsar dplrslpspl pqeftylnsp
tpgqlqpiye nvnvvsgdev yslayynqpe qesvaaetlg thmedkvsld jysrirkani
tdvdyedam.
```

The sequence of these proteins is well known in the art, and are also provided in WO 01/39490, which is incorporated by reference herein. Thus, in one embodiment, the antibodies disclosed herein can be used to differentiate the expression of IRTA2 from IRTA1, IRTA3, IRTA4, and/or IRTA5. In one example, the antibody specifically binds IRTA2, but does not specifically bind IRTA1, IRTA3, IRTA4, and/or IRTA5.

Disclosed herein is the amino acid sequence of several murine monoclonal antibodies. These monoclonal antibodies each include a variable heavy ($V_H$) and a variable light ($V_L$) chain and specifically bind IRTA2. For example, the antibodies can bind IRTA2 with an affinity constant of at least $10^7$ $M^{-1}$, such as at least $10^8$ $M^{-1}$ at least $5 \times 10^8$ $M^{-1}$ or at least $10^9$ $M^{-1}$.

In one embodiment, the antibody is F119, and includes a $V_H$ polypeptide including an amino acid set forth as SEQ ID NO: 1 and a $V_L$ polypeptide including an amino acid sequence set forth as SEQ ID NO: 2. In another embodiment, the monoclonal antibody is F56, and includes a $V_H$ polypeptide including an amino acid set forth as SEQ ID NO: 3 and a $V_L$ polypeptide including an amino acid sequence set forth a SEQ ID NO: 4. In a further embodiment, the monoclonal antibody is F25, and includes a $V_H$ polypeptide including an amino acid set forth as SEQ ID NO: 5 and a $V_L$ polypeptide including an amino acid sequence set forth a SEQ ID NO: 6. The amino acid sequences of the $V_H$ and $V_L$ of F119, F56 and F25 are also set forth in FIG. 6. Functional fragments of these antibodies are also encompassed by this disclosure (see below).

In several embodiments the antibody includes a $V_H$ polypeptide having an amino acid sequence at least about 90% identical, such as at least about 95%, at least about 98%, or at least about 99% identical to the amino acid sequence set forth as SEQ ID NO: 1 and a $V_L$ polypeptide having an amino acid sequence at least about 90% identical, such as at least about 95%, at least about 98%, or at least about 99% identical to the amino acid sequence set forth as SEQ ID NO: 2. In another embodiment, the monoclonal antibody includes a $V_H$ polypeptide having an amino acid sequence at least about 90% identical, such as at least about 95%, at least about 98%, or at least about 99% identical to the amino acid sequence set forth as SEQ ID NO: 3 and a $V_L$ polypeptide having an amino acid sequence at least about 90% identical, such as at least about 95%, at least about 98%, or at least about 99% identical, to the amino acid sequence set forth as set forth a SEQ ID NO: 4. In a further embodiment, the monoclonal antibody includes a $V_H$ polypeptide having an amino acid sequence at least about 90% identical, such as at least about 95%, at least about 98%, or at least about 99% identical, to the amino acid sequence set forth as SEQ ID NO: 5 and a $V_L$ polypeptide including an amino acid sequence at least about 90% identical, such as at least about 95%, at least about 98%, or at least about 99% identical to the amino acid sequence set forth as SEQ ID NO: 6.

In another embodiment, the antibody is F1, which is produced by a hybridoma deposited in accordance with the Budapest Treaty as American Type Culture Collection (ATCC) Deposit No. PTA-7047, deposited in accordance with the Budapest Treaty on Sep. 22, 2005 or is a humanized form thereof. In another embodiment, the antibody is F44, which is produced by a hybridoma deposited as American Type Culture Collection (ATCC) Deposit No. PTA-7046, deposited in accordance with the Budapest Treaty on Sep. 22, 2005, or is a humanized form thereof. In another embodiment, the antibody is F54, which is produced by a hybridoma deposited with American Type Culture Collection (ATCC) Deposit No. PTA-7048, deposited in accordance with the Budapest Treaty on Sep. 22, 2005 or is a humanized form thereof. Hybridoma cells and their progeny that secrete the monoclonal antibodies F1, F44 and F54 are also encompassed by this disclosure.

Variants of these antibodies are also provided, such as those that have $V_H$ or $V_L$ domains that have similar or identical CDRs to antibodies F54, F44 or F1 that specifically bind IRTA2 or an antigenic epitope thereof. The epitopes of IRTA2 that these monoclonal antibodies bind to are disclosed in Table 4. F25 binds to epitope 2, which is located at amino acids 1 to 109 of SEQ ID NO:13, namely,

```
(amino acids 1 to 109 of SEQ ID NO: 1
MLLWVILLVLAPVSGQFARTPRPIIFLQPPWTTVFQGERVTLTCKGFRFY

SPQKTKWYHRYLGKEILRETPDNILEVQESGEYRCQAQGSPLSSPVHLDF

SSASLILQAP.
```

F54 binds to epitope 1, which is located at amino acids 1 to 190 of SEQ ID NO:13, namely

```
(amino acids 1 to 190 of SEQ ID NO: 13)
MLLWVILLVLAPVSGQFARTPRPIIFLQPPWTTVFQGERVTLTCKGFRFYS

PQKTKWYHRYLGKEILRETPDNILEVQESGEYRCQAQGSPLSSPVHLDFSS

ASLILQAPLSVFEGDSVVLRCRAKAEVTLNNTIYKNDNVLAFLNKRTDFHI

PHACLKDNGAYRCTGYKESCCPVSSNTVKIQVQEPFTR.
```

F44 and F119 bind to epitope 3, which is located at amino acids 191 to 286 of SEQ ID NO:13, namely

```
(amino acids 191 to 286 of SEQ ID NO: 1)
PVLRASSFQPISGNPVTLTCETQLSLERSDVPLRFRFFRDDQTLGLGWSL

SPNFQITAMWSKDSGFYWCKAATMPHISVISDSPRSWIQVQIPASH.
```

F56 binds to epitope 11, which is located at amino acids 287 to 565 of SEQ ID NO:13, namely

```
(amino acids 287 to 565 of SEQ ID NO: 13
PVLTLSPEKALNFEGTKVTLHCETQEDSLRTLYRFYHEGVPLRHKSVRCE

RGASISFSLTTENSGNYYCTADNGLGAKPSKAVSLSVTVPVSHPVLNLSS

PEDLIFEGAKVTLHCEAQRGSLPILYQFHHEDAALERRSANSAGGVAISF

SLTAEHSGNYYCTADNGFGPQRSKAVSLSITVPVSHPVLTLSSAEALTFE

GATVTLHCEVQRGSPQILYQFYHEDMPLWSSSTPSVGRVSFSFSLTEGHS

GNYYCTADNGFGPQRSEVVSLFVTVPVSR
```

F1 binds to epitope 5, which is located at amino acids 566 to 746 of SEQ ID NO:13, namely

```
(amino acids 566 to 746 of SEQ ID NO: 13)
PILTLRVPRAQAVVGDLLELHCEAPRGSPPILYWFYHEDVTLGSSSAPSG

GEASFNLSLTAEHSGNYSCEANNGLVAQHSDTISLSVIVPVSRPILTFRA

PRAQAVVGDLLELHCEALRGSSPILYWFYHEDVTLGKISAPSGGGASFNL

SLTTEHSGIYSCEADNGLEAQRSEMVTLKVA
```

Figure 8:
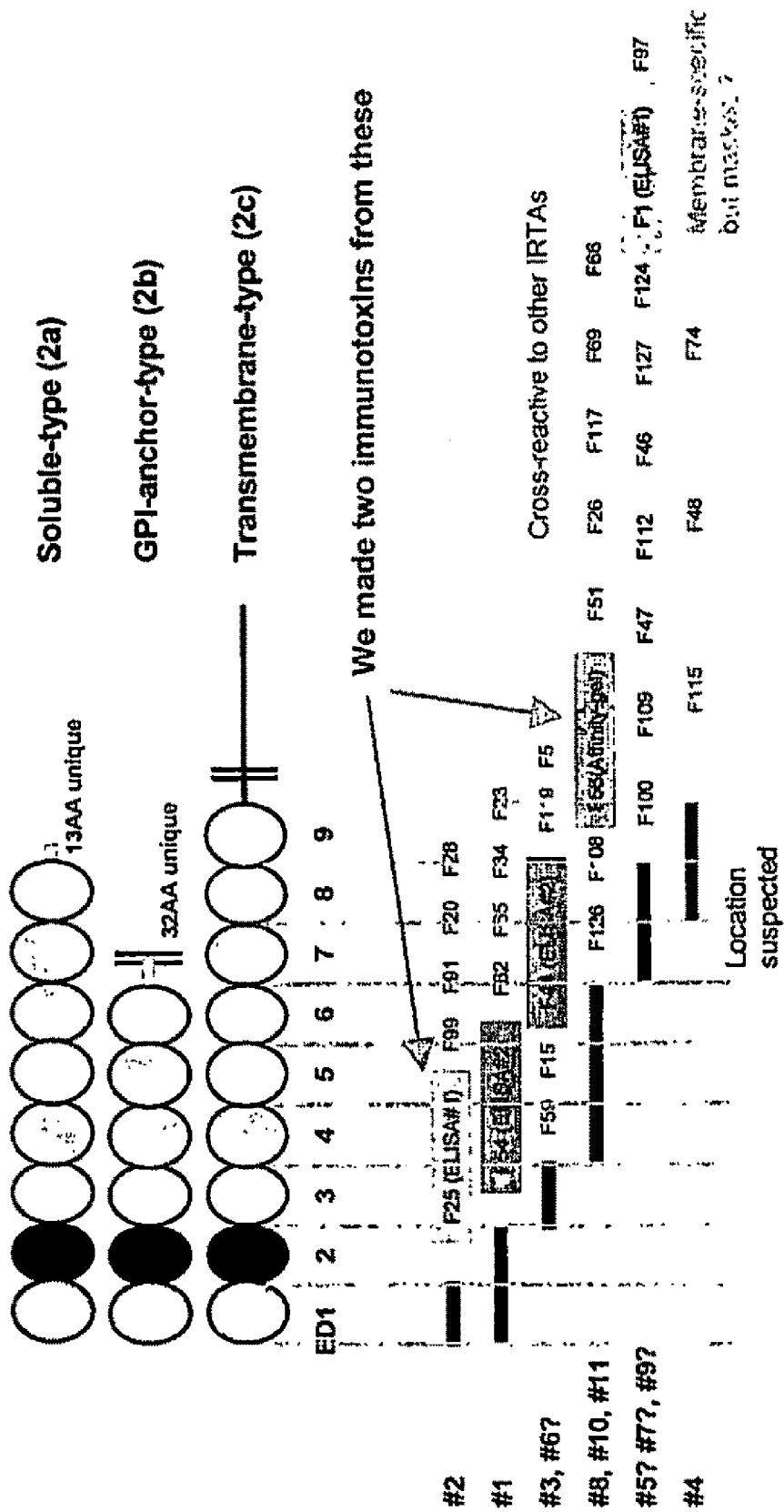
FIG. 8 is a diagram of the epitope locations of anti-IRTA2 monoclonal antibodies. The circles show extracellular domains 1-9 for IRTA2c, and corresponding domains for IRTA2a and IRTA2b. Antibodies that bind the indicated domain are listed.

These epitopes, and the extracellular domains where they are found are also shown in FIG. 8.

In one embodiment, an antibody that binds IRTA2 specifically binds to amino acid residues 1 to 109 of the amino acid sequence set forth as SEQ ID NO:13. In another embodiment, the antibody specifically binds to amino acid residues 1 to 190 of the amino acid sequence set forth as SEQ ID NO:13. In yet another embodiment, the antibody specifically binds to amino acid residues 191 to 286 of the amino acid sequence set forth as SEQ ID NO:13. In yet another embodiment, the antibody specifically binds to amino acid residues 287 to 565 of the amino acid sequence set forth as SEQ ID NO:13. In yet another embodiment, the antibody specifically binds to amino acid residues 566 to 746 of the amino acid sequence set forth as SEQ ID NO:13.

Figure 6:
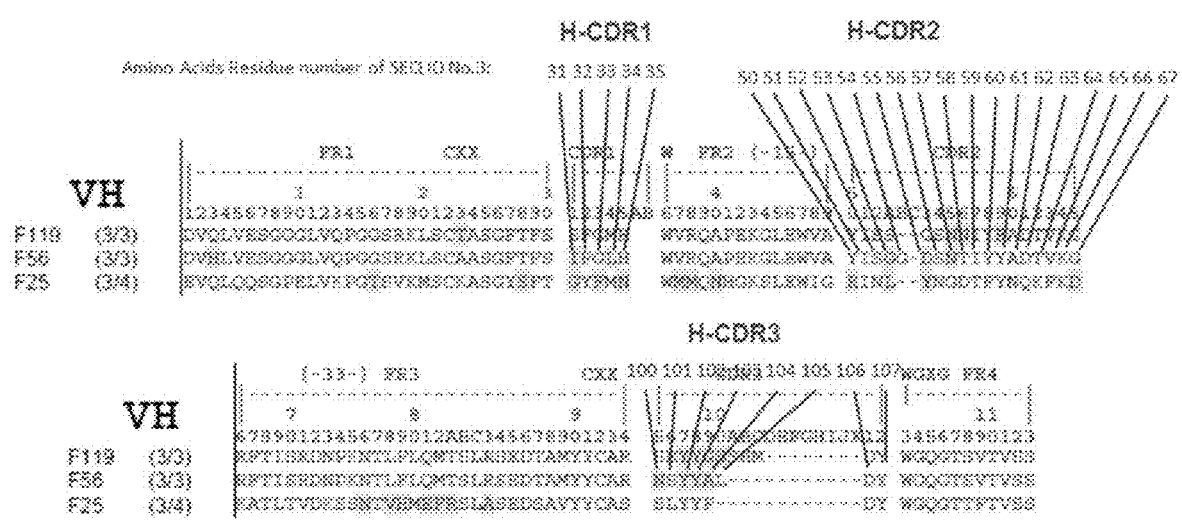
FIG. 6 is the amino acid sequence of the heavy chain of the variable regions of F119 (SEQ ID NO: 1), F56 (SEQ ID NO: 3) and F25 (SEQ ID NO: 5). The positions of the complementarity determining regions (CDRs) and the framework regions (FRs) are indicated.
Figure 7:
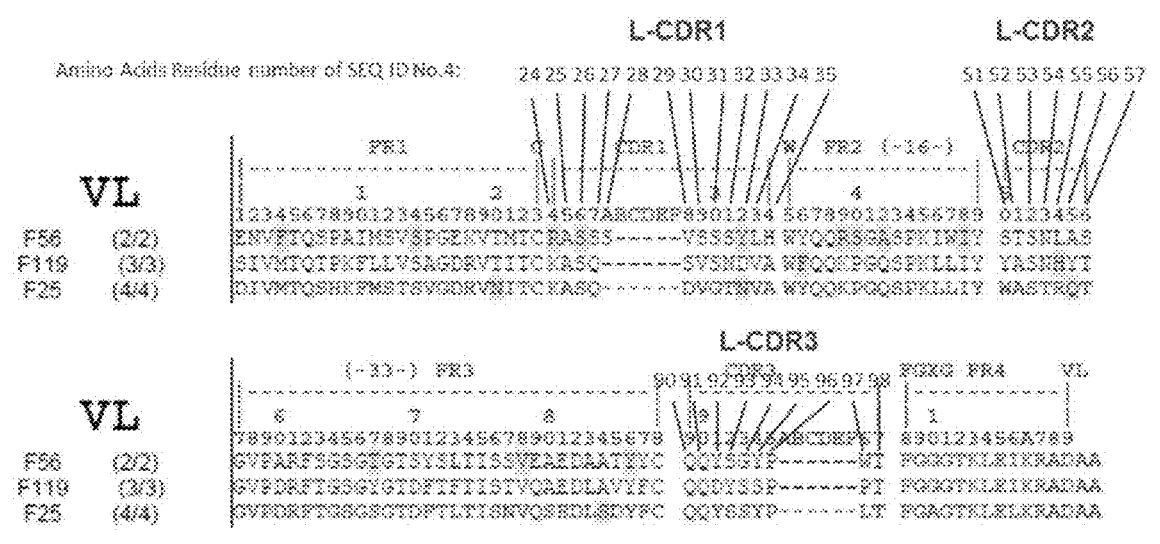

The location of the CDRs (Kabat positioning and location) is further shown in FIGS. 6 and 7. These are set forth as follows:[1]

| Antibody | chain | Sequence |
|---|---|---|
| F119 | $V_H$-CDR1 | Amino acid 31 to 35 of SEQ ID NO: 1 |
| F119 | $V_H$-CDR2 | Amino acid 50 to 65 of SEQ ID NO: 1 |
| F119 | $V_H$-CDR3 | Amino acid 95 to 105 of SEQ ID NO: 1* |
| F119 | $V_L$-CDR1 | Amino acid 24-35 of SEQ ID NO: 2* |
| F119 | $V_L$-CCR2 | Amino acid 51-57 of SEQ ID NO: 2 |
| F119 | $V_L$-CDR3 | Amino acid 90-98 of SEQ ID NO: 2 |
| F56 | $V_H$-CDR1 | Amino acid 31 to 35 of SEQ ID NO: 3 |
| F56 | $V_H$-CDR2 | Amino acid 50 to 65 of SEQ ID NO: 3 |
| F56 | $V_H$-CDR3 | Amino acid 95 to 102 of SEQ ID NO: 3* |
| F56 | $V_L$-CDR1 | Amino acid 24-34 of SEQ ID NO: 4 |
| F56 | $V_L$-CCR2 | Amino acid 50-56 of SEQ ID NO: 4 |
| F56 | $V_L$-CDR3 | Amino acid 89-97 of SEQ ID NO: 4 |
| F25 | $V_H$-CDR1 | Amino acid 31 to 35 of SEQ ID NO: S |
| F25 | $V_H$-CDR2 | Amino acid 50 to 66 of SEQ ID NO: 5 |
| F25 | $V_H$-CDR3 | Amino acid 96 to 101 of SEQ ID NO: 5* |
| F25 | $V_L$-CDR1 | Amino acid 24-34 of SEQ ID NO: 6 |
| F25 | $V_L$-CCR2 | Amino acid 50-56 of SEQ ID NO: 6 |
| F25 | $V_L$-CDR3 | Amino acid 89-97 of SEQ ID NO: 6 |

*numbering slightly different from the numbers shown in FIG. 6 due to presence of additional residues in the alignment (indicated by letters A-F in FIG. 6).

[1] With regard to F56, amino acids 31-35, 50-67 and 100-107 of SEQ ID NO: 3 correspond to the Kabat positioning of the heavy chain CDR1, CDR2 and CDR3 regions, respectively, and amino acids 24-35, 51-57 and 90-98 of SEQ ID NO: 4 correspond to the Kabat positioning of the light chain CDR1, CDR2 and CDR3 regions, respectively.

The production of chimeric antibodies, which include a framework region from one antibody and the CDRs from a different antibody, is well known in the art. For example, humanized antibodies can be routinely produced. The antibody or antibody fragment can be a humanized immunoglobulin having complementarity determining regions (CDRs) from a donor monoclonal antibody that binds IRTA2 (such as those from F1, F44 or F54, produced by the above-described hybridomas deposited with ATCC, or F25, F56 or F119, see the above table) and immunoglobulin and heavy and light chain variable region frameworks from human acceptor immunoglobulin heavy and light chain frameworks. Generally, the humanized immunoglobulin specifically binds to IRTA2 with an affinity constant of at least $10^7$ $M^{-1}$, such as at least $10^8$ $M^{-1}$ at least $5 \times 10^8$ $M^{-1}$ or at least $10^9$ $M^{-1}$.

Humanized monoclonal antibodies can be produced by transferring donor complementarity determining regions (CDRs) from heavy and light variable chains of the donor mouse immunoglobulin (such as F1, F25, F44, F54, F56 or F119) into a human variable domain, and then substituting human residues in the framework regions when required to retain affinity. The use of antibody components derived from humanized monoclonal antibodies obviates potential problems associated with the immunogenicity of the constant regions of the donor antibody. Techniques for producing humanized monoclonal antibodies are described, for example, by Jones et al., *Nature* 321:522, 1986; Riechmann et al., *Nature* 332:323, 1988; Verhoeyen et al., *Science* 239: 1534, 1988; Carter et al., *Proc. Nat'l Acad. Sci. U.S.A.* 89:4285, 1992; Sandhu, *Crit. Rev. Biotech.* 12:437, 1992; and Singer et al., *J. Immunol.* 150:2844, 1993. The antibody may be of any isotype, but in several embodiments the antibody is an IgG, including but not limited to, $IgG_1$, $IgG_2$, $IgG_3$ and $IgG_4$.

In one embodiment, the sequence of the humanized immunoglobulin heavy chain variable region framework can be at least about 65% identical to the sequence of the donor immunoglobulin heavy chain variable region framework. Thus, the sequence of the humanized immunoglobulin heavy chain variable region framework can be at least about 75%, at least about 85%, at least about 99% or at least about 95%, identical to the sequence of the donor immunoglobulin heavy chain variable region framework. Human framework regions, and mutations that can be made in a humanized antibody framework regions, are known in the art (see, for example, in U.S. Pat. No. 5,585,089, which is incorporated herein by reference).

Exemplary human antibodies are LEN and 21/28 CL. The sequences of the heavy and light chain frameworks are known in the art. Exemplary light chain frameworks of human mAb LEN have the following sequences:

```
FR1:
DIVMTQS PDSLAVSLGERATINC          (SEQ ID NO: 21)

FR2:
WYQQKPGQPPLLIY                    (SEQ ID NO: 22)

FR3:
GVPDRPFGSGSGTDFTLTISSLQAEDVAVYYC  (SEQ ID NO: 23)

FR4:
FGQGQTKLETK                       (SEQ ID NO: 24)
```

Exemplary heavy chain frameworks of human mAb 21/28' CL have the following sequences:

```
FR1:
QVQLVQSGAEVKKPQASVKVSCKASQYTFT    (SEQ ID NO: 25)

FR2:
WVRQAIPGQRLEWMG                   (SEQ ID NO: 26)

FR3:
RVTITRDTSASTAYMELSSLRSEDTAVYYCAR  (SEQ ID NO: 27)

FR4:
WGQGTLVTVSS                       (SEQ ID NO: 28).
```

Antibodies, such as murine monoclonal antibodies, chimeric antibodies, and humanized antibodies, include fill length molecules as well as fragments thereof, such as Fab, F(ab')$_2$, and Fv which include a heavy chain and light chain variable region and are capable of binding the epitopic determinant. These antibody fragments retain some ability to selectively bind with their antigen or receptor. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')₂, the fragment of the antibody that can be obtained by treating whole antibody with the enzyme pepsin without subsequent reduction; F(ab')₂ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

Methods of making these fragments are known in the art (see for example, Harlow and Lane, *Antibodies: A Laboratory Manual*, Cold Spring Harbor Laboratory, New York, 1988). In several examples, the variable region included in the immunotoxin is an F1, F54, F44, F119, F56 or F25 Fv, which includes the variable region of the light chain and the variable region of the heavy chain expressed as individual polypeptides. In one group of embodiments, the antibodies have $V_L$ and $V_H$ regions having the amino acid sequences shown above (for example, see SEQ ID NO: 1 and SEQ ID NO: 2; SEQ ID NO; 3 and SEQ ID NO: 4, SEQ ID NO: 5 and SEQ ID NO: 6, or the sequences for $V_L$ and $V_H$ regions for antibodies F1, F44, or F54 (see above). Fv antibodies are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are known in the art (see Whitlow et al., *Methods: a Companion to Methods in Enzymology*, Vol. 2, page 97, 1991; Bird et al., *Science* 242: 423, 1988; U.S. Pat. No. 4,946,778; Pack et al., *Bio/Technology* 11:1271, 1993; and Sandhu, supra).

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')₂. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Thus, one of skill in the art can readily review SEQ ID NOs: 1-6, or the sequences of the F1, F44 and/or F54 antibody, locate one or more of the amino acids in the brief table above, identify a conservative substitution, and produce the conservative variant using well-known molecular techniques.

Effector molecules, such as therapeutic, diagnostic, or detection moieties can be linked to an antibody that specifically binds IRTA2, using any number of means known to those of skill in the art. Both covalent and noncovalent attachment means may be used. The procedure for attaching an effector molecule to an antibody varies according to the chemical structure of the effector. Polypeptides typically contain a variety of functional groups; e.g., carboxylic acid (COOH), free amine (—NH₂) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

In view of the large number of methods that have been reported for attaching a variety of radiodiagnostic compounds, radiotherapeutic compounds, label (e.g. enzymes or fluorescent molecules) drugs, toxins, and other agents to antibodies one skilled in the art will be able to determine a suitable method for attaching a given agent to an antibody or other polypeptide.

Therapeutic agents include various drugs such as vinblastine, daunomycin and the like, and effector molecules such as cytotoxins such as native or modified *Pseudomonas* exotoxin or Diphtheria toxin, encapsulating agents, (e.g., liposomes) which themselves contain pharmacological compositions, target moieties and ligands. The choice of a particular therapeutic agent depends on the particular target molecule or cell and the biological effect desired to be evoked. Thus, for example, the therapeutic agent may be an effector molecule that is cytotoxin which is used to bring about the death of a particular target cell. Conversely, where it is merely desired to invoke a non-lethal biological response, a therapeutic agent can be conjugated to a non-lethal pharmacological agent or a liposome containing a non-lethal pharmacological agent.

Toxins can be employed with antibodies that specifically bind IRTA2 and fragments of these antibodies, such as a svFv or a dsFv, to yield chimeric molecules, which are of use as immunotoxins. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, Mo.).

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, *J. Virol.* 19:220, 1976), and has been used in human clinical trials. See, U.S. Pat. No. 5,792,458 and U.S. Pat. No. 5,208,021. As used herein, the term "diphtheria toxin" refers as appropriate to native diphtheria toxin or to diphtheria toxin that retains enzymatic activity but which has been modified to reduce non-specific toxicity.

Ricin is the lectin RCA60 from *Ricinus communis* (Castor bean). The term "ricin" also references toxic variants thereof. For example, see, U.S. Pat. No. 5,079,163 and U.S. Pat. No. 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, *J. Biochim. Biophys. Acta* 266:543, 1972). The A chain is responsible for inactivating protein synthesis and killing cells. The B chain binds ricin to cell-surface galactose residues and facilitates transport of the A chain into the cytosol (Olsnes et al., *Nature* 249:627-631, 1974 and U.S. Pat. No. 3,060,165).

Ribonucleases have also been conjugated to targeting molecules for use as immunotoxins (see Suzuki et al., *Nat Biotech* 17:265-70, 1999). Exemplary ribotoxins such as α-sarcin and restrictocin are discussed in, e.g., Rathore et al., *Gene* 190: 31-5, 1997; and Goyal and Batra, *Biochem* 345 Pt 2:247-54, 2000. Calicheamicins were first isolated from *Micromonospora echinospora* and are members of the enediyne antitumor antibiotic family that cause double strand breaks in DNA that lead to apoptosis (see, e.g., Lee et al., *J. Antibiot* 42:1070-87. 1989). The drug is the toxic moiety of an immunotoxin in clinical trials (see, e.g., Gillespie et al., *Ann Oncol* 11:73541, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., *Agr. Biol. Chem.* 52:1095, 1988; and Olsnes, *Methods Enzymol.* 50:330-335, 1978).

In one embodiment, the toxin is *Pseudomonas* exotoxin (PE). Native *Pseudomonas* exotoxin A ("PE") is an extremely active monomeric protein (molecular weight 66 kD), secreted by *Pseudomonas aeruginosa*, which inhibits protein synthesis in eukaryotic cells. The native PE sequence and the sequence of modified PE are provided in U.S. Pat. No. 5,602,095, incorporated herein by reference. In one embodiment, native PE has a sequence set forth as:

```
                                                      (SEQ ID NO: 18)
AEEAFDLWNE CAKACVLDLK DGVRSSRMSV DPAIADTNGQ GVLHYSMVLE GGNDALKLAI

DNALSITSDG LTIRLEGGVE PNKPVRYSYT RQARGSWSLN WLVPIGHEKP SNIKVFIHEL

NAGNQLSHMS PIYTIEMGDE LLAKLARDAT FFVRAHESNE MQPTLAISHA GVSVVMAQTQ

PRREKRWSEW ASGKVLCLLD PLDGVYNYLA QQRCNLDDTW EGKIYRVLAG NPAKHDLDIK

PTVISHRLHP PEGGSLAALT AHQACHLPLE TFTRHRQPRG WEQLEQCGYP VQRLVALYLA

ARLSWNQVDQ VIRNALASPG SGGDLGEATR EQPEQARLAL TLAAAESERF VRQGTGNDEA

GAANADVVSL TCPVATGECA GPADSGDALL ERNYPTGAEF LGDGGDVSFS TRGTQNWTVE

RLLQAHRQLE ERGYVFVGYH GTFLEAAQSI VFGGVRARSQ DLDAIWRGFY IAGDPALAYG

YAQDQEPDAR GRIRNGALLR VYVPRSSLPG FYRTSLTLAA PEAAGEVERL IGHPLPLRLD

AITGPEEEGG RLETILGWPL AERTVVIPSA IPTDPRNVGG DLDPSSIPDK EQAISALPDY

ASQPGKPPRE DLK
```

The method of action of PE is inactivation of the ADP-ribosylation of elongation factor 2 (EF-2). The exotoxin contains three structural domains that act in concert to cause cytotoxicity. Domain Ia (amino acids 1-252) mediates cell binding. Domain II (amino acids 253-364) is responsible for translocation into the cytosol and domain III (amino acids 400-613) mediates ADP ribosylation of elongation factor 2. The function of domain Ib (amino acids 365-399) remains undefined, although a large part of it, amino acids 365-380, can be deleted without loss of cytotoxicity. See Siegall et al., *J. Biol. Chem.* 264:14256-14261, 1989.

The term "*Pseudomonas* exotoxin" ("PE") as used herein refers as appropriate to a full-length native (naturally occurring) PE or to a PE that has been modified. Such modifications may include, but are not limited to, elimination of domain Ia, various amino acid deletions in domains Ib, II and III, single amino acid substitutions and the addition of one or more sequences at the carboxyl terminus, such as KDEL (SEQ ID NO: 19) and REDL (SEQ ID NO: 20), see Siegall et al., supra and SEQ ID NO: 55 and SEQ ID NO: 56. In several examples, the cytotoxic fragment of PE retains at least 50%, preferably 75%, more preferably at least 90%, and most preferably 95% of the cytotoxicity of native PE. In one embodiment, the cytotoxic fragment is more toxic than native PE.

Thus, the PE used in the immunotoxins disclosed herein includes the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell (e.g., as a protein or pre-protein). Cytotoxic fragments of PE known in the art include PE40, PE38, and PE35.

In several embodiments, the PE has been modified to reduce or eliminate non-specific cell binding, typically by deleting domain Ia (PE40; SEQ ID NO: 53), as taught in U.S. Pat. No. 4,892,827, although this can also be achieved, for example, by mutating certain residues of domain Ia. U.S. Pat. No. 5,512,658, for instance, discloses that a mutated PE in which Domain Ia is present but in which the basic residues of domain Ia at positions 57, 246, 247, and 249 are replaced with acidic residues (glutamic acid, or "E") exhibits greatly diminished non-specific cytotoxicity. This mutant form of PE is sometimes referred to as PE4E (SEQ ID NO: 57).

PE40 is a truncated derivative of PE (see, Pai et al., *Proc. Nat'l Acad. Sci. USA* 88:3358-62, 1991; and Kondo et al., *J. Biol. Chem.* 263:9470-9475, 1988). PE35 is a 35 kD carboxyl-terminal fragment of PE in which amino acid residues 1-279 have been deleted and the molecule commences with a met at position 280 followed by amino acids 281-364 and 381-613 of native PE. PE35 and PE40 are disclosed, for example, in U.S. Pat. No. 5,602,095 and U.S. Pat. No. 4,892,827.

In some embodiments, the cytotoxic fragment PE38 (SEQ ID NO: 54) is employed. PE38 is a truncated PE pro-protein composed of amino acids 253-364 and 381-613 of SEQ ID NO: 18 which is activated to its cytotoxic form upon processing within a cell (see e.g., U.S. Pat. No. 5,608,039, and Pastan et al., *Biochim. Biophys. Acta* 1333:C1-C6, 1997.

While in some embodiments, the PE is PE4E, PE40, or PE38, any form of PE in which non-specific cytotoxicity has been eliminated or reduced to levels in which significant toxicity to non-targeted cells does not occur can be used in the immunotoxins disclosed herein so long as it remains capable of translocation and EF-2 ribosylation in a targeted cell.

Conservatively modified variants of PE or cytotoxic fragments thereof have at least 80% sequence similarity, preferably at least 85% sequence similarity, more preferably at least 90% sequence similarity, and most preferably at least 95% sequence similarity at the amino acid level, with the PE of interest, such as PE38.

Nucleic acids encoding the amino acid sequences of the antibodies and immunotoxins are provided herein. For example an exemplary nucleic acid sequence encoding the F119 V$_H$ is provided as (SEQ ID NO: 7)
GATGTGCAGCTGGTGGAGTCTGGGGGAGGCTTAGTGCAGCCTGGAGGGTCC

CGGAAACTCTCCTGTACAGCCTCTGGATTCACTTTCAGTAGCTTTGGAATG

CACTGGGTTCGTCAGGCTCCAGAGAAGGGGCTGGAGTGGGTCGCATACATT

AGTAGTGGCAGTAATAACATCTACTTTGCGGACACAGTGAAGGGCCGATTC

ACCATCTCCAGAGACAATCCCAAGAACACCCTGTTCCTGCAAATGACCAGT

CTAAGGTCTGAGGACACGGCCATGTATTACTGTGCAAGATCGGAATACTAC

GGTAGTAGCCATATGGACTACTGGGGTCAAGGAACCTCAGTCACCGTCTCC

TCA, an exemplary nucleic acid sequence encoding F119 V$_L$ is provided as (SEQ ID NO: 8)
AGTATTGTGATGACCCAGACTCCCAAATTCCTGCTTGTATCAGCAGGAGAC

AGGGTTACCATAACCTGCAAGGCCAGTCAGAGTGTGAGTAATGATGTAGCT

TGGTTCCAACAGAAGCCAGGGCAGTCTCCTAAACTGCTGATATACTATGCA

TCCAATCACTACACTGGAGTCCCTGATCGCTTCACTGGCAGTGGATATGGG

ACGGATTTCACTTTCACCATCAGCACTGTGCAGGCTGAAGACCTGGCAGTT

TATTTCTGTCAGCAGGATTATAGCTCTCCTCCGACGTTCGGTGGAGGCACC

AAGCTGGAAATCAAACGGGCTGATGCTGCA, an exemplary nucleic acid sequence encoding the F56 V$_H$ is provided as (SEQ ID NO: 9)
GATGTGCACCTGGTGGAGTCTGGGGGAGGCTTAGTGCAGCCTGGAGGGTCC

CGGAAACTCTCCTGTGCAGCCTCTGGATTCACTTTCAGTATCTTTGGATTG

CACTGGGTTCGTCAGGCTCCAGAGAAGGGGCTGGAGTGGGTCGCATACATT

AGTGGTGACAGTAATACCATCTACTATGCAGACACAGTGAAGGGCCGATTC

ACCATCTCCAGAGACAATCCCAAGAACACCCTGTTCCTGCAAATGACCAGT

CTAAGGTCTGAGGACACGGCCATGTATTACTGTGCAAGAAATAGCTACTAT

GCTCTGGACTACTGGGGTCAAGGAACCTCAGTCACCGTCTCCTCA, an exemplary nucleic acid sequence encoding F56 V$_L$ is provided as (SEQ ID NO: 10)
GAAAATGTGTTCACCCAGTCTCCAGCAATCATGTCTGTATCTCCAGGTGAA

AAGGTCACCATGACCTGCAGGGCCAGCTCAAGTGTCAGTTCCAGTTACTTG

CACTGGTACCAGCAGAGGTCAGGTGCCTCCCCCAAAATCTGGATTTATAGC

ACATCCAACTTGGCTTCTGGAGTCCCTGCTCGCTTCAGTGGCAGTGGGACT

GGGACCTCTTACTCTCTCACAATCAGCAGTGTGGAGGCTGAAGATGCTGCC

-continued

ACTTATTACTGCCAGCAGTACAGTGGTTACCCGTGGACGTTCGGTGGAGGC

ACCAAGTTGGAAATCAAACGGGCTGATGCTGCA, an exemplary nucleic acid sequence encoding the F25 $V_H$ is provided as (SEQ ID NO: 11)
GAGGTTCAACTGCAGCAGTCTGGACCTGAGCTGGTGAAGCCTGGGACTTCA

GTGAAGATGTCCTGCAAGGCTTCTGGTTACTCATTTACTGGCTACTTTATG

AACTGGATGATGCAGAACCATGGAAAGAGCCTTGAGTGGATTGGACGTATT

AATCTTTACAATGGTGATACTTCTACAACCAGAAGTTCAAGGACAAGGCC

ACATTGACTGTGGACAAATCCTCTAACACAGTCCACATGGAGTTCCGGAGC

CTGGCATCTGAGGACTCTGCAGTCTATTATTGTGCAAGTAGTCTGTACTAC

TTTGACTACTGGGGCCAAGGCACCACTTTCACAGTCTCCTCA, an exemplary nucleic acid sequence encoding F25 $V_L$ is provided as (SEQ ID NO: 12)
GACATTGTGATGACCCAGTCTCACAAATTCATGTCCACATCAGTAGGAGAC

AGGGTCAATATTACCTGTAAGGCCAGTCAGGATGTGGGTACTAATGTAGCC

TGGTATCAACAGAAACCAGGGCAATCTCCTAAACTACTGATTTACTGGGCA

TCCACCCGGCAGACTGGAGTCCCTGATCGCTTCACAGGCAGTGGATCTGGG

ACAGATTTCACTCTCACCATTAGCAATGTGCAGTCTGAAGACTTGTCAGAT

TATTTCTGTCAGCAATATAGCAGCTATCCTCTCACGTTCGGTGCTGGGACC

AAGCTGGAGCTGAAACGGGCTGATGCTGCA.

Other nucleic acids encoding antibodies including one or more CDRs from F25, F56, and/or F119 can readily be produced by one of skill in the art, using the amino acid sequences provided herein, and the genetic code. Nucleic acids encoding the amino acid sequences of the antibodies produced by F1, F44 and F54 can be readily determined by one of skill in the art. In addition, one of skill can readily construct a variety of clones containing functionally equivalent nucleic acids, such as nucleic acids which differ in sequence but which encode the same effector molecule ("EM") or antibody sequence. Thus, nucleic acids encoding antibodies, conjugates and fusion proteins are provided herein.

Nucleic acid sequences encoding the antibodies and/or immunotoxins can be prepared by any suitable method including, for example, cloning of appropriate sequences or by direct chemical synthesis by methods such as the phosphotriester method of Narang et al., Meth. Enzymol. 68:90-99, 1979; the phosphodiester method of Brown et al., Meth. Enzymol. 68:109-151, 1979; the diethylphosphoramidite method of Beaucage et al., Tetra. Lett. 22:1859-1862, 1981; the solid phase phosphoramidite triester method described by Beaucage & Caruthers, Tetra. Letts. 22(20):1859-1862, 1981, e.g., using an automated synthesizer as described in, for example, Needham-VanDevanter et al., Nucl. Acids Res. 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding sequences encoding an antibody that specifically binds IRTA2, such as an immunotoxin, can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill.

Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one example, an antibody of use is prepared by inserting the cDNA which encodes a variable region from an antibody that specifically binds IRTA2 into a vector which comprises the cDNA encoding an effector molecule (EM). The insertion is made so that the variable region and the EM are read in frame so that one continuous polypeptide is produced. Thus, the encoded polypeptide contains a functional Fv region and a functional EM region. In one embodiment, cDNA encoding a cytotoxin is ligated to a scFv so that the cytotoxin is located at the carboxyl terminus of the scFv. In one example, cDNA encoding a *Pseudomonas* exotoxin ("PE"), mutated to eliminate or to reduce non-specific binding, is ligated to a scFv so that the toxin is located at the amino terminus of the scFv. In another example, PE38 is located at the amino terminus of the scFv. In a further example, cDNA encoding a cytotoxin is ligated to a heavy chain variable region of an antibody that specifically binds IRTA2, so that the cytoxin is located at the carboxyl terminus of the heavy chain variable region. The heavy chain-variable region can subsequently be ligated to a light chain variable region of the antibody that specifically binds IRTA2 using disulfide bonds. In a yet another example, cDNA encoding a cytotoxin is ligated to a light chain variable region of an antibody that binds IRTa2, so that the cytotoxin is located at the carboxyl terminus of the light chain variable region. The light chain-variable region can subsequently be ligated to a heavy chain variable region of the antibody that specifically binds IRTA2 using disulfide bonds.

Once the nucleic acids encoding the immunotoxin, antibody, or fragment thereof are isolated and cloned, the protein can be expressed in a recombinantly engineered cell such as bacteria, plant, yeast, insect and mammalian cells. One or more DNA sequences encoding the immunotoxin, antibody, or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding the immunotoxin, antibody, or fragment thereof, can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding the immunotoxin, antibody, or fragment thereof can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the immunotoxin, antibody, or fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Isolation and purification of recombinantly expressed polypeptide can be carried out by conventional means including preparative chromatography and immunological separations. Once expressed, the recombinant immunotoxins can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989, all incorporated by reference herein.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, incorporated by reference herein, and especially as described by Buchner et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

In addition to recombinant methods, the immunotoxins, EM, and antibodies disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are well known in the art.

Pharmaceutical Compositions and Therapeutic Methods

Compositions are provided that include one or more of the antibodies that specifically bind IRTA2 (for example, an immunotoxin) that are disclosed herein in a carrier. The compositions can be prepared in unit dosage forms for administration to a subject. The amount and timing of administration are at the discretion of the treating physician to achieve the desired purposes. The antibody can be formulated for systemic or local (such as intra-tumor) administration. In one example, the antibody that specifically binds IRTA2 is formulated for parenteral administration, such as intravenous administration. Any of the antibodies disclosed herein, variants thereof and humanized forms thereof can be used in these methods.

The compositions for administration can include a solution of the antibody that specifically binds IRTA2 dissolved in a pharmaceutically acceptable carrier, such as an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% Sodium Chloride, USP, and typically administered at a dosage of from 0.5 to 15 mg/kg of body weight. Considerable experience is available in the art in the administration of antibody drugs, which have been marketed in the U.S. since the approval of Rituxan® in 1997. Antibody drugs can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

The antibody that specifically binds IRTA2 can be administered to slow or inhibit the growth of cells, such as tumor cells. In one embodiment, a method is provided for inhibiting the growth of a B cell of a non-Hodgkin's lymphoma or a hairy cell leukemia. The method includes contacting the cell with an effective amount of at least one antibody disclosed herein conjugated to an effector molecule.
Methods for measuring cell growth are well known in the art (see, for example, Lewis et al. (1996) *Cancer Res.* 56:1457-65; Tian et al. (2001) *Nutrition and Cancer* 40:180-184). The method may be performed in vivo or in vitro.

A method is also provided for treating a hairy cell leukemia or a B cell lymphoma in a subject, including administering to the subject a therapeutically effective amount of at least one antibody disclosed herein conjugated to an effector molecule. In these applications, a therapeutically effective amount of an antibody-effector molecule conjugate, such as an immunotoxin, is administered to a subject in an amount sufficient to inhibit growth of antigen-expressing cells. Suitable subjects include those with a tumor, such as a B cell malignancy (such as a lymphoma or leukemia). These malignancies include B cell lymphoma, multiple myeloma, Burkitt's lymphoma, marginal zone lymphoma, diffuse large cell lymphoma, non-Hodgkin's lymphoma, and hairy cell leukemia and follicular lymphoma. Thus, suitable subjects include subjects that have hairy cell leukemia or non-Hodgkin's lymphoma.

Amounts effective for this use will depend upon the severity of the disease and the general state of the patient's health. A therapeutically effective amount of the antibody is that which provides either subjective relief of a symptom(s) or an objectively identifiable improvement as noted by the clinician or other qualified observer. These compositions can be administered in conjunction with another chemotherapeutic agent, either simultaneously or sequentially.

Single or multiple administrations of the compositions are administered depending on the dosage and frequency as required and tolerated by the patient. In any event, the composition should provide a sufficient quantity of at least one of the antibodies disclosed herein, such as an immunotoxin, to effectively treat the patient. The dosage can be administered once but may be applied periodically until either a therapeutic result is achieved or until side effects warrant discontinuation of therapy. In one example, a dose of the antibody, such as an immunotoxin, is infused for thirty minutes every other day. In this example, about one to about ten doses can be administered, such as three or six doses can be administered every other day. In a further example, a continuous infusion is administered for about five to about ten days. The subject can be treated with the immunotoxin at regular intervals, such as monthly, until a desired therapeutic result is achieved. Generally, the dose is sufficient to treat or ameliorate symptoms or signs of disease without producing unacceptable toxicity to the patient.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, e.g., Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992) both of which are incorporated herein by reference.

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., J. Parent. Sci. Tech. 44(2):58-65, 1990). Alternatively, hydroxyapatite has been used as a microcarrier for controlled release of proteins (Ijntema et al., Int. J. Pharm. 112:215-224, 1994). In yet another aspect, liposomes are used for controlled release as well as drug targeting of the lipid-capsulated drug (Betageri et al., Liposome Drug Delivery Systems, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342 and U.S. Pat. No. 5,534,496).

Among various uses of the antibodies disclosed herein are disease conditions caused by specific human cells that may be eliminated by the toxic action of an immunotoxin, such as the treatment of malignant cells, including hairy cell leukemia and non-Hodgkin's lymphoma, expressing IRTA2.

Diagnostic Methods and Kits

It is disclosed herein that IRTA2 is expressed in hairy leukemia cells and by non-Hodgkin's lymphoma cells. Thus, expression of IRTA2 can be used to diagnose hairy cell leukemia or non-Hodgkin's lymphoma, or can be used to stage these cancers. Thus, methods are provided for detecting B cell non-Hodgkin's lymphoma or hairy cell leukemia in a subject. The method includes contacting a biological sample from the subject with at least one antibody that specifically binds IRTA2, and detecting the presence of bound antibody. In one example, soluble IRTA2 is detected.

A method is also provided herein for detecting IRTA2 in a biological sample. The method includes contacting the sample with one or more of an antibody that specifically binds IRTA2, such as F1, F25, F44, F54 or F119 (or a variant thereof) to form an antibody-IRTA2 complex. The presence or absence of the complex is detected. In one example, the method detects the presence of soluble IRTA2. It should be noted that the method can also include the use of any antibody disclosed in Table 4 or listed in FIG. 8, or a humanized form thereof, or a variant thereof, wherein the antibody binds an epitope of IRTA2.

The sample can be any sample, including, but not limited to, tissue from biopsies, autopsies and pathology specimens. Biological samples also include sections of tissues, such as frozen sections taken for histological purposes. Biological samples further include body fluids, such as blood, serum, spinal fluid or urine. A biological sample is typically obtained from a mammal, such as a rat, mouse, cow, dog, guinea pig, rabbit, or primate. In one embodiment, the primate is macaque, chimpanzee, or a human. In a further embodiment, the subject has a B cell malignancy, such as hairy cell leukemia or non-Hodgkin's lymphoma or is suspected of having such a B cell malignancy.

In one embodiment, a method is provided for detecting IRTA2 in a biological sample, such as a blood, serum, or plasma sample. Kits for detecting a polypeptide will typically comprise an antibody that specifically binds IRTA2, as disclosed herein.

In some embodiments, an antibody fragment, such as an Fv fragment is included in the kit. For in vivo uses, the antibody can be a scFv fragment. In a further embodiment, the antibody is labeled (such as with a fluorescent, radioactive, or an enzymatic label).

In one embodiment, a kit includes instructional materials disclosing means of use of an antibody that specifically binds IRTA2. The instructional materials may be written, in an electronic form (e.g. computer diskette or compact disk) or may be visual (e.g. video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting a IRTA2 in a biological sample generally includes the steps of contacting the biological sample with an antibody which specifically reacts, under immunologically reactive conditions, to an IRTA2 polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), enzyme linked immunosorbant assays (ELISA), or immunohistochemical assays. The antibodies can also be used for fluorescence activated cell sorting (FACS). A FACS employs a plurality of color channels, low angle and obtuse light-scattering detection channels, and impedance channels, among other more sophisticated levels of detection, to separate or sort cells (see U.S. Pat. No. 5,061,620).

The antibodies of use in the methods provided include any of the antibodies described above. These antibodies include, but are not limited to, an F1, F44, or F54 antibody (produced by a hybridoma or progeny thereof deposited as ATCC Deposit No. PTA-7047; ATCC Deposit No. PTA-7046, or ATCC Deposit No. PTA-7048) or a humanized form thereof. The antibodies of use in the methods disclosed herein also include an antibody that includes both a light and heavy chain with CDR1, CDR2 and CDR3, wherein L-CDR1 comprises the amino acid sequence set forth as amino acids 31 to 35 of SEQ ID NO:5, L-CDR2 comprises the amino acid sequence set forth as amino acids 50 to 66 of SEQ ID NO:5, and L-CDR3 comprises the amino acid sequence set forth as amino acids NO:5, and L-CDR3 comprises the amino acid sequence set forth as amino acids 96 to 101 SEQ ID NO:5, and wherein H-CDR1 comprises the amino acid sequence set forth as amino acids 24 to 34 of SEQ ID NO:6, H-CDR2 comprises the amino acid sequence set forth as amino acids 50 to 56 of SEQ ID NO:6, and H-CDR3 comprises the amino acid sequence set forth as amino acids 89-97 of SEQ ID NO:6. The antibodies of use in the methods disclosed herein also include an antibody that includes both a light and heavy chain with CDR1, CDR2 and CDR3, wherein L-CDR1 comprises the amino acid sequence set forth as amino acids 31 to 35 of SEQ ID NO:1, L-CDR2 comprises the amino acid sequence set forth as amino acids 50 to 65 of SEQ ID NO:1, and L-CDR3 comprises the amino acid sequence set forth as amino acids 95 to 105 of SEQ ID NO:1, and wherein H-CDR1 comprises the amino acid sequence set forth as amino acids 24 to 35 of SEQ ID NO:2, H-CDR2 comprises the amino acid sequence set forth as amino acids 51 to 57 of SEQ ID NO:2, and H-CDR3 comprises the amino acid sequence set forth as amino acids 90 to 98 of SEQ ID NO:2. The antibodies of use in the methods disclosed herein also include an antibody that includes antibody comprises both a light and heavy chain with CDR1, CDR2 and CDR3, wherein H-CDR1 comprises the amino acid sequence set forth as amino acids 31 to 35 of SEQ ID NO:3, H CDR2 comprises the amino acid sequence set forth as amino acids 50 to 65 of SEQ ID NO:3, and H-CDR3 comprises the amino acid sequence set forth as amino acids 100-107 of SEQ ID NO:3, and wherein L-CDR1 comprises the amino acid sequence set forth as amino acids 24 to 34 of SEQ ID NO:4, L-CDR2 comprises the amino acid sequence set forth as amino acids 50 to 56 of SEQ ID NO:4 and L-CDR3 comprises the amino acid sequence set forth as amino acids 89 to 97 of SEQ ID NO:4. One or more of these antibodies may be used in the methods provided herein.

In one embodiment, the method is a sandwich ELISA. A sandwich ELISA requires two antibodies that bind to epitopes that do not overlap on the antigen. This can be accomplished with either two monoclonal antibodies that recognize discrete sites on the antigen of interest, such as IRTA2. To utilize this assay, one antibody (the "capture" antibody) is bound to a solid phase, such as but not limited to the bottom of a well on a microtiter plate, such as a 24, 48 or 96 well plate of polyvinylchloride (PVC). A sample, possibly including the antigen of interest (IRTA2 or a soluble form thereof) is then added and allowed to complex with the bound antibody. Unbound material is then removed with a wash, and a labeled second antibody (the "detection" antibody) is allowed to bind to the antigen, thus completing the "sandwich." The assay can be quantitated by measuring the amount of labeled second antibody bound to the matrix, through the use of a substrate, such as a colorimetric substrate. Exemplary non-limiting enzymes are those that convert a colorless substrate to a colored product, such as p-nitrophenylphosphate (pNPP), which is converted to the yellow p-nitrophenol by alkaline phosphatase. Substrates used with peroxidase include 2,2'-azo-bis(3-ethylbenzthiazoline-6-sulfonic acid) (ABTS), o-phenylenediamine (OPD) and 3,3'5,5'-tetramethylbenzidine base (TMB), which yield green, orange and blue colors, respectively.

Without being bound by theory, it is believed that an advantage of this method is that the antigen does not need to be purified prior to use, and that these assays are very specific. It should be noted that monoclonal antibody combinations must be paired, indicating that each monoclonal antibody that binds the antigen of interest (IRTA2) specifically binds a distinct epitopes on the antigen (IRTA2) in order to maximize sensitivity.

Protocols for sandwich ELISAs are well known in the art. One exemplary non-limiting protocol includes binding a purified unlabeled antibody to the bottom of each well on a plate by adding approximately 50 µL of antibody solution to each well (20 µg/mL in PBS). Generally, PVC will bind approximately 100 ng/well (300 ng/cm$^2$); at least 1 µg/well can be utilized. The plates are incubated for a sufficient time to allow the antibody to bind, such as overnight at 4° C. The wells are then washed with a buffer, such as phosphate buffered saline (PBS) to remove unbound antibody. Any remaining sites for protein binding on the microtiter plate are saturated by incubating with blocking buffer. For example, for assays that do not utilize horseradish peroxidase, the wells are 3% bovine serum albumin (BSA)/PBS with 0.02% sodium azide, and incubated for 2 hours to overnight in a humid atmosphere at room temperature. The sample of interest is then added, such as in a volume of about 50 µL. If dilution is required, dilutions can be made in the blocking buffer (3% BSA/PBS). Incubate for at least 2 hours at room temperature in a humid atmosphere. The wells are then washed, and the labeled second antibody is added. Generally, for accurate quantitation, the second antibody diluted in blocking buffer and is used in excess. The wells are incubated for about 2 hours (or more) and the unbound labeled second antibody is removed by washing with buffer, such as PBS. A commercially available substrate, such as those listed above is then added to the wells and incubated according the manufacturer's instructions. Optical densities at target wavelengths can be measured on a commercially available ELISA plate reader.

In one embodiment, the method includes contacting a first antibody adhered to a solid support with a sample to form an antibody-IRTA2 complex; washing the solid surface to remove any unbound material and contacting the complex with a second antibody. The method includes contacting a second antibody that binds a different epitope of IRTA2 to the sample, washing to remove any unbound second antibody, and detecting the presence of bound second antibody. In one specific, non-limiting example, the antibody is labeled with an enzyme. In another specific non-limiting example, the second antibody is labeled with avidin or biotin. The binding of the second antibody is then detected using biotinylated or avidinated enzyme, respectively. In one example, the enzyme is horseradish perioxidase. In one embodiment, F1 and F25 are utilized in the assay. For example, F1 can be attached to a solid substrate. In another embodiment, F44 and F54 are utilized in the assay. For example, F44 can be attached to a solid substrate.

In one embodiment, the method includes using a solid surface comprising a first antibody produced by a hybridoma or a progeny thereof deposited as ATCC Deposit No. XXX, or a humanized form of this antibody. The sample is incubated with the solid surface, and after washing, the solid surface is incubated with a second antibody including both a light and heavy chain with CDR1, CDR2 and CDR3, wherein L-CDR1 comprises the amino acid sequence set forth as amino acids 31 to 35 of SEQ ID NO:5, L-CDR2 comprises the amino acid sequence set forth as amino acids 50 to 66 of SEQ ID NO:5, and L-CDR3 comprises the amino acid sequence set forth as amino acids 96 to 101 SEQ ID NO:5, and wherein H-CDR1 comprises the amino acid sequence set forth as amino acids 24 to 34 of SEQ ID NO:6, H-CDR2 comprises the amino acid sequence set forth as amino acids 50 to 56 of SEQ ID NO:6, and H-CDR3 comprises the amino acid sequence set forth as amino acids 89-97 of SEQ ID NO:6. In one example, the second antibody is labeled with biotin. Detection of bound IRTA2 is performed by incubating enzyme bound streptavidin such as horseradish peroxidase (HRP) strepavidin, with the solid surface. After washing, a substrate is incubated with the solid surface to detect the presence of bound second antibody, thereby detecting soluble IRTA2.

In another embodiment, the method includes using a solid surface comprising an antibody produced by a hybridoma or a progeny thereof deposited as ATCC Deposit No. PTA-7046 or a humanized form thereof. The sample is incubated with the solid surface, and after washing, the solid surface is incubated with a second antibody. The second antibody is produced by a hybridoma or a progeny thereof deposited as ATCC Deposit No. PTA-7048, or is a humanized form of this antibody. In one example, the second antibody is labeled with biotin. Detection of bound IRTA2 is performed by incubating enzyme bound strepavidin with the solid surface. Detection of bound IRTA2 is performed by incubating enzyme bound streptavidin such as horseradish peroxidase (HRP) strepavidin, with the solid surface. After washing a substrate is incubated with the solid surface to detect the presence of bound second antibody, thereby detecting soluble IRTA2.

The disclosure is illustrated by the following non-limiting Examples.

EXAMPLES

Example 1

Materials and Methods

Cells: Nineteen human hematologic cell lines were used in this study (Table 1).

TABLE I

Human Hematological Cell Lines Used in This Study

| Name | Origin | EBV status[a] | Reference or ATCC number[b] |
|---|---|---|---|
| JD38 | B-NHL[c](undifferentiated) | − | 24 |
| Karpas 1106 | B-NHL (mediastinal lymphoblastic) | − | 25 |
| OCI-Ly2 | B-NHL (diffuse large cell type) | − | 26 |
| OCI-Ly7 | B-NHL (diffuse large cell type) | − | 26 |
| OCI-Ly10 | B-NHL (immunoblastic) | − | 26 |
| SU-DHL-5 | B-NHL (diffuse large cell, noncleaved cell type) | − | 27 |
| SU-DHL-6 | B-NHL (diffuse, mixed small and large cell type) | − | 27 |
| CA46 | Burkitt's lymphoma | − | 28 |
| Daudi | Burkitt's lymphoma | + | CCL-213 |
| AMALWA | Burkitt's lymphoma | + | CRL-1432 |
| NC-37 | Burkitt's lymphoma | + | CCL-214 |
| Raji | Burkitt's lymphoma | + | CCL-86 |
| Ramos | Burkitt's lymphoma | − | CRL-1596 |
| CCRF-SB | Lymphoblastic leakemia | + | CCL-120 |
| arpas 299 | Anaplastic large cell lymphoma | − | 29 |
| L540 | Hodgkin's disease | − | 30 |
| MOLT-4 | T-cell lymphoma | − | CRL-1582 |
| RPMI 6666 | Hodgkin's disease | + | CCL-113 |
| U-937 | Histiocytic lymphoma | − | CRL-1593.2 |

[a]EBV, Epstein-Barr virus
[b]ATCC, American Type Culture Collection, Manassas, VA 20208, http://www.atcc.org
[c]B-NHL, B-cell non-Hodgkin's lymphoma CA46, CCRF-SB, JD38, MOLT-4, NAMALWA, NC-37, Raji, Ramos, RPMI 6666, SU-DHL-5, SU-DHL-6 and U-937 cells were grown in RPMI 1640 medium supplemented with 10% fetal bovine serum (FBS; HyClone, Logan, Utah). Daudi cells were grown in RPMI 1640 medium supplemented with 20% FBS. Karpas 299 and L540 cells were grown in Iscove's modified Dulbecco's medium (IMDM) supplemented with 10% FBS. OCI-Ly2, OCI-Ly7, OCI-Ly10 and Karpas 1106 cells were maintained in IMDM supplemented with 15% normal human serum. 293T cells were grown in Dulbecco's modified Eagle's medium supplemented with 10% FBS. Sp2/0-neo myeloma cells (Nagata et al., *J. Immunol Methods* 280:59-72, 2003) were used for the fusion partner for the hybridoma formation and maintained in IMDM with 15% FBS. Blood cells were obtained from patients with HCL via an approved protocol.

Primers. The DNA oligo primers are listed in Table 2. The primers were synthesized by Lofstrand Laboratories (Gaithersburg, Md.).

TABLE 2

Oligonucleotide primers used in this study

| No. | Name | Sequence[a] |
|---|---|---|
| 1 | IR2/-fr1F | 5'-CGC GGATCC AAAGCCACC ATG CTGCTGTGGGTGATATTACTGG-3' SEQ ID NO: 29 |
| 2 | IR2-fr1R | 5'-CCCT GAATTC TCTGTAGTCAGTGAGAAGCTGATGG-3' SEQ ID NO: 30 |
| 3 | IR2-fr2F | 5'-GAAACCCAGGAAGATTCTCTGCGCACT-3' SEQ ID NO: 31 |
| 4 | IR2-fr2R | 5'-ATAGTTTA GCGGCC GCCTGTGGCAAAAGGGCCACTTC-3' SEQ ID NO: 32 |
| 5 | IR2-fr3F | 5'-GACACAATATCACTCAGTGTTATAGTTCC-3' SEQ ID NO: 33 |
| 6 | IR2-fr3R | 5'-ATAGTTTA GCGGCCGC TCATCTGTGAGGAGCTGAGGAAGCC-3' SEQ ID NO: 34 |
| 7 | IR1-F | 5'-CGG GATATC AAAGCCACC ATG CTGCTGTGGGCGTCCTTG-3' SEQ ID NO: 35 |
| 8 | IR1-R | 5'-ATAGTTTA GCGGCCGC TTAACTTTCTTCATCCTTAGAGCTGATC-3' SEQ ID NO: 36 |

TABLE 2-continued

Oligonucleotide primers used in this study

| No. | Name | Sequence[a] |
|---|---|---|
| 9 | IR1-FcR | 5'-ATAGTTTA GCGGCCGC CATCTCTGTTGCCTGGGGTCTC-3'<br>SEQ ID NO: 37 |
| 10 | IR3-fr1F | 5'-CGG GATATC AAAGCCACC ATG CTTCTGTGGCTGCTGCTGC-3'<br>SEQ ID NO: 38 |
| 11 | IR3-fr1R | 5'-ATAGTTTA GCGGCCGC CGCCTGTTCTGTTCCTGGAAGTTCC-3'<br>SEQ ID NO: 39 |
| 12 | IR3-fr2F | 5'-GTCTCGCCCCGTCCTCACCCTCAGG-3'<br>SEQ ID NO: 40 |
| 13 | IR3-fr2R | 5'-ATAGTTTA GCGGCCGC CTAGTGGTCTGAGGCCAGTAATACACG-3'<br>SEQ ID NO: 41 |
| 14 | IR4-fr1F | 5'-CGC GGATCC AAAGCCACC ATG CTGCTGTGGTCATTGCTGG-3'<br>SEQ ID NO: 42 |
| 15 | IR4-fr1F | 5'-ATAGTTTA GCGGCCGC CAGCTGTCATGAGGTCTCTTCTATAGC-3'<br>SEQ ID NO: 43 |
| 16 | IR4-fr2F | 5'-GACTCACAGGATCAGAAAACAGAGCCTCC-3'<br>SEQ ID NO: 44 |
| 17 | IR4-fr2R | 5'-ATAGTTTAGCGGCCGCTTATGATTTCTTCACAGAAGAGTAG-3'<br>SEQ ID NO: 45 |
| 18 | IR5-F | 5'-CGGAATTCAAAGCCACCATGCTGCCGAGGCTGTTGCTGT-3'<br>SEQ ID NO: 46 |
| 19 | IR5-R | 5'-ATAGTTTAGCGGCCGCTTACATAGCATCTTCATAGTCCACATCTG-3'<br>SEQ ID NO: 47 |
| 20 | IR5-FcR | 5'-ATAGTTTAGCGGCCGCCTGAGGTAAGATGATTGCTTCTGGC-3'<br>SEQ ID NO: 48 |
| 21 | Actin-F | 5'-GCATGGGTCAGAAGGAT-3'<br>SEQ ID NO: 49 |
| 22 | Actin-R | 5'-CCAATGGTGATGACCTG-3'<br>SEQ ID NO: 50 |
| 23 | 2c-F | 5'-AGCCCTTCAGACTCGGACTC-3'<br>SEQ ID NO: 51 |
| 24 | 2c-R | 5'-TGGGGCAGCCTAAATCTT-3'<br>SEQ ID NO: 52 |

[a] Recognition sites of restriction enzymes are squared. They are GGATCC (BamHI), GAATTC (EcoRI), GCGGCCGC (NotI), and GATATC (EcoRV). Initiation codons (ATG) are underlined.

Plasmids. Five different IRTA cDNAs (IRTA1, IRTA2, IRTA3, IRTA4 and IRTA5) were cloned and a pair of expression vectors was constructed for each cDNA. One encodes the full-length protein under cytomegalovirus (CMV) promoter and the other encodes the extracellular domain genetically fused with human IgG1 Fc portion. The GenBank accession numbers of reference sequences of IRTA1 to 5 are AF343659, AF343662, AF459027, AF459633 and AF459634, respectively.

The IRTA DNAs were amplified by PCR from cDNA of human spleen (Clontech, Palo Alto, Calif.) or from Daudi cells (prepared from total RNA using random hexamer and Superscript III Reverse Transcriptase; Invitrogen, Carlsbad, Calif.). The primers used for PCR are listed in Table 2. The cDNA fragments were digested with the restriction enzymes listed in the table and ligated into the multicloning site of the pcDNA3 plasmid (Invitrogen). For IRTA2, IRTA3, and IRTA4, two or three DNA fragments were cloned into the vector and connected in tandem in the same vector. Finally, full-length cDNAs of 5 different IRTAs were cloned under a CMV-promoter in pcDNA3.

For Fc-fusion proteins, a Not I-Xba I fragment of pRB-2k1-CD30 (Nagata et al., *J. Immunol. Methods* 280:59-72, 2003), which contains the hinge and Fc portion of IgG1 with three introns, was subcloned into pcDNA3. To prevent its possible interaction with IRTAs, the first 8 amino acids of the constant region 2 of the Fc (amino acids 231-238) were changed from APELLGGP (SEQ ID NO: X) to APPVAGP (SEQ ID NO: X) by a PCR-based method. These mutations (E233P, L234V, L235V and deletion of G237) reduce the affinity of IgG1 for FcγRI to a non-detectable level (Chappel et al., *Proc Natl Acad Sci USA* 88:9036-40, 1991). DNA fragments that encode the extracellular domains of the IRTAs, including the signal peptides, were amplified by PCR, and then inserted upstream of the human Fc in pcDNA3. The plasmids for the expression of human CD30 (pHRm30c)

(Diehl et al., *J Cancer Res Clin Oncol* 101:11-124, 1981) or the extracellular domain of the CD30-Fc fusion protein (pRB-2k1-CD30) (Nagata et al., *Clin Cancer Res* 8:2345-55, 2002) were used as controls in some experiments.

Transfection of 293T Cells with the Plasmids. In a typical experiment, $5 \times 10^5$ of 293T cells were seeded in a 10-cm dish (BD Biosciences, Bedford, Mass.) 24 hours prior to the transfection. Four µg of plasmid DNA was transfected by Lipofectamine and Plus reagent (Invitrogen) according to the manufacturer's instruction. After 48-72 hour transfection, the cells transfected with the plasmids encoding full-length IRTAs or CD30 were used for fluorescence activated cell sorter (FACS) analysis, cell-enzyme-linked immunosorbent assay (cell-ELISA), Western blot or immunofluorescence.

Preparation of the Fc-fusion Proteins. The 293T cells transfected with plasmids encoding Fc-fusion proteins secreted the Fc-fusion proteins in the supernatants. From day 2 to day 8 after transfection, the Fc-fusion proteins in the media were harvested daily. The concentration of the Fc-fusion proteins was measured by a human IgG-specific sandwich ELISA using purified CD30-Fc as the standard. Several of the Fc-fusion proteins were purified with protein A Sepharose 4 Fast Flow (Amersham Biosciences, Piscataway, N.J.).

Production of MAbs. A 6-week-old female Balb/c mouse was DNA-immunized 5 times with the IRTA2 plasmid as previously described (Nagata et al., *J Immunol Methods* 280: 59-72, 2003). The mouse was boosted with 293T cells transfected with the same plasmid, and 3 days later the spleen cells were fused with SP2/0-neo myeloma cells as described previously (Nagata et al., *J Immunol Methods* 280:59-72, 2003). The hybridomas were screened for secretion of specific MAbs in an ELISA using IRTA2-Fc antigen. After multiple rounds of cell cloning by limiting dilution, the established hybridomas were grown to a high density to harvest the MAbs in the culture supernatants. The isotype of the MAbs was determined by mouse MAb isotyping reagents (ISO2; Sigma-Aldrich, St. Louis, Mo.). Ig concentrations in the culture supernatants were determined by a sandwich ELISA as previously described (Nagata et al., *Hybridoma* 10:369-78, 1991).

ELISA. In a typical indirect ELISA for the screening of hybridomas, microtiter plates (MaxiSorp; Nalge Nunc, Rochester, N.Y.) were coated with 100 ng/50 µl/well of goat anti-human IgG in phosphate buffered saline (PBS) for 2 hours at room temperature. Next, 50 ng/100 µl/well of IRTA2-Fc in blocking buffer (25% DMEM, 5% FBS, 25 mM HEPES, 0.5% bovine serum albumin, 0.1% sodium azide in PBS) was added to each well and incubated for 2 hours at room temperature. After washing with PBS containing 0.05% Tween 20, 50 µl of the hybridoma supernatants were added and incubated for 2 hours at room temperature. After washing, the bound MAbs were detected by a 2-hour incubation with horseradish peroxidase (HRP)-labeled goat anti-mouse IgG (Jackson ImmunoResearch, Grove, Pa.) followed by tetramethylbenzidine (TMB) substrate kit (Pierce, Rockford, Ill.). In some experiments, other IRTA-Fc fusion proteins were used instead of IRTA2-Fc.

Affinity Determination. Affinities (dissociation constant, Kd) of the anti-IRTA2 MAbs to IRTA2-Fc were determined by ELISA as previously described (Friguet et al., *J Immunol Methods* 77:305-19, 1985). Briefly, each MAb was incubated with various concentrations of IRTA2-Fc at room temperature for 20 hours to reach equilibrium; then the amount of MAb that remains unbound at equilibrium was measured by the indirect ELISA as described above.

Cell-ELISA. 293T cells that had been transfected with the IRTA2 expression plasmid or a CD30 expression plasmid 48 hours prior to use were seeded into 96 well plates ($2 \times 10^4$/well). After overnight culture, the cells were fixed with 3.7% formalin in the culture medium at room temperature overnight. Incubation with a dilution of MAbs, secondary antibody and substrate was performed as described in the ELISA protocol except that 1% FBS in PBS was used for washing.

FACS Analysis. Various lymphoma cell lines and transfected 293T cells were used in the FACS analysis. Typically, $4 \times 10^5$ cells were incubated with 250 ng of MAb in 100 µl of PBS containing 5% FBS and 0.1% sodium azide. After incubation for 1 hour at 4° C., the cells were washed twice with the same buffer and incubated with 1:100 dilution of R-phycoerythrin (R-PE)-labeled goat anti-mouse IgG F(ab')$_2$ (BioSource, Camarillo, Calif.) for 1 hour. After washing twice, the cells were suspended in 1 ml buffer, and the fluorescence associated with the live cells was measured using a FACS Caliber Flow Cytometer (Becton Dickinson, Franklin Lakes, N.J.).

For blood samples of patients with HCL or normal donors, whole peripheral blood mononuclear cells (PBMCs) were isolated using Ficoll-Paque (Amersham Biosciences) and stained with mixtures of F56-R-PE (200 ng/ml, specially made by Molecular Probes, Eugene, Oreg., CD20 PerCP-Cy5.5, and CD22-FITC or CD103-FITC (Becton Dickinson). In some experiments, IRTA2-Fc or CD30-Fc was added at 20 µg/ml with the antibodies as the competitors. Compensations of fluorescence were set prior to each analysis using calibrated beads (CaliBRITE beads, Becton Dickinson).

Immunofluorescence Antibody. 293T cells were transfected with an IRTA2 or a CD30 plasmid; 48 hours after transfection, the cells were detached, counted, and combined in a 1:1 ratio. A total $5 \times 10^4$ cells were seeded in each well of a 4-well chamber slide (Nalge Nunc). After 24 hours, the cells were washed with PBS and fixed in 3.7% formaldehyde for 5 minutes. After washing with PBS twice and blocking with 5% normal goat serum, the cells were incubated with a mixture of anti-IRTA2 MAb F56 (IgG1) and anti-CD30 MAb Ki-1 (IgG3) at 10 µg/ml each. After washing, a mixture of Alexa 488-conjugated goat-anti-mouse IgG1 (1:1000 dilution; Molecular Probes) and Alexa 555-conjugated goat-anti-mouse IgG3 (1:1000 dilution; Molecular Probes) was added to the cells. The primary antibodies, F56 and Ki-1, on the slides were probed by the different secondary reagents with different wave lengths of the emission based on the different subclass. Nuclei were stained with 4',6-Diamidino-2-phenylindole (DAPI) (1 µg/ml; Roche Applied Science, Indianapolis, Ind.). Negative controls were performed without antibodies.

Western Blotting. Typically, 40 µg of cell lysates or 20 ng of Fc-fusion proteins for each well or strip were separated onto 4-20% sodium dodecyl sulfate (SDS) polyacrylamide gels (Bio-Rad, Hercules, Calif.) under reducing condition. Proteins were transferred to a polyvinylidene difluoride membrane (0.2 µm; Immuno-Blot; Bio-Rad) in transfer buffer (25 mM Tris-HCl, 192 mM glycine, 30% (v/v) methanol, pH 8.3) at 4° C. for 1 hour at 250 mA. After blocking with 5% skim milk in PBS, the membrane was incubated with 2.5-10 µg/ml of MAbs. The bound MAbs were detected with alkaline phosphatase-labeled goat anti-mouse IgG (Bio-Source) and 5-bromo-4-chloro-3-indolyl phosphate/p-nitroblue tetrazolium chloride substrate (BCIP/NBT; Pierce).

RT-PCR. The RNA expression of IRTA2 in the cell lines was examined by a RT-PCR method. Total RNA was prepared from each cell line using Trizol LS reagent (Invitrogen). cDNA was made from 4 µg of the total RNA by Superscript III Reverse Transcriptase (Invitrogen) with random hexamer priming according to the manufacture's instructions. PCRs were performed using cDNA from 100 ng RNA and 2 sets of primers for β-actin and IRTA2 (c isoform specific) listed in Table 1 with 26 cycles of amplification (95° C., 15 seconds; 55° C., 30 seconds; 72° C., 1 minute).

Example 2

Cloning of IRTA cDNAs and Preparation of Fc-Fusion Proteins

Because of the high homology of IRTA2 to other family members, it was important to prepare all possible IRTA proteins to evaluate cross-reactivity of the anti-IRTA2 antibodies. All cDNAs of these IRTAs whose mRNA expression had been reported were amplified by RT-PCR and cloned into a pair of vectors: one for the expression of the full-length of the genes under a CMV-promoter and the other for the expression of the extracellular domains as fusion proteins using the Fc portion of human IgG1. FIG. 1A summarizes the structure of each IRTA and the plasmid construction. All full-length proteins were expressed on 293T cells transiently transfected with each plasmid as shown by cross-reactive MAbs (see below). All the Fc-fusion proteins were secreted into the culture supernatants of 293T cells transiently transfected with each plasmid although the production level varied (0.4-10 µg/ml). The purified Fc-fusion proteins migrated in SDS-PAGE with the expected sizes (FIG. 1B).

Example 3

Production of MAbs

A Balb/c mouse was DNA-immunized with the full-length IRTA2 expression plasmid and boosted with 293T cells transfected with the same plasmid (Nagata et al., *J Immunol Methods* 280:59-72, 2003). The fusion experiment resulted in 36 stable hybridomas secreting MAbs that reacted to the IRTA2 extracellular domain-Fc but not to CD30-Fc (Table 4). Four (11%) IgG1s, 24 (67%) IgG2 as, and 8 (22%) IgG2bs were obtained. All the MAbs reacted to IRTA2-Fc with high affinities (1.1-18.7 nM of Kds, 5.4 nM in average). In addition, all the MAbs reacted to IRTA2 expressed on 293T cells transfected with IRTA2 expression plasmid without background reactivity to 293T cells transfected with a CD30 plasmid. It was concluded that all the MAbs recognize the native conformation of IRTA2 on the plasma membrane with high affinity. Three MAbs (F25, F56 and F119) were initially chosen for further study based on their high affinities, different subclass, no cross-reactivity to other IRTA family members, and reactivity in immunocytochemistry and Western blotting (see below). The characteristics of the three MAbs are summarized in Table 3.

TABLE 3

Characteristics of anti-IRTA2 monoclonal antibodies used in this study[a]

| Name | IgG Subclass[b] | Reactiviy to FACS (log MFI)[c] | | Reactivity to IRTA2-Fc | | Cross reactivity | Reactivity to denatured antigen | |
|---|---|---|---|---|---|---|---|---|
| | | to IRTA2/ 293T | to CD30/ 293T | ELISA titer[e] (ml/µg) | Affinity[f] (Kd, nM) | to other IRTAs[d] | Cell-ELISA titers (ml/µg) | Western blotting[h] |
| F25 | 2a | 2.59 | 0.74 | 320 | 1.2 | — | 0.6 | + |
| F56 | 1 | 2.56 | 0.66 | 880 | 4.4 | — | 250 | − |
| F119 | 2b | 2.54 | 0.85 | 850 | 5.4 | — | 0.3 | − |

[a]MAbs were screened based on the reactivity to IRTA2 in an ELISA. Thirty-six MAbs were sealected and all of them specifically reacted to 293T cells transfected with IRTA2. The three MAbs shown were used for the analysis of cell lines and HCL cells.

[b]All MAbs possess κ light chain.

[c]Geometric mean fluorescence intensity in a FACS analysis using 293T cells transfected with IRTA2 or CD30 expression plasmids. Transfection efficiencies were almost 100%. Some histograms of similar experiments are shown in FIG. 2B.

[d]Summary of reactivity to IRTAs-Fc and 293T cells with IRTAs shown in FIG. 2A and B.

[e]The reciprocal of the MAb concentration needed to attain an absorbance of 0.2 in ELISA when a positive control (F56, 20 ng/ml) had an absorbance value of 1.0 in the same plate. These values are equal to the titers of 1 µg/ml of MAb solution. All MAbs did not react to a negative control (CD30-Fc).

[f]Defined by an ELISA measurement of free MAb concentration in the MAb-IRTA2-Fc mixtures after making equilibrium (20 hr, 25° C.).

[g]293T cels transfected with the IRTA2 plasmid were used as the cell ELISA antigen after fixation of 3.7% formation overnight. The values are the reciprocal of the MAb concentration needed to attain an absorbance of 0.2 in ELISA when a positive control (an antiserum, 1/4000) had an absorbance value of 0.5 in the same plate. These are equal to the titers of 1 µg/ml of MAb solution. All the MAbs did not react to a negative control ('0.2, CD30-transfected 293T).

Figure 3:
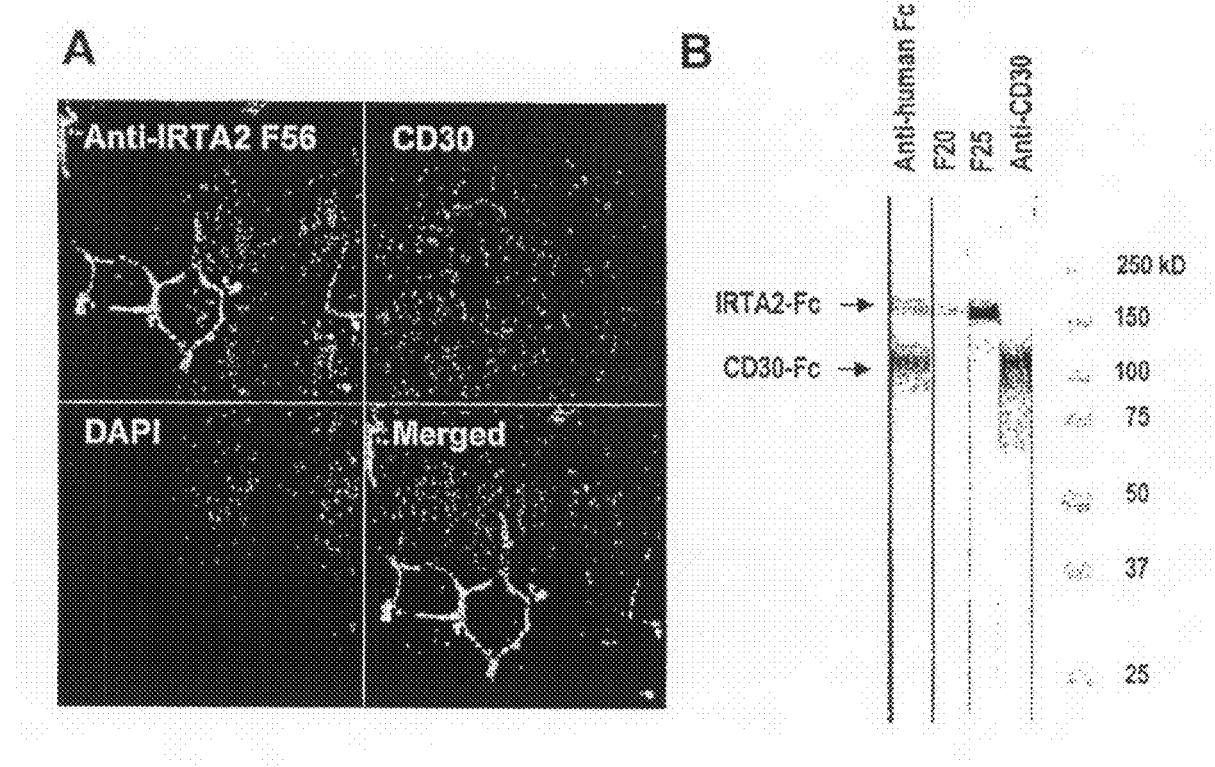
FIGS. 3A-B are digital images illustrating the use of the anti-IRTA2 MAbs for immunofluorescence and Western blotting.

[h]Reactivity to IRTA-Fc and IRTA2-transfected cells in Western blotting. Parts of the results are shown in FIG. 3. +, positive; −, negative.

TABLE 4

Anti-IRTA2 Monoclonal Antibodies

| Mab (use) | Kd(nM) | epilope lopo | IgG class | Reactivity to IRTA2 domains (Fc-fusions) | | | | | | | | | | | Reactivity to other IRTAs (Fc-fusion) | | | | | Reactivity to cells (FACS) | | | |
|---|---|---|---|---|---|---|---|---|---|---|---|---|---|---|---|---|---|---|---|---|---|---|---|
| | | | | ED1-3 | ED1-2 | ED1 | ED2 | ED3 | ED4-6 | ED4-9 | RFc-2a | ED1-8 | 1-8-RFc | fuD-RFc | ED9 | IRTA1 | IRTA2 | IRTA3 | IRTA4 | IRTA5 | IRTA2/ 293T | XG2 | SUDHL-E | OCI-Ly7 |
| F25 | 1.2 | 2 | G2a | + | + | + | − | − | − | − | + | + | + | + | − | − | + | − | − | − | + | − | + | + |
| F20 | 1.5 | 2 | G2b | + | + | + | − | − | − | − | + | + | + | + | − | − | + | − | − | − | + | − | + | + |
| F91 | 1.9 | 2 | G2b | + | + | + | − | − | − | − | + | + | + | + | − | − | + | − | − | − | + | − | + | + |
| F99 | 1.6 | 2 | G2b | + | + | + | − | − | − | − | + | + | + | + | − | − | + | − | − | − | + | − | + | + |
| F28 | 2.2 | 2 | G2a | + | + | + | − | − | − | − | + | + | + | + | − | − | + | − | − | − | + | − | + | + |
| F23 | 3.6 | 1 | G2a | + | + | − | − | − | − | − | + | + | + | + | − | − | + | − | − | − | + | − | + | + |
| F34 | 3.0 | 1 | G2a | + | + | − | − | − | − | − | + | + | + | + | − | − | + | − | − | − | + | − | + | + |
| F62 | 2.8 | 1 | G2a | + | + | − | − | − | − | − | + | + | + | + | − | − | + | − | − | − | + | − | + | + |
| F54 | 6.1 | 1 | G2a | + | + | − | − | − | − | − | + | + | + | + | − | − | + | − | − | − | + | − | + | + |
| F65 | 4.1 | 1 | G1 | + | + | − | − | − | − | − | + | + | + | + | − | − | + | − | − | − | + | − | + | + |
| F59 | 6.0 | 6 | G1 | + | − | − | − | − | − | − | + | + | + | + | − | − | + | − | − | − | + | − | + | + |
| F15 | 7.6 | 6 | G1 | + | − | − | − | − | − | − | + | + | + | + | − | − | + | − | − | − | + | − | + | + |
| F44 | 4.6 | 3 | G2a | − | − | − | + | + | − | − | + | + | + | + | − | − | + | − | − | − | + | − | + | + |
| F119 | 5.4 | 3 | G2b | − | − | − | + | + | − | − | + | + | + | + | − | − | + | − | − | − | + | − | + | + |
| F5 | 4.8 | 3 | G2a | − | − | − | + | + | − | − | + | + | + | + | − | − | + | − | − | − | + | − | + | + |
| F126 | 8.4 | 8 | G2a | − | − | − | − | − | + | + | + | + | + | + | − | − | + | − | − | − | + | − | + | + |
| F108 | 1.9 | 8 | G2b | − | − | − | − | − | + | + | + | + | + | + | − | − | + | − | − | − | + | − | + | + |
| F56 | 4.4 | 11 | G1 | − | − | − | − | − | − | + | + | + | + | + | − | − | + | − | − | − | + | − | + | + |
| F51 | 3.7 | 11 | G2a | − | − | − | − | − | − | + | + | + | + | + | − | − | + | − | − | − | + | − | + | + |
| F26 | 2.7 | 11 | G2b | − | − | − | − | − | − | + | + | + | + | + | − | − | + | − | − | − | + | − | + | + |
| F69 | 4.1 | 10 | G2a | − | − | − | − | − | − | + | + | + | + | + | − | − | + | + | + | − | + | + | + | + |
| F117 | 3.5 | 10 | G2b | − | − | − | − | − | − | + | + | + | + | + | − | − | + | + | + | − | + | + | + | + |
| F66 | 7.5 | 10 | G2a | − | − | − | − | − | − | + | + | + | + | + | − | − | + | + | + | − | + | + | + | + |
| F100 | 3.6 | 9 | G2b | − | − | − | − | − | − | + | + | + | + | + | − | − | + | − | + | − | + | + | + | + |
| F46 | 6.6 | 9 | G2a | − | − | − | − | − | − | + | + | + | + | + | − | − | + | − | + | − | + | + | + | + |
| F11 | 24.4 | — | G2a | − | − | − | − | − | − | − | − | − | − | − | − | + | − | − | − | − | + | + | + | + |
| F47 | 4.9 | — | G2b | − | − | − | − | − | − | − | − | − | − | − | − | + | − | − | − | − | + | + | + | + |
| F109 | 18.7 | — | G2a | − | − | − | − | − | − | − | − | − | − | − | − | + | − | − | − | − | + | + | + | + |
| F127 | 13.0 | 7 | G2a | − | − | − | − | − | − | − | + | + | + | + | − | − | + | − | − | − | + | + | + | + |
| F124 | 10.6 | 5 | G2b | − | − | − | − | − | − | − | + | + | + | + | − | − | + | − | − | + | + | + | + | + |
| F1 | 5.7 | 5 | G1 | − | − | − | − | − | − | − | + | + | + | + | − | − | + | − | − | + | + | + | + | + |
| F97 | 7.98 | 5 | G2a | − | − | − | − | − | − | − | + | + | + | + | − | − | + | − | − | + | + | + | + | + |
| F103 | 8.2 | 5 | G2a | − | − | − | − | − | − | − | + | + | + | + | − | − | + | − | − | + | + | + | + | − |
| F115 | 7.9 | 4 | G2a | − | − | − | − | − | − | − | + | + | + | + | − | − | + | − | − | − | + | − | − | − |
| F48 | 6.7 | 4 | G2a | − | − | − | − | − | − | − | + | + | + | + | − | − | + | − | − | − | + | − | − | − |
| F74 | 4.4 | 4 | G2a | − | − | − | − | − | − | + | − | + | + | + | − | − | + | − | − | − | + | − | − | − |

Example 4

Cross-Reactivity of the Anti-IRTA2 MAbs

Figure 2:
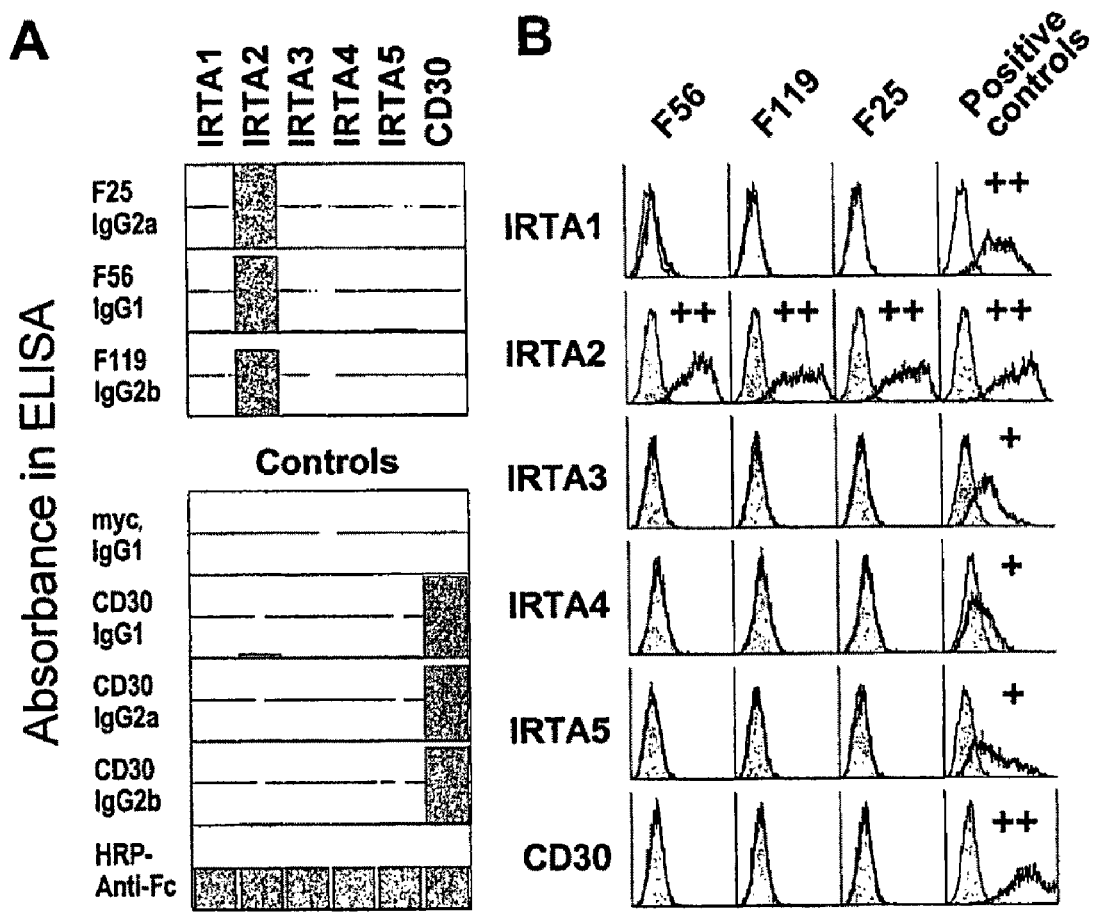
FIGS. 2A-B are a bar graph and a set of plots showing the cross-reactivity of the anti-IRTA2 MAbs to other IRTA family members.

To examine the cross-reactivity of the MAbs to other IRTAs, the reactivity of each MAb to other IRTA-Fc fusion proteins was tested in an ELISA and to native IRTAs expressed on transfected 293T cells. Overall results indicate that 25 out of 36 MAbs specifically reacted with IRTA2 whereas 11 MAbs showed cross-reactivity to other IRTAs to various extents. As shown in FIG. 2, the binding of MAbs, F25, F56, and F119 was specific to IRTA2 in both assays.

Example 5

Reactivity of the MAbs to Denatured IRTA2

The reactivity of the MAbs was examined in a cell-ELISA, by immunocytochemistry and by Western blotting. In these methods, most of the epitopes on IRTA2 protein were probably denatured.

First, the reactivity of the MAbs to formalin-fixed antigen on transfected 293T cells in a cell ELISA was tested. About two-thirds of MAbs (21 out of 36) lost their reactivity to formalin-fixed IRTA2 (titers were less than 1), but 15 MAbs bound to the formalin-fixed antigen to some extent. MAb F56 specifically reacted to IRTA2 with a good titer (Table 3), and was used in further studies.

An immunofluorescence study was performed using MAb F56 for the detection of IRTA2 in the transfected cells (FIG. 3A). Two dishes of 293T cells were separately transfected with IRTA2 or CD30 plasmids and were mixed at a 1:1 ratio and reseeded. The cells were fixed in formaldehyde and double-stained with a mixture of anti-IRTA2 MAb F56 (IgG1) and anti-CD30 MAb Ki-1 (IgG3). Four views with different filters of the same field are shown (FIG. 3A). The cells expressing IRTA2 and stained with F56 showed a green fluorescence signal on the plasma membrane (anti-IRTA2 F56). In contrast, different cells expressing CD30 and stained with anti-CD30 showed a red signal on the plasma membrane (CD30). The nuclei of the cell were visualized with DAPI. The result indicates that MAb F56 can be used in immunofluorescence staining of cells after fixation with formalin to detect recombinant IRTA2 protein expressed on the plasma membrane.

Next, the reactivity of the MAbs to SDS-denatured antigen was examined in Western blotting. A mixture of IRTA2-Fc and CD30-Fc fusion proteins were blotted on the membrane and incubated with each MAb. Only with MAbs F25 and F20 was a 160-kDa band of IRTA2-Fc visualized (FIG. 3B). These MAbs did not react with CD30-Fc on the same blots. The CD30-Fc band around 110-kDa was stained with an anti-human Fc antibody and an anti-CD30 MAb (Ber-H2), but not with F20 or F25. Therefore, the reactivity of F20 and F25 on the Western blot is specific. None of the other 34 MAbs were able to react with IRTA2 in Western blotting, indicating they can detect native but not SDS-denatured IRTA2.

Example 6

Expression of IRTA2 on Human Cell Lines

Figure 4:
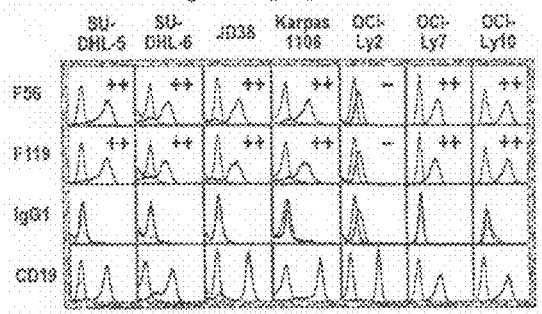
FIGS. 4A-D are graphs, digital images, and a table showing the expression of IRTA2 on cell lines.
Figure 4:
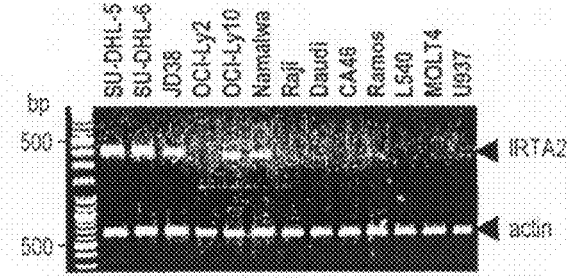
Figure 4:
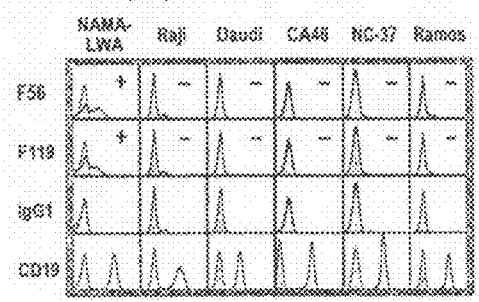
Figure 4:
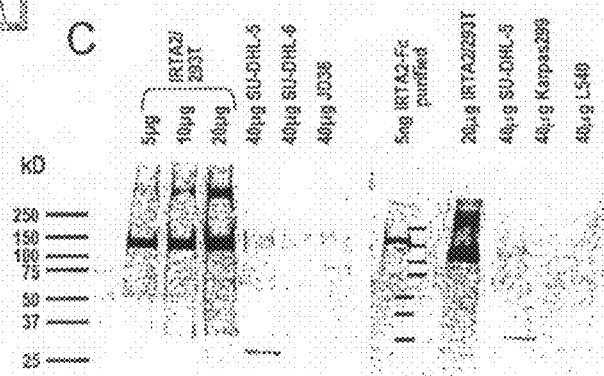
Figure 4:
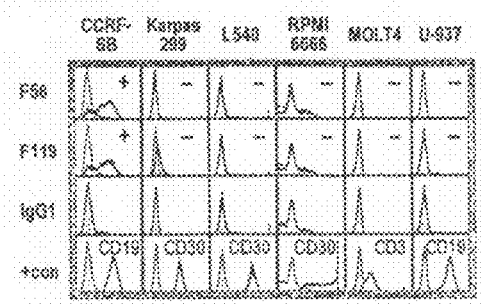
Figure 4:
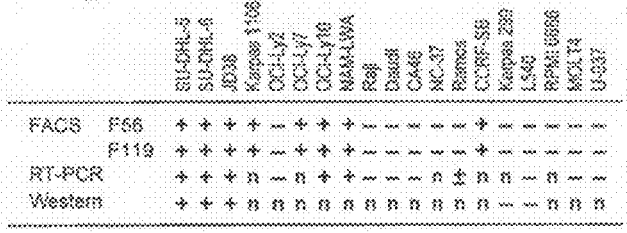

IRTA2 expression was surveyed on a variety of human cancer cell lines by FACS using MAbs F56 and F119 (FIG. 4A). The characteristics of these cell lines are listed in Table 1. IRTA2 was detected on 7 B-cell lymphoma lines; 6 were derived from a different type of non-Hodgkin's lymphoma (NHL). Only 1 of 6 Burkitt's lymphoma cell lines was positive and this weakly expressed IRTA2 (FIG. 4A). All cells were stained with the appropriate CD markers used as the positive controls and were not stained with mouse IgG1 as the negative control. To verify that the staining was specific, a 100-fold excess of IRTA2-Fc or CD30-Fc was used as the competitors of the staining. IRTA2-Fc was able to block staining of SU-DHL-5 and OCI-LY7 cells, whereas CD30-Fc was ineffective.

The expression of IRTA2 mRNA in cells was examined by RT-PCR (FIG. 4B). A set of primers (2cF and 2cR [Table 2]) for IRTA2 located on separate exons was designed to give a 432-bp PCR fragment. This primer set should detect only the spliced mRNA for the full-length of the transmembrane type of IRTA2 (IRTA2c) that was used as the antigen. As shown in FIG. 4B, the IRTA2 primers generated DNA fragments with expected size from the RNA of the cells positive for IRTA2 expression in FACS. In contrast, no IRTA2 cDNA was amplified from the RNA of FACS-negative cells, except for the trace amounts of the PCR product in Ramos cells. The actin primers generated similar amounts of the DNA fragment from all cells.

Next, IRTA2 protein expression in several cell lines was examined by Western blotting using MAb F25 (FIG. 4C). The IRTA2 protein was detected in the three B-cell NHL (B-NHL) cell lines tested (SU-DHL-5, SU-DHL-6, and JD38) as bands around 150-kDa, which is the same size as the recombinant IRTA2 protein expressed in 293T cells transfected with an IRTA2 plasmid. MAb F25 also reacted to IRTA2-Fc in the same blot. In contrast, no IRTA2 bands were detected in Karpas 299 and L540 cell lysates.

FIG. 4D shows a summary of the detection of IRTA2 by different methods in various cell lines. There is a clear correlation in IRTA2 expression detected by FACS, mRNA expression detected by RT-PCR, and IRTA2 protein detected by Western blots.

Example 7

Expression of IRTA2 on HCL Cells from Patients

Figure 5:
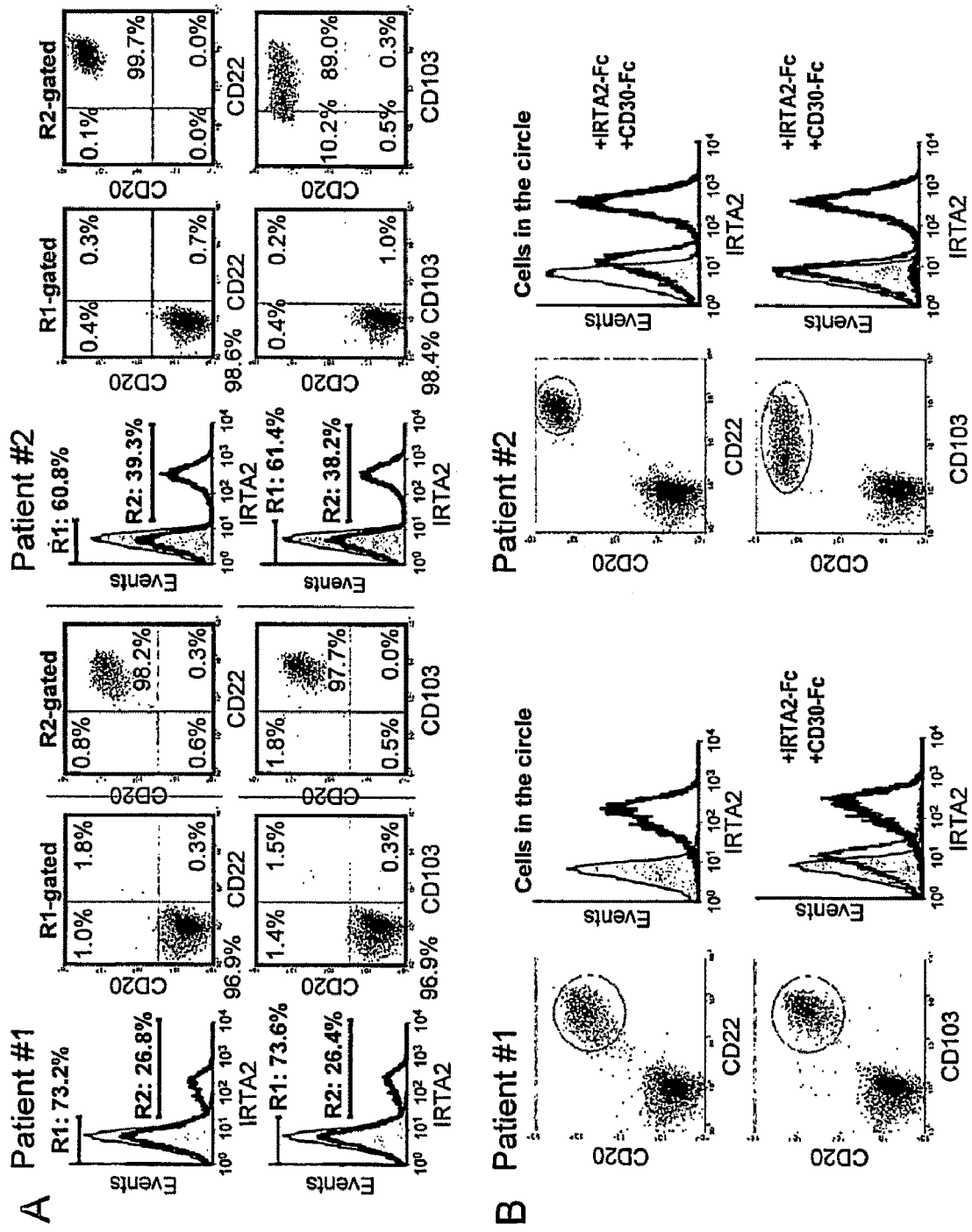
FIG. 5A-B are plots showing the expression of IRTA2 on HCL cells. PBMCs from two HCL patients were separated by a density gradient using Ficoll-Paque and 3-color staining was performed with CD22-FITC/IRTA2-PE/CD20-PerCPCy5.5 mixture or CD103-FITC/IRTA2-PE/CD20-PerCPCy5.5 mixture. Fluorescence associated with live cells was analyzed by FACS Calibure.

To determine if the MAbs might be useful for examining cells from patients, IRTA2 expression was analyzed in PBMCs of 5 patients with HCL and of 2 normal donors by FACS. In these experiments, the PBMCs were three-color-stained with anti-IRTA2 F56 and CD20 and CD22 or with F56 and CD20 and CD103. It was found that the HCL cells (CD20+, CD22+, and CD103+) from all five patients significantly expressed IRTA2 whereas IRTA2 was not detected on PBMCs of normal donors (CD14+, CD3+ or CD19+). FIG. 5 shows the typical results of a FACS analysis of 2 patients with HCL. Staining with anti-IRTA2 F56 revealed that 27% or 39% of the PBMCs from the 2 patients expressed significant amounts of IRTA2 (FIG. 5A, histograms). IRTA2 was not detected in PBMCs from normal donors. The IRTA2+ cells also expressed CD20, CD22 and CD103 (FIG. 5A, blue dot-blots), indicating almost all of IRTA2 positive cells represent HCL cells. On the other hand, almost all HCL-maker positive cells from the same patients (CD20+/CD22+ or CD20+/CD103+) expressed IRTA2 (FIG. 5B). These data show that all HCL cells in these patients express IRTA2. The IRTA2 signal was inhibited by the addition of a 100-fold excess amount of IRTA2-Fc (red lines in FIG. 5B) but not by CD30-Fc (blue lines), indicating that IRTA2 staining of the patient samples was antigen-specific.

Thus, the IRTA2 protein is expressed on the surface of many human lymphoma cell lines and on HCL cells from patients. The MAbs that bind IRTA2 can be used to identify patients with tumors that express IRTA2. These MAbs could be useful for both leukemia diagnosis and IRTA2-targeted immunotherapy. The staining of MAb F56 was always in accordance with that of MAb F119, although these MAbs belong to different subclasses (F56, IgG1; F119, IgG2b) and react with different epitopes (formalin-resistant epitope for F56 and formalin-sensitive epitope for F119). In addition, the staining was specifically inhibited by IRTA2-Fc, confirming the specificity of the staining. By using the highly specific staining, IRTA2 expression was detected on leukemia cells from five out of five HCL patients, whereas no IRTA2-positive cells were detected in PBMC from normal donors. Also, almost all IRTA2-positive cells expressed the markers for HCL (CD20+, CD22+, and CD103+) and almost all HCL cells were positive for IRTA2.

IRTA2 expression was detected in eight lymphoma cell lines out of 19 cell lines examined; these are mainly B-NHL cells. The expression profile was confirmed by RT-PCR and Western blotting, indicating that the FACS analysis using the MAbs is highly specific. The expression of IRTA2 in OCI-LY7, OCI-LY10, and Karpas 1106 is consistent with mRNA expression detected by DNA microarray. Thus, a FACS analysis is of use to screen IRTA2 expression on cells from patients with B cell malignancies.

The production of 36 anti-IRTA2 MAbs is disclosed herein. In this study, a MAb production method was utilized which generates a large number of MAbs in one fusion (see Nagata et al., *J Immunol Methods* 280:59-72, 2003). This method involves DNA-immunization followed by a cell boost and generated a large number of anti-IRTA2 MAbs. This method yielded a large number of MAbs, all of which reacted to the native form of IRTA2 on cells with high affinities (5.4 nM of Kd on average).

Out of the 36 antibodies, eleven cross-reacted with other IRTA family members. This high ratio of cross-reactive MAbs was expected as the IRTAs are highly homologous. All IRTA recombinant proteins were used to check the cross-reactivity; 25 IRTA2-specific MAbs did not cross-react with other family members. Among the 25 IRTA2-specific MAbs, MAbs F56 (IgG1) and F25 (IgG2a) are detected formalin-fixed antigen in cell-ELISA and immunofluorescence antibody, and SDS-denatured antigen in Western blots, respectively. Using an immunofluorescence technique, F56 specifically stained the plasma membranes of the 293T cells transfected with full-length IRTA2 plasmid (FIG. 3A). This result directly demonstrates the plasma membrane localization of IRTA2 protein.

Example 8

Design of Two Independent IRTA2-Specific Sandwich ELISAs

In order to measure soluble IRTA2 in human serum, four monoclonal antibodies (MAbs) to four different epitopes on the IRTA2 molecule were chosen from the panel of anti-IRTA2 MAbs shown in Table 4, and two independent ELISAs were constructed. ELISA#1 uses antibodies F1 and F25, while ELISA#2 uses antibodies F44 and F54. The performance of the ELISAs using a 1:100 dilution of samples of human serum was characterized.

Figure 9:
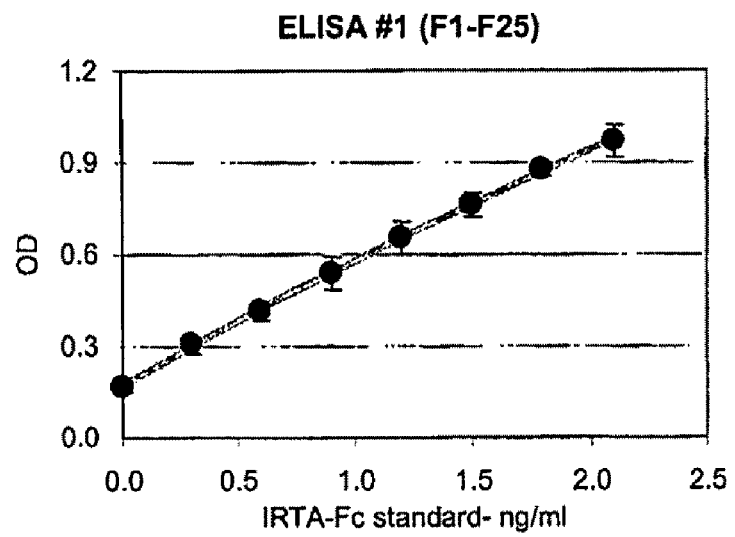
FIGS. 9A and B are graphs showing calibration curves using IRTA-Fc standard for ELISA #1 (FIG. 9A) and ELISA #2 (FIG. 9B).
Figure 9:
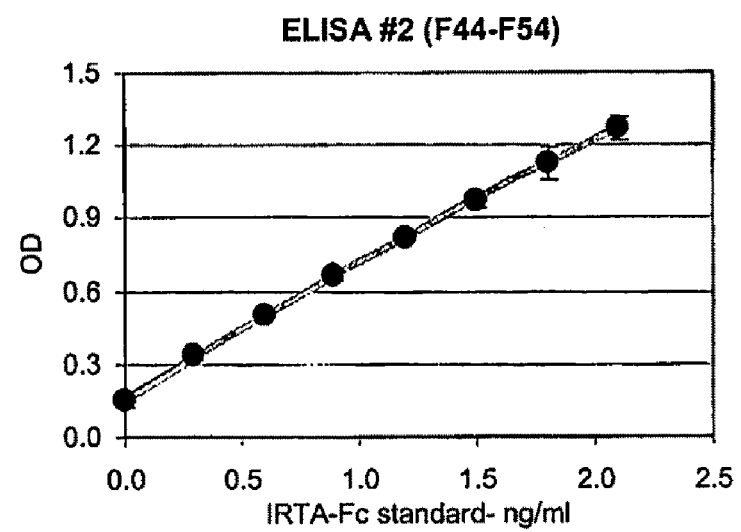

Initially samples were analyzed from normal donors (n=123) to establish a reference interval. When the $95^{th}$ percentile values of sIRTA2 level were taken as the cut-off, the reference intervals were <30-375 ng/mL for ELISA#1 and <30-377 ng/mL for ELISA#2. Typical standards curves were obtained from both of the two ELISAs in the range of 0.3-2.1 ng/ml of IRTA2-HFc protein as the standard (FIGS. 9A-9B). The ELISAs are able to measure 30 ng/ml to 5.2 µg/ml of soluble IRTA2.

Figure 10:
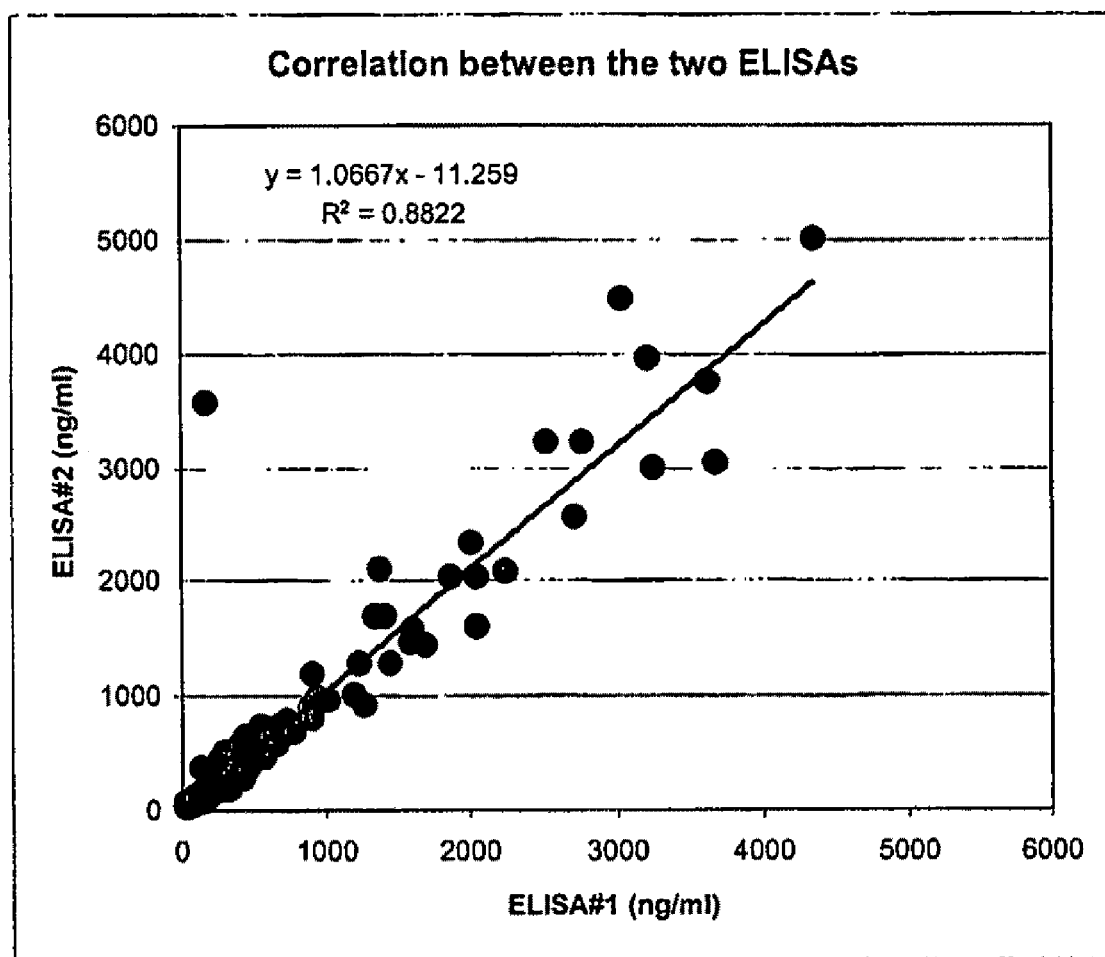
FIG. 10 is a graph showing correlation of ELISA #1 and ELISA #2.

The results of the two ELISAs were well correlated to each other, even though they use different sets of the epitopes on IRTA2 (FIG. 10). No bias and no artifact of the two ELISAs were found.

Example 9

Elevation of Soluble IRTA2 (CD307) Level in Hematological Malignancies

Figure 11:
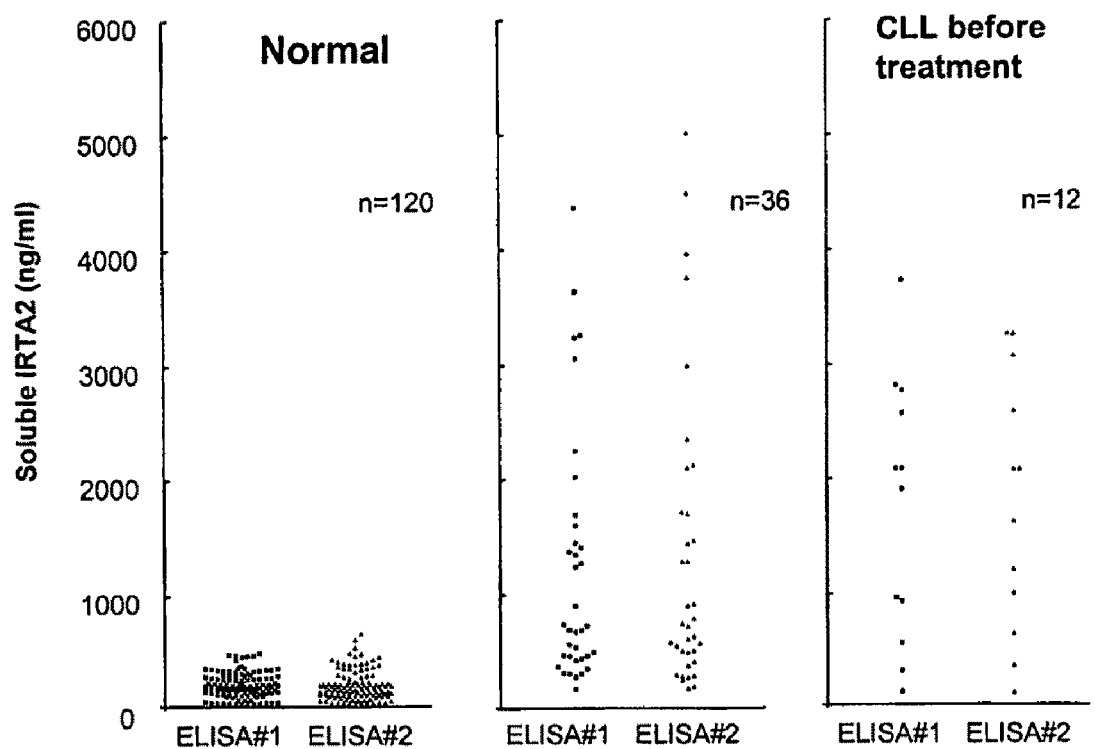
FIG. 11 is a graph showing the amount of soluble IRTA2 (ng/ml) in patients' sera as tested in the two ELISAs.

The sera of patients with hematological malignancies was screened for the presence of sIRTA2 by using the two ELISAs designed above. The ELISAs were performed as follows: MAb F1 (5 µg/ml for ELISA#1) or MAb F44 (5 µg/ml for ELISA#2) was diluted in PBS. 50 ul/well (50 ng/well) was added to Nunc-Immuno™ Plate MaxSorp™ (Nunc 439-454) and the plate was incubated at 4° C. overnight. 100 ul/well of blocking buffer (1% bovine serum albumin (BSA) (Roche 100350, Fraction V, protease-free), 0.1% sodium azide in PBS) was added and the plate was incubated at room temperature for at least 30 min. The serum samples and standards (IRTA2-Hfc) were diluted with blocking buffer containing 0.5% mouse serum (normal mouse serum, Zymed) and the plates were washed once with PBS-0.05% Tween (Tween 20, FisherBiotech 337-500 enzyme grade). 50 µl/well of the samples were added and the plate was incubated at 4° C. overnight. The plates were washed twice with PBS-Tween, and then 50 µl/well of 0.5 µg/ml of biotin-MAb F25 (ELISA#1) or 1 µg/ml of biotin-MAb F54 (ELISA#2) in blocking buffer containing 0.05% Tween 20 was added. The plates were incubated at room temperature for at least 60 min. The plates were washed three times with PBS-Tween and 50 µl/well of a 1/3000 dilution of HRP-streptosavidin (Biosource) in blocking buffer containing 0.05% Tween 20 was added. The plates were incubated at room temperature for at least 60 min. The plates were washed four times with PBS-Tween and 100 µl/well of TMB-hydrogen peroxide mixture (Pierce TMB substrate kit #34021) was added. The plates were incubated at room temperature for 10-30 min. 50 µl/well of 1M sulfuric acid was added to stop the reaction and the OD was measured at 450 nm with 650 nm as a reference. Standard curves were fitted to the second degree of polynomial curve after log conversion of the concentrations (using SoftMaxPro software, Molecular probes). From the calculated values and the dilutions, the IRTA2 concentrations in the human serum samples were determined. Using ELISA#1, an increase of sIRTA2 levels was found in 34 of 44 HCL (77%), 17 of 21 CLL (81%), 0 of 10 CML (0%), 0 of 9 ALL (0%), 0 of 9 AML (0%) 1 of 4 ATL (25%), 13 of 24 MCL (52%), 0 of 17 DLBCL (0%), 3 of HIV-lymphoma (33%), and 0 of 4 HD (0%). The sIRTA2 levels were confirmed by ELISA#2 which independently detects two different epitopes on sIRTA2. Surface IRTA2 expression was also detected in 4 of 7 CLL cells by a FACS analysis using an anti-IRTA2 MAb. Using these ELISAs, an elevated level of IRTA2 was detected in HCL and CLL patients compared to normal (FIG. 11).

The finding that sIRTA2 was elevated in various hematological malignancies indicates that sIRTA2 could be a good tumor marker for the prediction and monitoring of these diseases and also suggests that sIRTA2 could be involved in the biology of these malignancies.

It will be apparent that the precise details of the methods or compositions described may be varied or modified without departing from the spirit of the described invention. We claim all such modifications and variations that fall within the scope and spirit of the claims below.

The invention claimed is:

1. An isolated monoclonal antibody or an antigen-binding fragment thereof, wherein the antibody comprises
    A light chain with a L-CDR1, L-CDR2 and L-CDR3 region, and wherein L-CDR1 comprises the amino acid sequence set forth as amino acids 24 to 35 of SEQ ID NO:4, L-CDR2 comprises the amino acid sequence set forth as amino acids 51-57 of SEQ ID NO:4, and L-CDR3 comprises the amino acid sequence set forth as amino acids 90-98 of SEQ ID NO:4;
    and wherein the antibody comprises a heavy chain with a H-CDR1, H-CDR2 and H-CDR3 region, and wherein H-CDR1 comprises the amino acid sequence set forth as amino acids 31 to 35 of SEQ ID NO:3, H-CDR2 comprises the amino acid sequence set forth as amino acids 50 to 67 of SEQ ID NO:3, and H-CDR3 comprises the amino acid sequence set forth as amino acids 100-107 of SEQ ID NO:3,
    wherein the isolated monoclonal antibody specifically binds the amino acid sequence set forth as amino acids 287 to 565 of SEQ ID NO: 13.

2. The isolated monoclonal antibody of claim 1, or antigen binding fragment thereof, wherein the antibody comprises a human framework region.

3. The isolated monoclonal antibody of claim 1, or antigen binding fragment thereof, wherein the antibody comprises a murine framework region.

4. The isolated antigen binding fragment of the monoclonal antibody of claim 1.

5. The isolated antigen binding fragment of the antibody of claim 2, wherein the antigen binding fragment comprises an Fv, an Fab, or an F(ab')$_2$.

6. The isolated monoclonal antibody or antigen binding fragment of claim 1, conjugated to an effector molecule.

7. The isolated monoclonal antibody or antigen binding fragment of claim 6, wherein the effector molecule is a toxin.

8. The isolated monoclonal antibody or antigen binding fragment of claim 7, wherein the effector molecule comprises ricin A, abrin, diphtheria toxin or a subunit thereof, *Pseudomonas* exotoxin or a portion thereof, saporin, restrictocin or gelonin.

9. The isolated monoclonal antibody or antigen binding fragment of claim 8, wherein the effector molecule comprises a *Pseudomonas* exotoxin, wherein the *Pseudomonas* exotoxin comprises the amino acid sequence set forth as SEQ ID NO: 53 (PE40), SEQ ID NO: 54 (PE38), SEQ ID NO: 55 (PE38 KDEL), SEQ ID NO: 56 (PE38REDL) or SEQ ID NO: 57 (PE4E).

10. A composition comprising a therapeutically effective amount of the antibody of claim 1 in a pharmaceutically acceptable carrier.

11. A method for detecting soluble protein comprising the amino acid sequence set forth as amino acids 287 to 565 of SEQ ID NO: 13 in a sample, comprising:
    contacting the sample with the isolated monoclonal antibody of claim 1, the antigen binding fragment thereof or a humanized form thereof to form an antibody protein complex; and
    detecting the presence or absence of the complex,
    wherein presence of the complex detects the soluble protein.

12. The method of claim 11, wherein the monoclonal antibody, humanized form thereof, or antigen binding fragment is labeled.

13. The method of claim 12, wherein the label is fluorescent.

14. The method of claim 11, wherein the method comprises an enzyme-linked immunosorbent assay (ELISA).

15. The isolated monoclonal antibody of claim 1 or antigen binding fragment thereof, wherein a light chain variable region of the antibody comprises the amino acid sequence set forth as SEQ ID NO: 4.

16. The isolated monoclonal antibody of claim 1, or antigen binding fragment thereof, wherein a heavy chain variable region of the monoclonal antibody comprises the amino acid sequence set forth as SEQ ID NO: 3.

17. A hybridoma that produces the monoclonal antibody of claim 1.

* * * * *